United States Patent [19]

Behram et al.

[11] Patent Number: 5,499,293
[45] Date of Patent: Mar. 12, 1996

[54] PRIVACY PROTECTED INFORMATION MEDIUM USING A DATA COMPRESSION METHOD

[75] Inventors: Sepehr Behram; Nancy T. Grauzlis, both of Hampton, Va.; Sammy W. Joseph, Derwood, Md.

[73] Assignee: University of Maryland, College Park, Md.

[21] Appl. No.: 378,165

[22] Filed: Jan. 24, 1995

[51] Int. Cl.⁶ ........................................... H04L 9/00
[52] U.S. Cl. ........................ 380/4; 364/413.02; 341/51; 341/106
[58] Field of Search ...................... 380/4, 23, 24, 380/25; 364/413.02; 341/51, 55, 90, 91, 92, 95, 106; 235/375, 380

[56] References Cited

U.S. PATENT DOCUMENTS

| | | | |
|---|---|---|---|
| 4,108,362 | 8/1978 | Trussell et al. | 235/375 |
| 4,295,124 | 10/1981 | Roybal | 341/106 X |
| 4,491,725 | 1/1985 | Pritchard | 235/375 |
| 4,614,366 | 9/1986 | North et al. | 235/375 |
| 4,632,428 | 12/1986 | Brown | 283/76 |
| 4,780,599 | 10/1988 | Baus | 235/375 |
| 4,843,389 | 6/1989 | Lisle et al. | 341/106 |
| 4,857,713 | 8/1989 | Brown | 235/375 |
| 4,874,935 | 10/1989 | Younger | 235/375 X |
| 4,876,541 | 10/1989 | Storer | 341/51 |
| 4,896,027 | 1/1990 | Drexler | 235/488 |
| 5,006,849 | 4/1991 | Baarman et al. | 341/106 X |
| 5,051,745 | 9/1991 | Katz | 341/67 |
| 5,182,772 | 1/1993 | Karas et al. | 380/59 X |
| 5,243,341 | 9/1993 | Seroussi et al. | 341/51 |
| 5,323,155 | 6/1994 | Iyer et al. | 341/51 |
| 5,337,358 | 8/1994 | Axelrod et al. | 380/23 |
| 5,412,727 | 5/1995 | Drexler et al. | 380/24 |

OTHER PUBLICATIONS

Stobart, B. A. et al.; "An Integrated Hospital Computer System"; Systems Technology; Dec. 1978; pp 20–25.

Primary Examiner—Tod R. Swann
Attorney, Agent, or Firm—Christopher N. Sears

[57] ABSTRACT

The present invention uses an efficient data compression/decompression scheme using a passive data storage media such as a card-based approach for storage of medical data information. The invention operates on existing personal computer hardware in a medical center or doctors' offices, doing away with expensive investments in specialized technologies of central processing hardware. The invention is very economical to implement, at a cost of less than a dollar per card generated for a patient's use. With the advent of inexpensive desktop computing, a number of inventions have been offered to improve medical information storage and retrieval. They include the development of portable medical card technologies such as SmartCards and optical cards which are capable of storing medical information and can be carried by the patient. This card based system provides a methodology for storage and retrieval of medical information from a passive credit-card sized instrument. The card is manufactured with minimal expense using existing well known optical scanning or magnetic tape reading or a data interrogation means in a SmartCard based system.

15 Claims, 6 Drawing Sheets

Patient Data Summary

I. Demographic Information

II. Past Medical History

III. Past Surgical History

IV. Medications

V. Allergies

VI. Immunizations

VII. Screening Procedures

VIII. Living Will Status

IX. Organ Donor Status

X. Special Comments

---

Smith, John                                      December 20, 1993

| | | |
|---|---|---|
| v2WmvOhdvOgjv2WivyRvv1Dpv2KKv2WmvOOav2Wk | 48 | 92 |
| v2PfvOEcv2Wpv2Wmv1iWvOKgvyRvv1Dpv2KKv2Wm | 98 | 66 |
| v2Wn4shXLSWsFyIyTyOYGE3Wng1TzBH8TQpxp8Tp | 23 | 57 |
| Bww2VGzmaUzR4v2WG36sv2WTvz9Vv2WJ3tzv2WKv | 37 | 47 |
| z9Vv2WL4fav2WIvy9FvyDr3jOv2WIvyjevv3O3mx | 9 | 39 |
| v2WTvyufv2Wq4b3v2Wrv1TWv2Ws4Kgv2WTv2Wtvz | 7 | 17 |
| bJ4ELv2WTvyICv2Xz3D4v2WTvyIC3v2WM4YQv2WN | 46 | 2 |
| vyICv2WO4PQv2WPvvWNv2WQ4Xgv2WRvy9Fv2WS3V | 64 | 81 |
| kv2WTvy9Fv2WU3Div2WTvxuPv2Xv4kTv2WRvz9Vv | 25 | 14 |
| 2Xw4kfv2WRvz9Vv2Xy4Ukv2Wrvz9VOvwaE4PQv2W | 78 | 22 |
| VvvWNvvEX4ohv2WWvvWNvy2L4nkv2WXvy9FvvPD4 | 93 | 72 |
| hsv2WVvyjevOKg4sAv2WZvyufOvxKev2Wavv9FvO | 8 | 53 |
| 3Lv1n3xv2Wb4ohv2Wc4jFzv2Wd4iiv2WKv2We4iF | 46 | 90 |
| v2WKv2Wf4iFv2WKv2Wu4e4v2WrDIv1dAv2WhvxyV | 34 | 3 |

PRIVACY PROTECTED INFORMATION MEDIUM USING A DATA COMPRESSION METHOD

FIELD OF THE INVENTION

This invention pertains to a data compression/decompression methodology and means for storage of information on a data storage medium such as a card where confidentiality of the data is a consideration in the design thereof. The methodology is particularly suited for storage of a patient's medical data on a portable card for inteneded decentralized data storage.

NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

There is a continuing need to take the bundles of information that bombard today's hospital patients, business concerns and consumers and provide ways for more efficient organization thereof. The continuing evolution of computer based technologies will allow consumers and business concerns to use/employ wallet sized cards that can hold diverse individual information. Areas of individuated informational importance include: medical finance/credit worthiness of a consumer, commercial inventory data, automotive service history, military, academic, insurance and employment records etc. Moreover, for these applications, there is a long sought need for a system that allows the consumer/business concern to carry such large amounts of informational data on a simple medium such as a single card, while also maintaining the confidentiality of such information without the need for a central data file thereof while also allowing ease of transmission over digital informational data transmission highways. Moreover, such a card saves both time and aggravation to a consumer and businessman by providing portability while maintaining the privacy thereof. In particular, such cards are becoming more widely used in the medical field; an example being a driver's license card that contains organ donor status. Additionally, portable medical record cards are becoming an important objective in this era of healthcare reform. There have been a number of strategies devised to implement portable medical information cards. These strategies may be divided into two broad categories: i) a system which relies on a central database; and ii) a system which stores the information directly onto a card.

A Centralized Approach:

Such a strategy would store personal medical information in a vast centralized database. Hospitals and healthcare workers connect with a centralized service and download the desired information. Patients may carry credit-card size cards which are encoded with a unique code which positively identifies the patient. Such a code may take the shape of bar-codes,an encoded magnetic strip or make use of other types of media. The patient usually gives the card to a healthcare provider for scanning. The encoded identification information is used to download the patient's medical history through a communications link with a centralized database. Such a "credit-card" type system should not be confused with the card-based system which stores the medical information directly onto the card as the present invention does.

A centralized system has a number of drawbacks. First, such networks are expensive to create and maintain. An example of this type system is taught in U.S. Pat. No. 5,325,294 entitled "Medical Privacy System." Limitations of such a centralized computer or multiple local network computers include: i) having to work constantly to download information to peripheral locations upon request; and ii) having the patient's data kept in one location which potentially jeopardizes the patient's right to privacy along with a need for security thereof. Finally, nationwide networks of a centralized system is many years away from use. There are many other ways of creating a portable medical system which are cost-effective and allow for decentralized information storage capability. Such systems include U.S. Pat. No. 4,491,725 entitled "Medical Insurance Verification and Processing System." Limitations of this teaching include:i) it does not teach or suggest ways for compression/decompression of a patient's medical dats history that would in turn would allow for a more flexible modification of data entered onto the card where overall system may change at a later date; or ii) insure patient privacy and confidentiality. Both of these limitations are addressed herein.

Card-Based Approach:

Unlike a centralized approach where information is stored in one area and dispersed peripherally, the card-based approach seeks to place the information peripherally. All of the information is encoded directly on a card or other similar media. There is no need for a large, centralized database or for a communications network to process the information on the card. Well known approaches include:

1. SmartCards/Optical cards. These are small, portable cards which can carry a substantial amount of medical information. The mechanism of storage involves a small computer chip which is part of the card itself. The chip contains memory which is used to store the information. Some specialized equipment is necessary to read and write information onto the chip. With recent technological advances, it has become possible to mass produce these chips to make it an economical alternative. The current optimistic projections of the cost of such a system run about $30 per card. This does not include the cost of the specialized read/write equipment which is necessary at all the medical centers and doctors' offices. Still, SmartCards are said to be more cost-effective than a centralized database and they offer the advantage of being available for mass use in a few years. In contrast, the instant invention allows for the encoded information to be entered onto a card in alphanumeric form and be retrieved by an optical scanner at cost less than a dollar. However, the present invention may use a SmartCard as a storage medium of the medical data to increase the data storage capability of this device. Another approach is an optical storage card which stores medical data in optical electronic form. Although mechanically different than SmartCards, this technology is still limited by large overhead costs and production costs.

2. Microfiche. This is an older technology but one which offers greater savings and greater data storage capability than a SmartCard. Various schemes have been developed to place microfiche onto a pocket-sized card which can be distributed to the patient for later use. Examples of such a technique includes U.S. Pat. No.

4,632,428 entitled "Combination Medical Data, ID & Health Insurance Card," U.S. Pat. No. 4,896,027 entitled "Portable Detachable Data Record." and U.S. Pat. No. 5,215,334 entitled "Emergency Medical Card." Unfortunately, these systems have a number of drawbacks which limits their acceptance in the medical field. Limitations include: i) the need for microfiche readers and copiers which are expensive equipment; ii) all medical centers must be equipped with such devices in order to make use of this technology which is another capital investment for these centers; iii) the lack of security measures to prevent unauthorized review of the card by another individual equipped with a microfiche reader; and iv) this type of system is difficult to update and produce a new card in a timely manner for a patient. In view of these problems, the invention herein solves them by a data compression methodology that can generate an updated privacy-protected card on demand whose large storage media capability is in a decentralized form.

Data Compression/Decompression:

Dictionary-based compression algorithms are of particular interest, and these form a large subSet of all compressive techniques. There are two main approaches to using a dictionary-based system: i) Those using an adaptive or dynamic dictionary; and ii) Those using a static dictionary. A dynamic dictionary system is one which is usually derived "on the fly" as the software samples the data which is to be compressed. Unfortunately, dynamic dictionaries are of minimum benefit for certain applications such as portable informational records since: i) such dictionaries are non-uniform, i.e. there is no "standard" dictionary at each node, and ii) they yield lower overall compression/decompression rates.

A static dictionary system is better suited for applications such as portable informational records. A single, unique dictionary at each site can insure uniform coding of information with a very high yield. The current technology does not readily allow for easy periodic updates of a static dictionary. Any modification of the original dictionary will jeopardize the system's ability to decompress information encoded using the previous version of the system's dictionary.

As an example of a portable data record, a patient's medical record is illustrative therof. The dictionary used in such a scheme generally has to be modified annually to reflect new medications available on the market, new medical centers formed across the country, etc. Unfortunately, each time the dictionary is updated with new information, the cards generated prior to the update would become invalid. Current technology offers few solutions to this problem other than maintaining copies of an older dictionary for use in decoding cards generated using that dictionary. With very large dictionary databases, this becomes prohibitive.

The invention herein uses a new method which modifies static dictionaries which are defined as Very Large List (VLL). The VLL is actually composed of a primary dictionary and a two secondary dictionaries. The primary dictionary contains target words and phrases and the secondary dictionaries contain specialized pointer information. This approach, which is referred to as the "VLL concept," permits the development of modifiable static dictionaries which are necessary for the development of particular applications such as a portable medical record. The invention herein differs from prior compression systems in that it links two types of storage media and "borrows" space from the media with the greater capacity in order to increase the information density on the lesser capacity media. The two storage media consist of the computer hard drive and the small computer printed information storage media such as a card. The methodology of the instant invention system can increase the information density of a card where space may be limited, by using hard disk space of a computer with large data storage capacity. The information card, thus can carry greater data than would otherwise be possible in such a system configuration.

SUMMARY OF THE INVENTION

The present invention uses an efficient data compression/decompression scheme using a passive data storage media such as a card-based approach for storage of medical data information. The invention operates on existing personal computer hardware in a medical center or doctors' offices, doing away with expensive investments in specialized technologies of central processing hardware. The invention is very economical to implement, at a cost of less than a dollar per card generated for a patient's use. With the advent of inexpensive desktop computing, a number of inventions have been offered to improve medical information storage and retrieval. They include the development of portable medical card technologies such as SmartCards and optical cards which are capable of storing medical information and can be carried by the patient. The benefit of such portable information systems for improving the quality of primary care as well as increasing the cost/effectiveness of health care delivery is well known. Unfortunately, a number of obstacles including: i) high end-user fees; ii) security concerns regarding patient confidentiality; and iii) technical barriers prevent immediate widespread use of these technologies. The invention provided herein provides a methodology for storage and retrieval of medical information from a passive credit-card sized instrument. The card can be immediately manufactured with minimal expense using existing well known optical scanning or magnetic tape reading technologies are used.

OBJECTS OF THE INVENTION

Accordingly, several objects and advantages of the present invention are:

An objective of the invention is to provide a portable data storage medium that is: i) compatible with digital data transmission systems that: ii) insures personal privacy and accuracy of the medium, and iii) is very inexpensive to make and usable with existing personal computer hardware;

Another objective of the invention is an efficient data compression/decompression methodology for an informational system that allows for infinite upgrades of a primary and secondary static dictionary used in the data compression system without jeopardizing the decoding power of the dictionary in decompressing information generated by the previously used primary dictionaries of the system; and Yet, another particular objective of the invention is: i) to provide a medical data storage card that fully ensures privacy and accuracy of a patient's medical file, ii) is compatible with future fiber optic based informational networks and iii) operates on existing and inexpensive personal computer hardware.

Still further advantages will become apparent from consideration of the ensuing detailed description.

BRIEF DESCRIPTION OF THE DRAWINGS

FIG. 3 shows a sample medical profile generated from an alphanumerics card as discussed in the methodology section herein.

DETAILED DESCRIPTION

Figure 1:
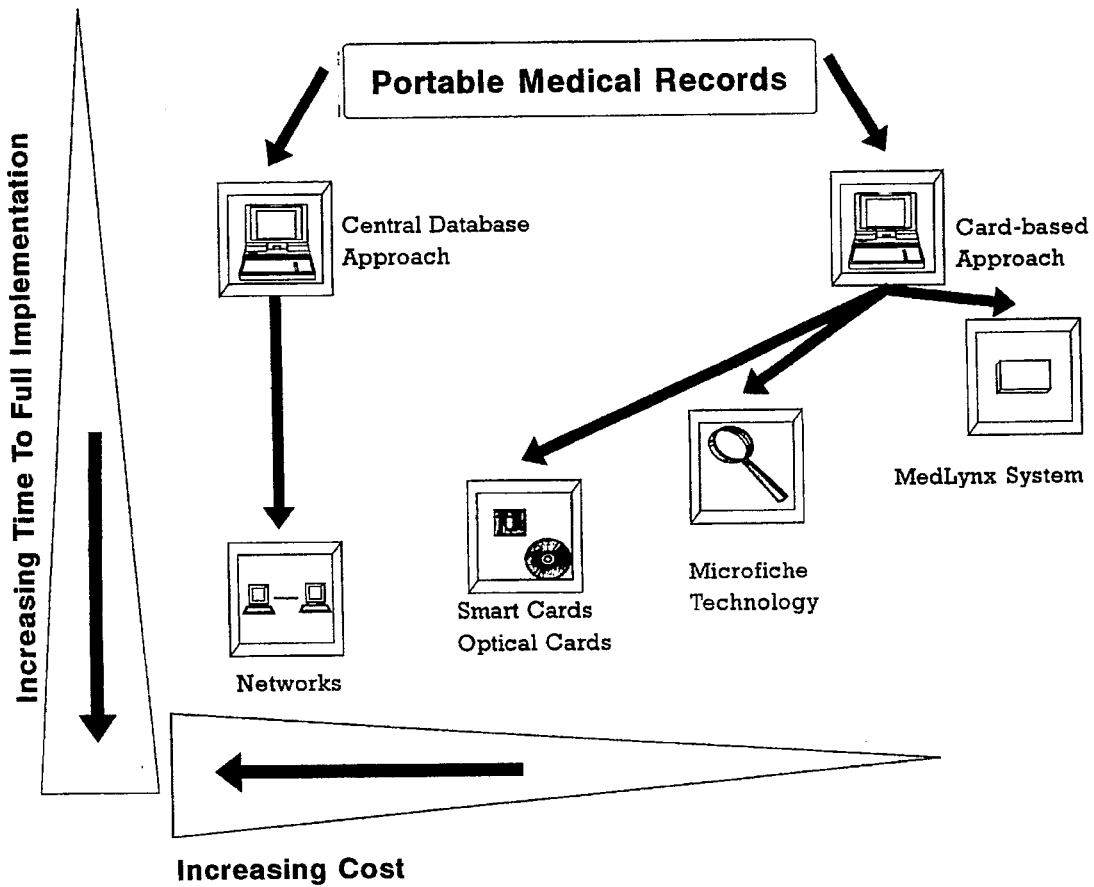
FIG. 1 shows various strategies for achieving portable medical records where the instant invention is the most cost effective.

The invention herein maintains the confidentiality of data records in general. In particular, a medical patient's records is used a an important example of the invention. The system described herein deals with medical applications and is referred to as the MedLynxTM system which includes the software implementation thereof. This system is for healthcare professionals to facilitate services to a patient while maintaining a patient's privacy interest. Unlike regular medical records, the MedLynxTM system uses a unique data compression scheme to code important medical information into a small space so that the patient can transport his or her medical record conveniently without need for a central data storage system.

A patient seeking medical attention can present the MedLynxTM card to a healthcare provider. Since the information is encoded on the card itself, any physician with access to the MedLynxTM software can decompress the information to generate a summary of that patient's important medical information. If the patient does not have a MedLynxTM card, a new card can be generated for the patient at end of the visit. The medical information on the card can always be updated and a new card generated after each visit. The MedLynxTM system can be a life-saving tool in situations where past medical history is critical, but not immediately available. A summary report from the card can be generated in a matter of minutes and can provide a physician with reference information regarding past medical history, past surgical history, list of medications, list of allergies, list of vaccinations, list of screening procedures, including the names of the physicians, the names of the medical centers and the dates associated with each entry. Furthermore, the card can provide a doctor with information about organ donor status, a living will, emergency telephone contact numbers and access to brief comments and reminders written by other physicians. Finally, each card can encode demographic information which has other applications.

This particular example illustrates a sample implementation of the compression/decompression technique of the invention herein that provides a card based system that integrates a patient's health care delivery with a convenient means to access to their medical records that allows a patient to always carry a copy of their medical history in their wallet or purse. Various aspects of the MedLynxTM software/system include:

Convenience to the Patient:

In deciding on storage medium for the MedLynxTM software/system, user convenience is the most important factor by use of a small and inexpensive hand carried record. Second, the card based information must be easy to replace and easy to update. The patient should be able to make duplicates of this information so as to distribute them in various locations for easy emergency access. As an example, an enlarged size card is shown in FIG.3 in alphanumeric form. The card is inexpensive to generate at pennies per card. The MedLynxTM software/system, however, is in no way limited to a single medium. The same information which appears on the cards can be recorded as bar codes for scanning purposes or the information can be converted onto magnetic strips much the same way information is encoded on a credit card or ATM machine. The card of this system can be readily adapted to alternate storage media such as SmartCards.

Convenience for Health Care Professionals:

The MedLynxTM system is a desirable communications access system for healthcare workers. Since the information travels with the patient, one physician can directly communicate with the next physician the patient will consult. Important reminders and important notes can be passed along and redundancy in repeating the same laboratory or diagnostic procedures can be minimized. The MedLynxTM database can assist in maintaining accurate and up-to-date vaccination information and tracking routine age-related screening procedures to insure that they have been performed.

Since the MedLynxTM protocol depends on a large database of information, it is crucial that these databases are easy to update. The database can be updated with an "update disk" with no need to recompile the MedLynxTM cards issued prior to the update. In other words, the MedLynxTM card remains valid and will yield the same information even if the MedLynxTM methodology is modified at a later date. Update information on the card can be distributed by many modalities including compact discs (CD-ROM), fiber optics, local area networks, and modems.

Economy:

This invention makes use of the existing technological infrastructure. Most medical centers and doctors' offices already have access to a personal computer (PC) which can be used, as needed, to compress and decompress medical information using this system. There is no need to invest in a SmartCard interface, optical card read/write equipment, microfiche equipment or networking capability. Start-up and maintenance costs of such a system are minimal. Since the cards can be printed on paper (as alphanumerics or one or two-dimensional bar-codes) or on reusable magnetic stripes like a bank card, cost to the patient is minimal.

Minimal system requirements to support this system can include a PC based 80286 processor with 1 Mb RAM and a printer associated therewith. If hardware add-ons such as scanners, bar code readers, or magnetic readers may be necessary, they can readily be made compatible with an existing system that uses the invention's data compression/decompression technology. An inexpensive computer environment would matter little, however, if the output required on an expensive medium. The output from the most basic system is a small card at costs of a few pennies. The card is low-maintenance and can be inexpensively reproduced. The data compression methodology of the instant invention compresses medical information to a ratio of 10:1. This unique feature makes it possible to compress large volumes of information into smaller strings of alphanumerics or bar-codes or magnetic signals which can be stored on a small card.

Security and Confidentiality:

Medical data storage of any kind can always have a dangerous potential of misuse. Medical information can be used by unauthorized individuals for illegal purposes such as dropping insurance coverage, termination of employment or even for social or political purposes. For these reasons, the MedLynxTM system allows for restricted use by physicians and their agents.

The MedLynxTM system offers a number of security features above and beyond a simple password keycode. The data on each card is scrambled by two different algorithms and can be decoded only with the original cipher chosen by the patient. If the patient wishes to waive their right to privacy, he or she may choose to print their password on the back of their card, making the information on the card accessible in the event of an emergency. Also, while the patient card contains a patient's name in a humanreadable form, the data matrix on the card does not encode for any identifying information. Electronic infiltration into computer memory will not yield any useful information about the patient because all the data remains anonymous while in electronic form.

To further enhance data security, each MedLynxTM card is encoded by two different schemes. The information can only be decoded with the proper authorization code selected by the patient. While this security feature is designed for the protection of the patient's right to privacy, an individual may wish to waive this right in which case he or she would hand-print his or her security code onto the card to insure that the card would remain useful even if they become incapacitated.

As a final security feature, it was decided that the patient name would be typed directly onto the card but would not be coded within the MedLynxTM information matrix. The resulting medical summary will not contain the patient's name. There will be no linking information between the medical summary document and the MedLynxTM card which the patient carries. Many medical centers may run the patient's addressogram on the medical summary document and by doing so, they enter this document into the medical chart. At this point, the medical summary will become part of the medical record and the center can assume the responsibility for insuring proper care and handling of this document.

Accuracy in Data Storage:

The prototype model requires keyboard entry of the MedLynxTM data which is printed on the card. There are many technologies already in existence which can circumvent this step including scanners, bar code readers, and magnetic readers. Various measures are used to insure accurate data entry.

Each line of data on the MedLynxTM card is followed by two checksum values which must exactly match the checksum values seen on the computer for each line of data entered. This insures errorfree data entry which is critical in situation's where a patient may be unconscious and verification of the actual data may mean the difference between life or death.

Since the data is encoded for security as discussed above, it is crucial to insure correct decryption. This is achieved by encoding the several letters of a patient's preferred name, e.g. their mother's maiden name, or another password "key code" onto the card. This password "key code" will be requested and if the response agrees with the information recorded on the card, correct decryption can be guaranteed.

The MedLynxTM system also can be of great help in epidemiological studies. Since the information can be decoded anonymously, a patient's right to privacy can always be preserved. The MedLynxTM ,system can be used as a powerful research tool to study disease and illness. It could potentially simplify record searches making it possible to study larger number of cases in a shorter period of time.

With the increasing trend toward automation, MedLynxTM can be an important tool in decreasing redundant keystroking of data as well. Since all the information passing through the MedLynxTM system is electronic, the output can be transmitted to other applications such as computerized billing programs or insurance claim forms. As new health care reforms begin to be formulated and used in the future, greater emphasis will be placed on automation and economy by health care providers. Thus, the MedLynxTM system can be incorporated into an existing medical delivery system.

Figure 2:
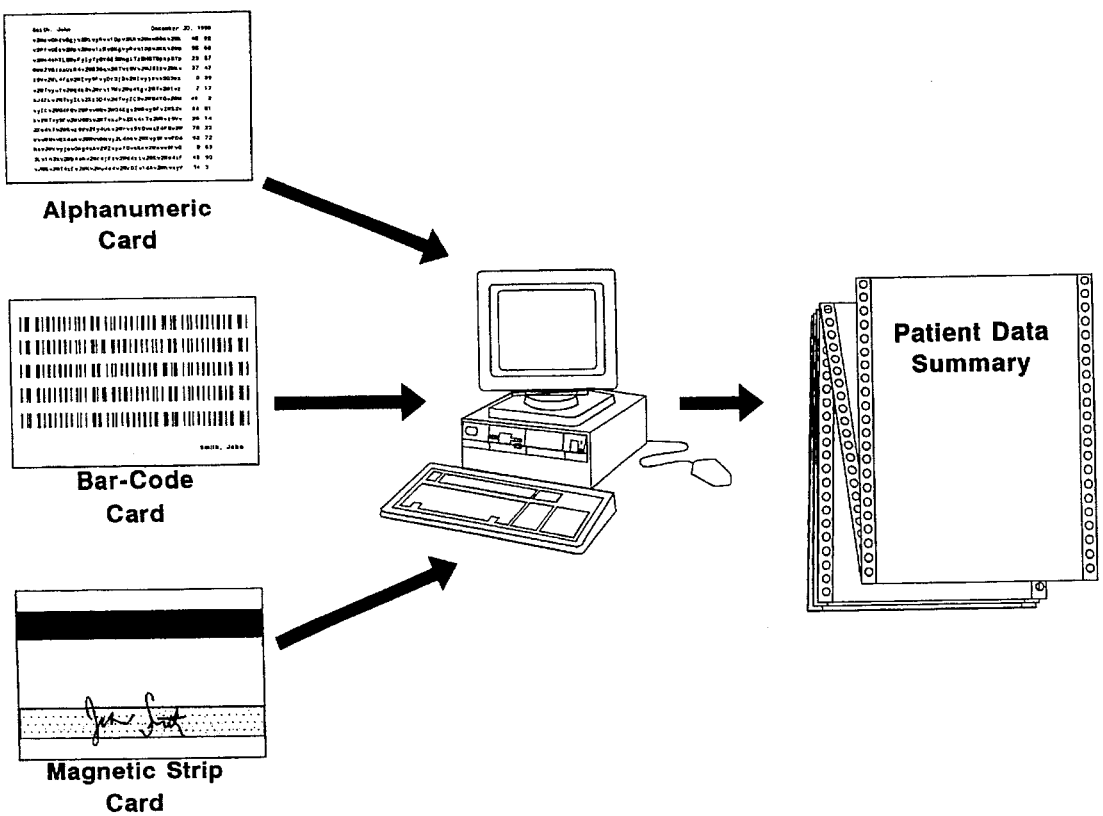
FIG. 2 shows the flow of information of a typical medical record wherein a patient's encrypted medical data card; the information is entered into the computer by an appropriate data entry means & a printout of the patients record is made available.

MedLynxTM Methodology:

Minimal hardware requirements are required to use the MedLynxTM system, in particular: an PC 80286 based microprocessor with 1 Mb RAM, along with 3 Mb Hard disk space, a printer, and an appropriate input/output hardware. The MedLynxTM methodology can be readily modified for use on other computer systems and be written in various computer languages. The MedLynxTM software system compresses medical information into strings of alphanumeric characters which could fit on a card produced by the printer. The patient can carry the card with them for later use. The next health care provider caring for this patient can decompress the data from the card to reproduce the patient's original medical profile as shown in FIG. 2. At the conclusion of a patient's visit, the information on the card can be updated where a new card would be generated for the patient. There is no need for the computers to be in communication with each other since all of the medical information is contained on the card that the patient personally carries. The type of card generated with this system can take many different forms. An alphanumeric card uses an inexpensive "ink-on-paper" approach requiring only a hand-held scanner and optical character recognition software for use thereof. Alternatively, this new approach makes it possible to use bar codes, magnetic stripes, and other low cost technologies to store large volumes of medical information. This software system can also be linked to other software such as billing and insurance computer programs. The data from the card can be passed to these other programs so as to minimize repetitive data input and maximize automation.

The MedLynxTM methodology comprises a number of computer software programs that work together as a unit for input/output a a patients medical data. This methodology can accept uncompressed data which it can compress, or compressed data which it can decompress. It is referred to as an "engine" because the entire software system can be integrated into a larger system which can make use of the compressed/decompressed data. In such a case, the MedLynxTM "engine" will be responsible for furnishing the software application with compressed and/or decompressed data. The MedLynxTM system can be modified to accept any digital input the hardware can support and, similarly, the output is restricted only by the hardware considerations.

Data Compression/Decompression Design:

The data compression technique increases the information density of data recorded on a finite medium strategies in the past have relied on a simple dictionary algorithm.

As an example, the word "philosophy" can be stored using fewer than 10 characters by using the dictionary compression algorithm. As the name implies, a dictionary is necessary for use with this technique. For the compression of standard English words, a standard dictionary shared between the point of transmission and point of reception is required. Instead of transmitting the entire word, only its location in the dictionary needs to be transmitted. If the word "philosophy" was located on page 555, third word on the page, the address "55503" would be transmitted. This number serves as a jump vector which can be used at the point of reception to regenerate the original word. This represents only five characters of information. This number can be further compressed by using a numbering system with a base greater than ten. A base-10 number system runs: "0,1,2, . . . ,9,10,11, . . . "; A base-62 number system runs: "0,1,2, . . . ,9,A,B, . . . ,Y,Z,a,b, . . . ,y,z, 10,11, . . . " By converting from a base-10 to a base-62 system, the number "55503" could be transmitted using only three characters instead of five. The net result is the ability to transmit the word "philosophy" by using only three characters.

While the power of this technique is obvious, the limitations are subtle and may be overlooked. These shortcomings make this technique unfeasible for many real-world applications. Unfortunately, it has proved difficult to devise a "quick fix" to modify the technique to overcome these problems. Using individual words that compose a patient's medical history to be compressed into numerical strings by using the dictionary method discussed above, the word "philosopher" can be transmitted using three characters, all of these terms and phrases in a medical history can be similarly converted into shorter strings of characters. These final compressed products can be stored onto a card which the patient can carry until the information is needed again. Reversing this simple process allows extraction of the original information from the card. Considering the difficulty that would arise if a new term such as "Asperger's syndrome" was added to the lexicon. All of the words following this entry in the dictionary would be "shifted" by one location as this term is inserted alphabetically in the dictionary. Suddenly, the code "55503" which had previously coded for "philosophy," codes for a different word. All of the compressed information generated by the older dictionary must now be recalculated based on the new dictionary. If the lexicon is to contain current, dynamic information such as medical terms, names of new medications, names of new clinics and hospitals, etc., this technique would prove to be impractical. Because this technique is dictionary dependent, it would be very difficult to overcome this limitation. Also considering the issue of security, any individual using a known "dictionary" could potentially decompress the medical information. Techniques designed to add a password gateway to a computerized dictionary or to hide the dictionary from the user represent only a superficial attempt at security. A better approach would involve scrambling the data at the level of the compression/decompression software utilities.

Figure 4:
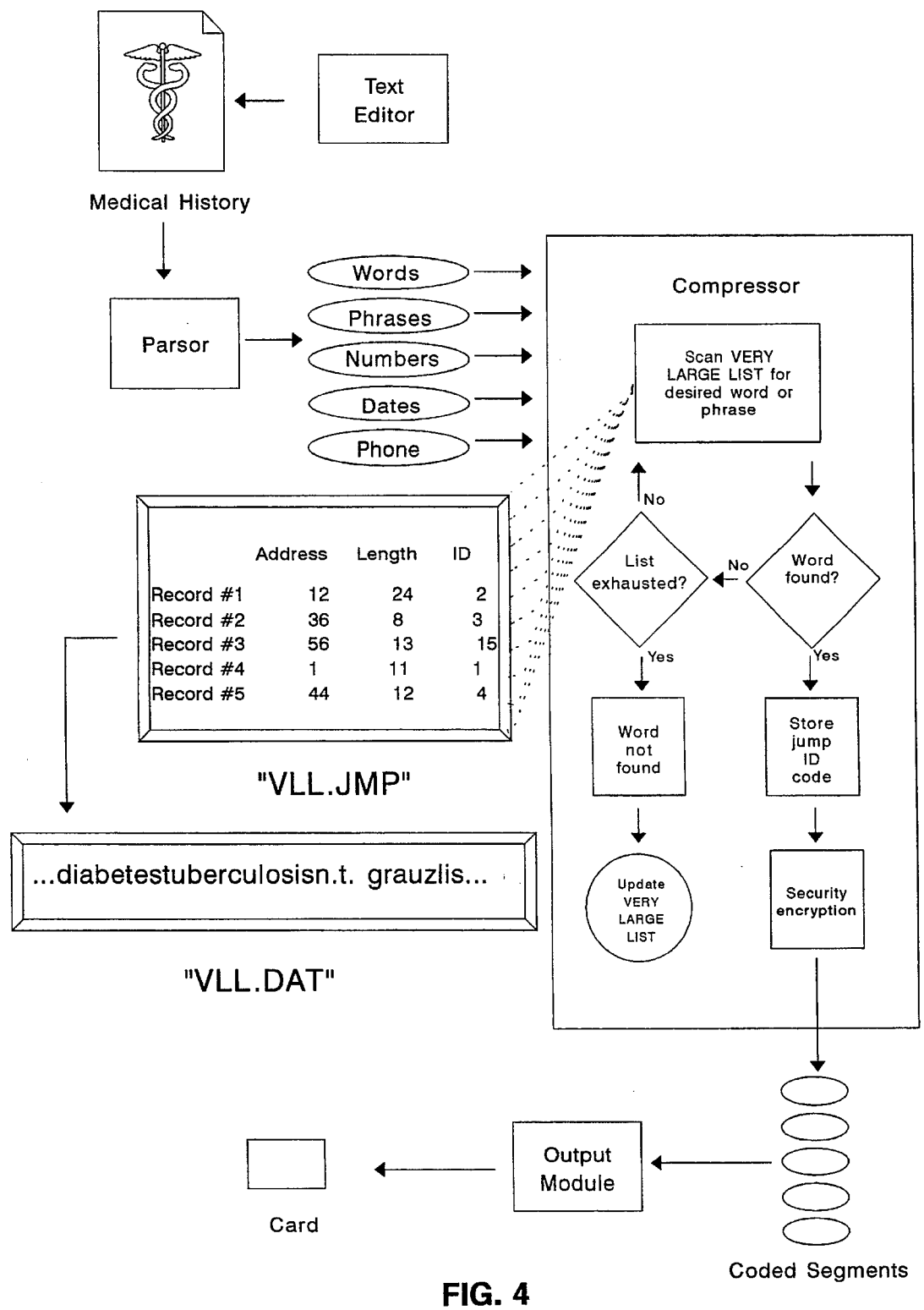
FIG. 4 illustrates the word compression technique of the instant invention.
Figure 5:
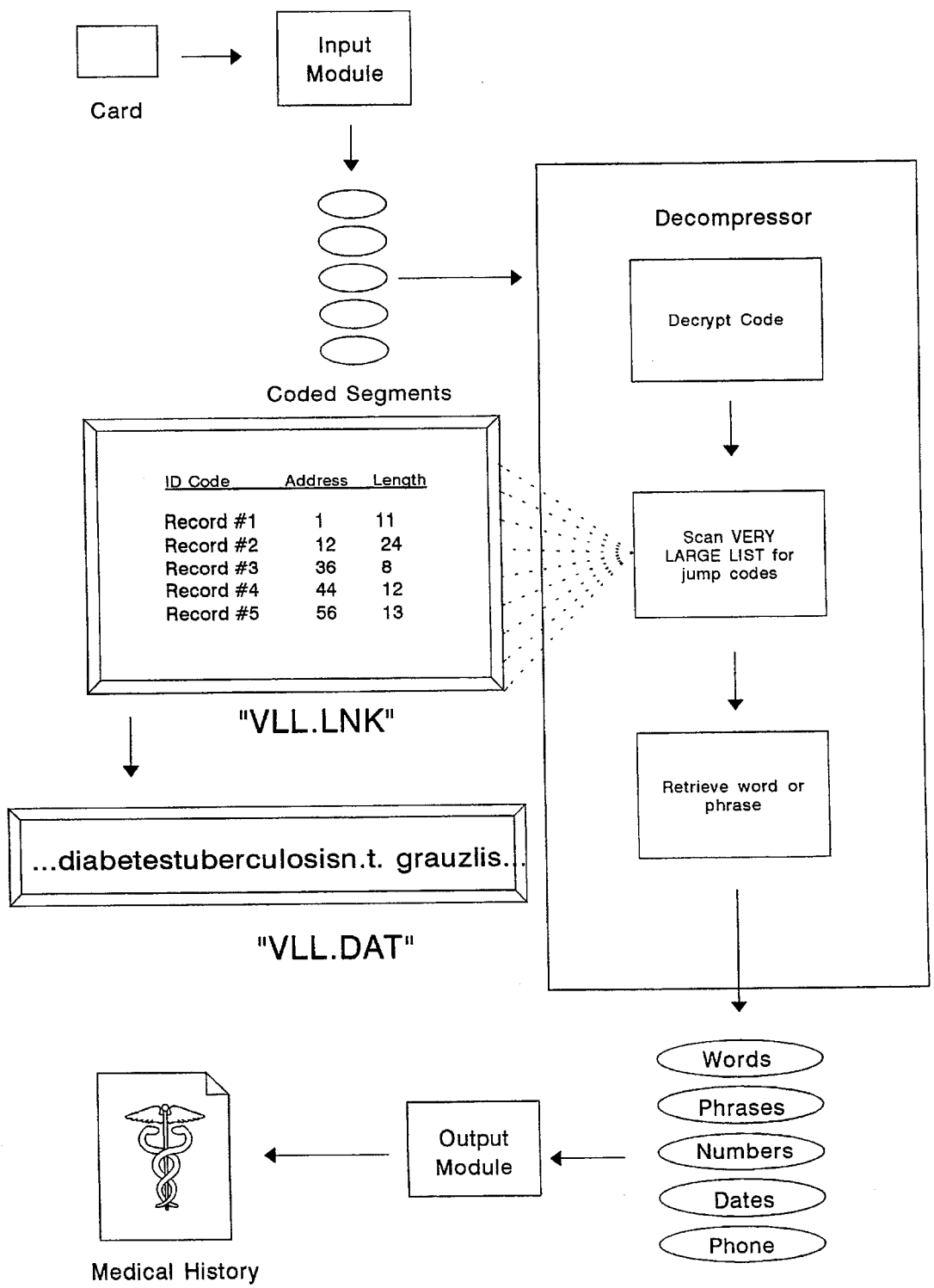
FIG. 5 illustrates the word decompression technique of the instant invention.

Applications:

MedLynxTM, as described herein, is a portable medical information storage and retrieval system for compressing and decompressing information. The MedLynxTM system relies on large, modifiable databases to achieve information compression. This is termed the "Very Large List" or "VLL" concept. In the prototype model, we have used three interrelated VLL files. Knowledge about the contents of these files and the special relationship between these files is vital for a complete understanding of how the system operates. As an overview, the architecture of these files will be discussed and a miniaturized "VLL" environment will be created to illustrate these concepts. An overview schematic is shown in FIGS.4 and 5.

VLL.DAT DICTIONARY:

This is a very large list of words and phrases which serves as the primary "dictionary" used when information is compressed or decompressed. The list is composed of words such as the words in the English language, the words from a medical dictionary, lists of diagnosis, surgical terms, names of medications, names of physicians and medical centers, etc. If one was to directly scan this file, as an example, one may find: stethoscopecongestive heart failurediabetestuberculosisn.t. grauzlis . . .

The following are notable features of this example: i) The words appear to "run into" each other. There are no spaces separating the entries; ii) spaces are permitted within phrases such as "congestive heart failure" and iii) the words are not arranged in any particular order, i.e., the listing is not alphabetical. Locating a particular word or phrase in such a large file may seem difficult. It is difficult to know where a word starts and ends, and where in the file to start looking for a particular word. Sequentially scanning the file from the beginning to end would be a time consuming task, especially if the list contains hundreds of thousands of words. These problems are solved by using the two other associated dictionary files.

VLL.JMP DICTIONARY:

This dictionary forms the secondary dictionary in the compression protocol. Unlike the VLL.DAT based dictionary file which contains words and phrases in no specific format, all the entries in the VLL.JMP dictionary file follow a predefined structure. Each entry in the VLL.JMP file has a record structure. Each record contains three components: i) The starting address of a word, ii) the length of the word, and iii) the unique identification number or the jump vector that is assigned to the word. Although these numbers are found in the VLL.JMP dictionary file, they refer to words that are found in the VLL.DAT primary dictionary file. A sampling of the VLL.JMP dictionary file may look like:

|  | Starting Address | Length | ID Number |
| --- | --- | --- | --- |
| Record #1 | 12 | 24 | 2 |
| Record #2 | 36 | 8 | 3 |
| Record #3 | 56 | 13 | 5 |
| Record #4 | 1 | 11 | 1 |
| Record #5 | 44 | 12 | 4 |

These variables are each exactly three characters long (they are stored as base-256 integers). This means that each record is exactly nine characters long. This fixed structure allows us to extrapolate the starting position of any record within the VLL.JMP file. The first record in this file gives a starting address of 12, a word length of 24 and an ID number of two. Using this information, we can scan the original VLL.DAT dictionary file. We start reading this file at the 12th character (starts with "c"). We will read a word that is 24 characters in length ("congestive heart failure"). This phrase is identified by the jump vector "2." This jump vector can be used to retrieve the phrase "congestive heart failure."

All the records in the VLL.JMP dictionary file and use the pointer information to recover words from the VLL.DAT file. The records in the VLL.JMP dictionary file are arranged in a very specific order. The records refer to words in the VLL.DAT file in an alphabetical fashion. The Record #1 is the first word in the dictionary, Record #2 is the second, and so on. If the word "stethoscope" in VLL.DAT, the beginning is chosen by first reading the VLL.JMP file somewhere in the middle. Record #3 of VLL.JMP refers to the name "N. T. Grauzlis ." Since this word is lower in the alphabet, scanning of a higher record number is required. Record #4 points to the desired word and a match is made, also notable, the jump vector "1" is assigned to "stethoscope." To compress the word stethoscope, the jump vector can be used as its new designation. The jump vectors are always numbers and can range from 1 to n, where n is the maximum number of words in the dictionary. The jump vector can be further compressed by changing the number to a base higher than ten. Base-62 is a convenient base to use because it can be represented by the alphanumeric characters. The resulting string can be encrypted and exported for the user in many different forms. In its simplest form, it can be printed into a card. Alternatively, the output can be converted into bar codes or magnetic signals.

VLL.LNK DICTIONARY:

This dictionary forms the secondary dictionary in the decompression protocol. VLL.LNK is another dictionary file which is used to retrieve the original word or phrase using the jump vector. This list is similar to the VLL.JMP dictionary file in that it is also very structured with well defined records as in the following example:

|  | Starting Address | Length |
|---|---|---|
| Record #1 | 1 | 11 |
| Record #2 | 12 | 24 |
| Record #3 | 36 | 8 |
| Record #4 | 44 | 12 |
| Record #5 | 56 | 13 |

In order to decompress a word or a phrase, it is first necessary to decrypt the string and re-convert it to a base-10 integer. The jump address that is recovered refers to the Record Number in the VLL.LNK file. For example, the jump code "1" refers to the Record #1. This record points to a word that begins at the first character position and is 11 characters long in VLL.DAT dictionary file The jump code "1," thus results in word "stethoscope" being retrieved from the dictionary.

This technique offers the added capability of being able to expand the primary dictionary and secondary dictionaries without jeopardizing the codes which were generated with an older version dictionary. This is termed vertical integration. As an example, assume a new word is to be added such as the word "apple" to the Very Large Lists. The new VLL.DAT dictionary file would read: stethoscopecongestive heart failurediabetestuberculosisn.t. grauzlisapple . . . The modified VLL.JMP dictionary file would read:

|  | Starting Address | Length | ID Number |
|---|---|---|---|
| Record #1 | 69 | 5 | 6 |
| Record #2 | 12 | 24 | 2 |
| Record #3 | 36 | 8 | 3 |
| Record #4 | 56 | 13 | 5 |
| Record #5 | 1 | 11 | 1 |
| record #6 | 44 | 12 | 4 |

And the VLL.LNK dictionary file would read:

|  | Starting Address | Length |
|---|---|---|
| Record #1 | 1 | 11 |
| Record #2 | 12 | 24 |
| Record #3 | 36 | 8 |
| Record #4 | 44 | 12 |
| Record #5 | 56 | 13 |
| record #6 | 69 | 5 |

This new entry is appended to the VLL.DAT and VLL.LNK dictionary files, but it is inserted into the VLL.JMP dictionary file in an alphabetical order. All the old codes remain valid. The Very Large List concept is a new approach to data compression which allows for data compression to play a role in a greater number of everyday applications. The special relationship between the three VLL files allows for capabilities which could not be realized by a simple dictionary model. Dates are converted into absolute numbers of days from a fixed reference date such as Jan. 1, 1889. This absolute number is converted to a high-based number system to compress it into a smaller size. The same is done with telephone numbers and other large numbers.

DATA SECURITY:

The privacy of information generated by the MedLynxTM environment is protected at many different levels. This insures the user that the confidential information will remain protected even if compressed information on a card is stolen or lost. At the simplest level, the compression and decompression algorithms employ a password gateway to identify authorized users. This restricts access to the computer system and prevents unauthorized users from freely viewing or modifying any of the compressed information. This is very basic security measure that can be used in the invention. Moreover, all data stored by the MedLynxTM to a medium is stored anonymously. The compressed data is simply printed or transmitted without any identifying information encoded in the matrix. The identification is via a human-readable marker on the final medium, i.e. the patient name is printed on the portable medical information card. Without actual possession of the storage medium, the electronic information remains completely anonymous. If this data is stolen from a computer memory during processing or transmission, it will not jeopardize the privacy of the final end-user. Additionally, since the raw data on a card shown in FIG. 2 compressed, the data is secure without knowledge of a key code and the appropriate software and hardware systems.

The invention uses an additional measure of security of data encryption and decryption at the time of compression and decompression information processing. The user has a "key code" which is integrated with the encoding process of the data information. This same key code must be used when decompression occurs of this same data. The key code is only known to the patient or others with this information. Variations of this concept allow the user of the card to assign multiple levels of authorization which would allow access to differing levels of information for extraction from the storage media.

The encryption utility of MedLynxTM links the key code to the compressed data by one or more mathematical manipulations which are part of the of this utility. The following is an example of the encryption process using a key code. However, there are voluminous other encryption techniques that can be used to maintain confidentiality of the data.

Example:

The compressed data is represented by strings of characters. In the specific example given in FIG. 2, the compressed information is in the order of 560 character matrix. Once a user selects a key code, the key code string is examined by the encryption security software. The key code string is used to derive a unique integer from 0–255 which serves as an OFFSET value. This is the pointer location where the compressed information begins in the 560 character data matrix. Without the correct key code, the starting location of the data remains unknown and the card cannot be read correctly.

A second manipulation involves looking specifically at the last character in the key code string chosen by the user. The ASCII value for this character is used to determine a SHIFT factor. The SHIFT factor is a number between 1–62 which is used to scramble the compressed data. If the SHIFT value of the key code string is equal to 1, the coded string "Ab1" would be transformed to "Bc2." The latter data string cannot be used to retrieve information with the decompression algorithm without the original key code string necessary to undo the encryption process.

BEST MODE

Figure 6:
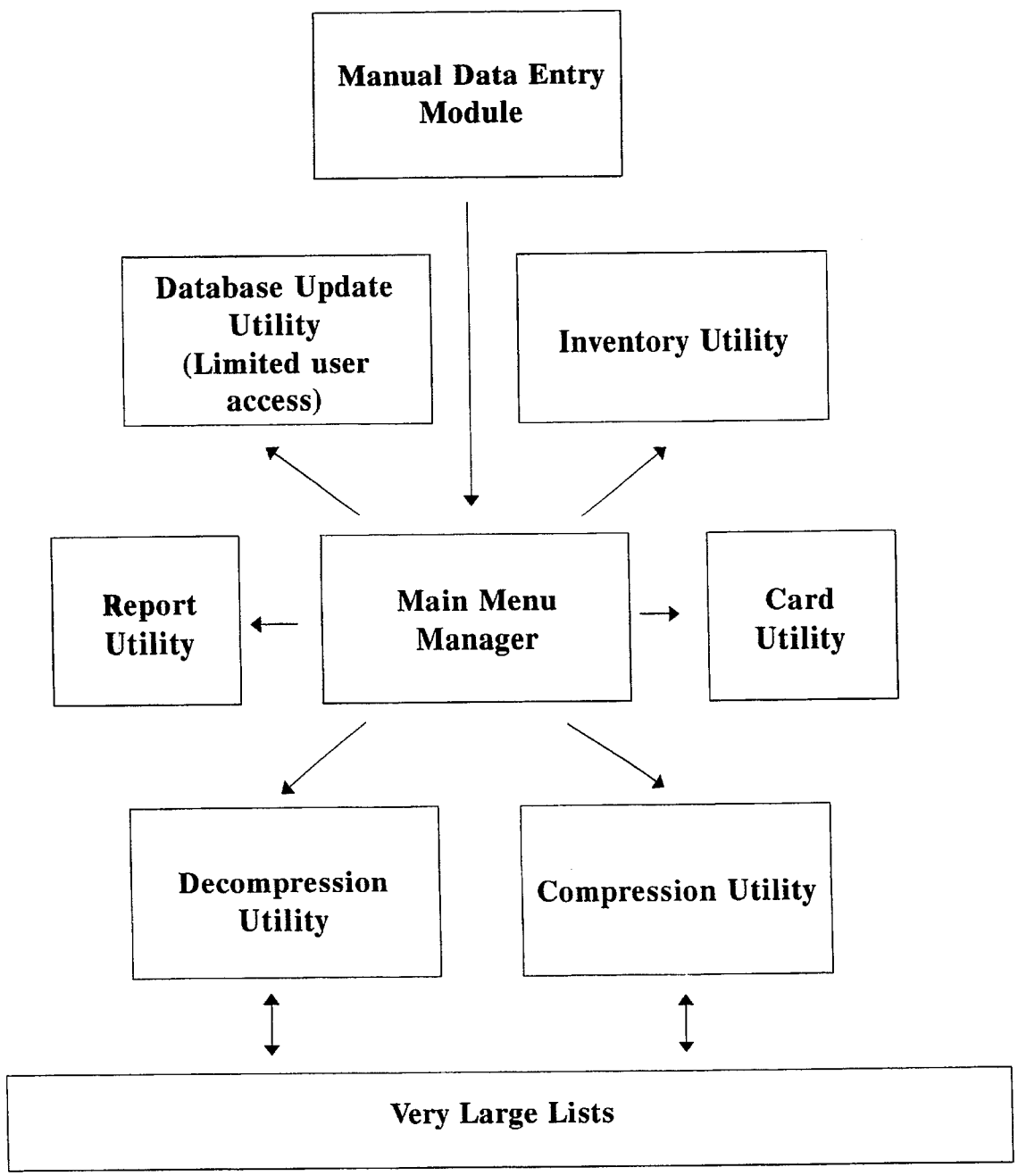
FIG. 6 illustrates an overview of the MedLynxTM software utility to implement the records as shown in FIG. 3.

The MedLynxTM system involves smaller programs and algorithms that are necessary to integrate the various facets of this system. The compression engine uses different techniques for compressing different types of data. Words and phrases can be compressed as discussed above. The output is always encrypted by a user-defined cipher before being printed or saved to disk. The Appendix attached and illustrated in FIG. 6 are as follows:

Main Menu Module:

This module serves as the user-interface which integrates all the modules of MedLynxTM system. The main menu allows the operator to interact with the various modules including the manual data entry module, inventory utility, the card and report utilities, the compression and decompression utilities and the database update utility.

Manual Data Entry Module:

This module is customized to retrieve compressed information from the media of choice such as bar coded cards, optical character reading devices, magnetic strips, Smart-Cards with an output/input means. Once the data is retrieved, two checksum algorithms are used to verify correct data retrieval has occurred which is critical for a medical application as discussed above. If either checksum fails, the data recovery process is stopped here and the information has to be re-read into the computer. This system can incorporate any number of checksum algorithms at this point and is only limited by the data-carrying capacity of the storage medium.

Decompression Utility:

This utility performs two simultaneous functions: i) correct decryption of compressed bundles of information, and ii) correct decompression of information into its original human-readable format. Encryption of encoded information requires appropriate operator authorization and the correct cipher selected by the owner of the information. Correct decompression makes use of the Very Large Lists concept. This utility has a sophisticated algorithm which detects format of incoming data, i.e., words, phrases, numbers, dates, phone number, and executes the appropriate decompression routine to retrieve the original data.

Compression Utility:

This utility also performs two simultaneous functions: i) Correct compression of information and ii) correct encryption of information into encoded bundles. Again, appropriate user authorization is required to operate this software. This sophisticated utility parses incoming information into words, phrases, numbers, dates, and phone numbers and executes the appropriate algorithm to compress the data using the Very Large List concept.

Inventory Utility:

This utility allows the operator to view the decrypted, decompressed information. This utility provides many options for modifying or deleting information. The final product can be re-compressed using the compression utility. This utility also allows the operator to view the first four letters of the card owner's mother's maiden name as an example for access to the medical information. This information is useful in two ways by: i) providing an extra level in security to help insure the identity of the owner of the card, and ii) serving as another check-point to insure that the decompression and decryption systems have operated correctly.

Report Utility:

This utility generates a hardcopy of the decompressed information. The report may also remain in its digital format and be piped to other electronic applications.

Card Utility:

This utility generates compressed output and stores this onto the final medium, i.e. a card. This compressed product allows for more efficient transmission or storage of the original information.

Database Management Utility:

This special utility is reserved for updating or modifying information in the Very Large Lists. Information in these lists can be modified without jeopardizing the ability to material previously compressed using an older system.

Although the description above contains many specificities, these should not be construed as limiting the scope of this invention as set forth in the appended claims, but as merely providing illustration of the presently preferred embodiment of this invention.

Appendix of Computer Listing: Appendix Pages 1–60.

MedLynx Source Code Listing

Manual Data Entry Module

Filename: MANUAL.BAS

```
10 '            Manual Data Entry Module
20 '                V.1.0
30 'Created by
40 'S.Behram
50 'N.Grauzlis
60 'SWJoseph
65 DIM A$(14)
66 MODE=0
67 IF MODE=1 THEN OPEN "r",#3,"update.inf",1
68 IF MODE=1 THEN FIELD #3,1 AS INF$
69 OPEN "o",#4,"card.out"
70 GOSUB 1000:'Screen
80 X=14:Y=6
90 K=11
100 GOSUB  4000
110 IF Y>6 AND  HOLD$="IRETURN" THEN Y=Y-1:LOCATE Y,14:PRINT"
":LOCATE Y,57:PRINT" ":LOCATE Y,60:PRINT" ":GOTO 100
120 IF Y=6 AND HOLD$="IRETURN" THEN BEEP:CLS:RUN "menu"
130 A$(Y-5)=HOLD$
131 REM
132 H=0:V=0:COLOR 19:LOCATE Y,57:PRINT"--":LOCATE Y,60:PRINT"--"
133 FOR I=1 TO 40
134    H=H+ASC(MID$(HOLD$,I,1))*I
135    V=V+ASC(MID$(HOLD$,I,1))*(Y-4)
136 NEXT I
137 IF H>99 THEN H=H-99:GOTO 137
138 IF V>99 THEN V=V-99:GOTO 138
139 COLOR 3:LOCATE Y,57:PRINT USING "##";H:LOCATE Y,60:PRINT USING "##";V
140 Y=Y+1
141 PRINT #4,HOLD$;" ";:PRINT #4,USING "##";H;:PRINT #4," ";:PRINT #4,USING "##";V
150 IF Y<20 THEN 100
151 COLOR 19
152 LOCATE 22,25
153 PRINT "Data conversion in progress."
155 OPEN "r",#1,"decimal.dat",8
160 FIELD #1,8 AS DECIMAL$
170 FOR II=1 TO 14
180    FOR TT=1 TO 40
190       B62$=MID$(A$(II),TT,1)
200       GOSUB 9000
210       LSET DECIMAL$=MKD$(DECIMAL#)
220       DECCNT=DECCNT+1
230       PUT #1,DECCNT
240    NEXT TT
250 NEXT II
```

```
260 CLOSE #1
270 CLS
271 COLOR 15
280 RUN "menu"
999 GOTO 999
1000 REM Screen
1001 CLS: COLOR 7, 0: PRINT "          ";
1002 COLOR 14, 0: PRINT "     Manual Data Entry Module";
1003 COLOR 7, 0: PRINT "         ";
1004 COLOR 9, 0: PRINT "Enter data exactly as it appears on the card, including the upper & lower case";
1005 COLOR 7, 0: PRINT " ";: COLOR 9, 0: PRINT "   characters.  Check the checksum values on the right to validate data.";
1006 COLOR 7, 0: PRINT "   ";: COLOR 9, 0: PRINT " ";
1007 PRINT "              ";: COLOR 3, 0: PRINT "   ";
1008 COLOR 9, 0: PRINT "                    ";
1009 COLOR 7, 0: PRINT " ";: PRINT "        +";
1010 COLOR 3, 0: PRINT "Data";: COLOR 7, 0: PRINT "-----------------------------------+ +";
1011 COLOR 3, 0: PRINT "H";: COLOR 7, 0: PRINT "--";
1012 COLOR 3, 0: PRINT "V";: COLOR 7, 0: PRINT "-+         ";
1013 PRINT "     |            ";
1014 COLOR 8, 0: PRINT "|";: COLOR 7, 0: PRINT " | ";
1015 COLOR 8, 0: PRINT "|";: COLOR 7, 0: PRINT " ";
1016 COLOR 8, 0: PRINT "|";: COLOR 7, 0: PRINT "          ";
1017 PRINT "     |            ";
1018 COLOR 8, 0: PRINT "|";: COLOR 7, 0: PRINT " | ";
1019 COLOR 8, 0: PRINT "|";: COLOR 7, 0: PRINT " ";
1020 COLOR 8, 0: PRINT "|";: COLOR 7, 0: PRINT "          ";
1021 PRINT "     |            ";
1022 COLOR 8, 0: PRINT "|";: COLOR 7, 0: PRINT " | ";
1023 COLOR 8, 0: PRINT "|";: COLOR 7, 0: PRINT " ";
1024 COLOR 8, 0: PRINT "|";: COLOR 7, 0: PRINT "          ";
1025 PRINT "     |            ";
1026 COLOR 8, 0: PRINT "|";: COLOR 7, 0: PRINT " | ";
1027 COLOR 8, 0: PRINT "|";: COLOR 7, 0: PRINT " ";
1028 COLOR 8, 0: PRINT "|";: COLOR 7, 0: PRINT "          ";
1029 PRINT "     |            ";
1030 COLOR 8, 0: PRINT "|";: COLOR 7, 0: PRINT " | ";
1031 COLOR 8, 0: PRINT "|";: COLOR 7, 0: PRINT " ";
1032 COLOR 8, 0: PRINT "|";: COLOR 7, 0: PRINT "          ";
1033 PRINT "     |            ";
1034 COLOR 8, 0: PRINT "|";: COLOR 7, 0: PRINT " | ";
1035 COLOR 8, 0: PRINT "|";: COLOR 7, 0: PRINT " ";
1036 COLOR 8, 0: PRINT "|";: COLOR 7, 0: PRINT "          ";
1037 PRINT "     |            ";
1038 COLOR 8, 0: PRINT "|";: COLOR 7, 0: PRINT " | ";
1039 COLOR 8, 0: PRINT "|";: COLOR 7, 0: PRINT " ";
1040 COLOR 8, 0: PRINT "|";: COLOR 7, 0: PRINT "          ";
1041 PRINT "     |            ";
1042 COLOR 8, 0: PRINT "|";: COLOR 7, 0: PRINT " | ";
1043 COLOR 8, 0: PRINT "|";: COLOR 7, 0: PRINT " ";
1044 COLOR 8, 0: PRINT "|";: COLOR 7, 0: PRINT "          ";
1045 PRINT "     |            ";
1046 COLOR 8, 0: PRINT "|";: COLOR 7, 0: PRINT " | ";
```

```
1047 COLOR 8, 0: PRINT "|";: COLOR 7, 0: PRINT " ";
1048 COLOR 8, 0: PRINT "|";: COLOR 7, 0: PRINT "                    ";
1049 PRINT "           |                      ";
1050 COLOR 8, 0: PRINT "|";: COLOR 7, 0: PRINT " |  ";
1051 COLOR 8, 0: PRINT "|";: COLOR 7, 0: PRINT "  ";
1052 COLOR 8, 0: PRINT "|";: COLOR 7, 0: PRINT "                    ";
1053 PRINT "           |                      ";
1054 COLOR 8, 0: PRINT "|";: COLOR 7, 0: PRINT " |  ";
1055 COLOR 8, 0: PRINT "|";: COLOR 7, 0: PRINT "  ";
1056 COLOR 8, 0: PRINT "|";: COLOR 7, 0: PRINT "                    ";
1057 PRINT "           |                      ";
1058 COLOR 8, 0: PRINT "|";: COLOR 7, 0: PRINT " |  ";
1059 COLOR 8, 0: PRINT "|";: COLOR 7, 0: PRINT "  ";
1060 COLOR 8, 0: PRINT "|";: COLOR 7, 0: PRINT "                    ";
1061 PRINT "           |                      ";
1062 COLOR 8, 0: PRINT "|";: COLOR 7, 0: PRINT " |  ";
1063 COLOR 8, 0: PRINT "|";: COLOR 7, 0: PRINT "  ";
1064 COLOR 8, 0: PRINT "|";: COLOR 7, 0: PRINT "                    ";
1065 PRINT "           |                      ";
1066 COLOR 8, 0: PRINT "|";: COLOR 7, 0: PRINT " |  ";
1067 COLOR 8, 0: PRINT "|";: COLOR 7, 0: PRINT "  ";
1068 COLOR 8, 0: PRINT "|";: COLOR 7, 0: PRINT "                    ";
1069 PRINT "           ";: COLOR 8, 0: PRINT "+----------------------------------------+";
1070 COLOR 7, 0: PRINT " ";: COLOR 8, 0: PRINT "+-----+";
1071 COLOR 7, 0: PRINT "                 ";: PRINT "                                            ";
1072 COLOR 8, 0: PRINT " ";: COLOR 7, 0: PRINT "                    ";
1073 PRINT "                                            ";
1074 KEY OFF
1077 COLOR 7, 0
1100 RETURN
4000 REM Advanced data entry read/write module
4001 REM Requires x,y and k for color
4002 REM Stores string in HOLD$
4020 XO=0:YO=0:HOLD$=""
4021 CURSOR$(1)=CHR$(221)
4022 CURSOR$(2)=CHR$(223)
4023 CURSOR$(3)=CHR$(222)
4024 CURSOR$(4)=CHR$(220)
4030 I$=INKEY$
4040 CUR=CUR+.1 :IF CUR>4 THEN CUR=1
4050 LOCATE Y+YO,X+XO
4051 PRINT CURSOR$(INT(CUR+.5))
4060 IF I$="" AND MODE=0 THEN 4030
4061 IF MODE=1 THEN GOSUB 6000
4065 LOCATE Y+YO,X+XO
4066 PRINT " "
4070 IF ASC(I$)=8 THEN GOSUB 4500
4071 IF HOLD$="!RETURN" THEN RETURN
4080 IF ASC(I$)=13 THEN 4130
4081 IF (I$>="a" AND I$<="z") OR (I$>="A" AND I$<="Z") OR (I$>="0" AND I$<="9") THEN 4085
4082 GOTO 4030
4085 XO=XO+1
4086 HOLD$=HOLD$+I$
```

```
4090 COLOR K
4100 LOCATE Y+YO,X+XO-1
4110 PRINT I$
4120 IF X+XO<40+X THEN 4030
4130 HOLD$=RIGHT$(HOLD$,XO)
4140 RETURN
4500 IF XO>0 THEN XO=XO-1:HOLD$=LEFT$(HOLD$,LEN(HOLD$)-1):RETURN
4510 HOLD$="!RETURN"
4520 RETURN
6000 REM INput from datafile
6010 REM
6020 REM
6030 YU=YU+1
6040 GET #3,YU
6050 I$=INF$
6060 RETURN
9000 REM This utility converts base62 --> decimal
9010 REM Requires string stored in B62$
9020 REM Ouput stored in        DECIMAL#
9030 DECIMAL#=0:REM UMCP
9040 D=LEN(B62$)
9050 FOR I=D TO 1 STEP -1
9060     C$=MID$(B62$,I,1)
9070     IF C$>="A" AND C$<="Z" THEN C=ASC(C$)-65
9080     IF C$>="a" AND C$<="z" THEN C=26+ASC(C$)-97
9090     IF C$>="0" AND C$<="9" THEN C=52+ASC(C$)-ASC("0")
9100     DECIMAL#=DECIMAL#+C*(62^(D-I))
9110 NEXT I
9120 RETURN
```

Warning Screen and Database Update Utility
Filenames: WARNING.BAS and DATAFIX.BAS

```
10 'Database Management Utility ----->WARNING SCREEN!!!
20 'Warns user of database modifications, then loads file DATAFIX.BAS
30 '
40 '
50 'Created by S. Behram & N. Grauzlis & S.W. Joseph 10.16.93
60 '
70 '
80 CLS
90 KEY OFF
100 CLS: COLOR 3, 0: PRINT "               ";
110 COLOR 14, 0: PRINT "    Database Management Utility";
120 COLOR 3, 0: PRINT "              ";
130 PRINT "                                        ";
140 PRINT "                                        ";
150 PRINT " ";: COLOR 1, 0: PRINT
"Warning!Warning!Warning!Warning!Warning!Warning!Warning!Warning!Warning!";
160 COLOR 3, 0: PRINT "    ";: PRINT " ";: COLOR 7, 0: PRINT "+---------------------------------
-----------------------------------";
170 COLOR 8, 0: PRINT "+";: COLOR 3, 0: PRINT "  ";
180 PRINT " ";: COLOR 7, 0: PRINT "¦";: COLOR 3, 0: PRINT " ";
```

```
190 COLOR 28, 0: PRINT "                                                              ";
200 COLOR 3, 0: PRINT " ";: COLOR 8, 0: PRINT "◻";
210 COLOR 3, 0: PRINT "  ";: PRINT " ";: COLOR 7, 0: PRINT "◻";
220 COLOR 3, 0: PRINT " ";: COLOR 28, 0: PRINT "  ◻◻  ◻◻           ◻◻        ◻◻
";
230 COLOR 3, 0: PRINT " ";: COLOR 8, 0: PRINT "◻";
240 COLOR 3, 0: PRINT "  ";: PRINT " ";: COLOR 7, 0: PRINT "◻";
250 COLOR 3, 0: PRINT " ";: COLOR 28, 0: PRINT "  ◻◻  ◻◻
";
260 COLOR 3, 0: PRINT " ";: COLOR 8, 0: PRINT "◻";
270 COLOR 3, 0: PRINT "  ";: PRINT " ";: COLOR 7, 0: PRINT "◻";
280 COLOR 3, 0: PRINT " ";: COLOR 28, 0: PRINT "  ◻◻  ◻◻ ◻◻◻◻  ◻◻ ◻◻◻  ◻◻◻◻◻
◻◻◻  ◻◻◻◻◻  ◻◻◻  ◻◻◻◻◻  ◻◻◻ ◻◻ ";
290 COLOR 3, 0: PRINT " ";: COLOR 8, 0: PRINT "◻";
300 COLOR 3, 0: PRINT "  ";: PRINT " ";: COLOR 7, 0: PRINT "◻";
310 COLOR 3, 0: PRINT " ";: COLOR 28, 0: PRINT "  ◻◻ ◻ ◻◻   ◻◻  ◻◻◻ ◻◻ ◻◻  ◻◻  ◻◻
◻◻ ◻◻  ◻◻  ◻◻ ◻◻ ◻◻  ◻◻   ";
320 COLOR 3, 0: PRINT " ";: COLOR 8, 0: PRINT "◻";
330 COLOR 3, 0: PRINT "  ";: PRINT " ";: COLOR 7, 0: PRINT "◻";
340 COLOR 3, 0: PRINT " ";: COLOR 28, 0: PRINT "  ◻◻◻◻◻◻◻  ◻◻◻◻◻  ◻◻  ◻◻ ◻◻  ◻◻
◻◻  ◻◻ ◻◻   ◻◻  ◻◻  ◻◻ ◻◻  ◻◻   ";
350 COLOR 3, 0: PRINT " ";: COLOR 8, 0: PRINT "◻";
360 COLOR 3, 0: PRINT "  ";: PRINT " ";: COLOR 7, 0: PRINT "◻";
370 COLOR 3, 0: PRINT " ";: COLOR 28, 0: PRINT "  ◻◻◻ ◻◻◻ ◻◻  ◻◻   ◻◻   ◻◻ ◻◻  ◻◻
◻◻ ◻◻   ◻◻   ◻◻  ◻◻  ◻◻◻◻◻   ";
380 COLOR 3, 0: PRINT " ";: COLOR 8, 0: PRINT "◻";
390 COLOR 3, 0: PRINT "  ";: PRINT " ";: COLOR 7, 0: PRINT "◻";
400 COLOR 3, 0: PRINT " ";: COLOR 28, 0: PRINT "  ◻◻  ◻◻ ◻◻◻ ◻◻ ◻◻◻◻   ◻◻  ◻◻
◻◻◻◻ ◻◻  ◻◻  ◻◻◻◻ ◻◻  ◻◻    ◻◻    ";
410 COLOR 3, 0: PRINT " ";: COLOR 8, 0: PRINT "◻";
420 COLOR 3, 0: PRINT "  ";: PRINT " ";: COLOR 7, 0: PRINT "◻";
430 COLOR 3, 0: PRINT " ";: COLOR 28, 0: PRINT "
◻◻◻◻◻   ";
440 COLOR 3, 0: PRINT " ";: COLOR 8, 0: PRINT "◻";
450 COLOR 3, 0: PRINT "  ";: PRINT " ";: COLOR 7, 0: PRINT "◻";
460 COLOR 3, 0: PRINT " ";: COLOR 28, 0: PRINT "
";
470 COLOR 3, 0: PRINT " ";: COLOR 8, 0: PRINT "◻";
480 COLOR 3, 0: PRINT "  ";: PRINT " ";: COLOR 7, 0: PRINT "+";
490 COLOR 8, 0: PRINT "------------------------------------------------------------------
+";
500 COLOR 3, 0: PRINT "  ";: PRINT "  ";: COLOR 1, 0: PRINT
"Warning!Warning!Warning!Warning!Warning!Warning!Warning!Warning!";
510 COLOR 3, 0: PRINT "    ";: PRINT "                                                  ";
520 PRINT " Note: This program will modify your database. It is intended to be used only";
530 PRINT "      for updating the database in conjunction with the update disk.      ";
540 PRINT "                                                                            ";
550 COLOR 28, 0: PRINT "     ";: COLOR 11, 0: PRINT "Are you sure you want to use the
Database Management Utility?";
560 COLOR 28, 0: PRINT " ";: COLOR 14, 0: PRINT "  ";
570 COLOR 28, 0: PRINT "       ";: COLOR 3, 0: PRINT "
";
580 COLOR 7, 0
590 X=72:Y=22:K=3
```

```
591 COLOR 13
600 GOSUB 4000
610 IF HOLD$<>"yes" AND HOLD$<>"YES" AND HOLD$<>"Y" AND HOLD$<>"y" AND
HOLD$<>"Yes" THEN END
999 RUN "datafix.bas"
4000 REM Advanced data entry read/write module
4001 REM Requires x,y and k for color
4002 REM Stores string in HOLD$
4020 XO=0:YO=0:HOLD$=""
4021 CURSOR$(1)=CHR$(221)
4022 CURSOR$(2)=CHR$(223)
4023 CURSOR$(3)=CHR$(222)
4024 CURSOR$(4)=CHR$(220)
4030 I$=INKEY$
4040 CUR=CUR+.1 :IF CUR>4 THEN CUR=1
4050 LOCATE Y+YO,X+XO
4051 PRINT CURSOR$(INT(CUR+.5))
4060 IF I$="" THEN 4030
4065 LOCATE Y+YO,X+XO
4066 PRINT " "
4070 IF ASC(I$)=8 AND XO>0 THEN XO=XO-1:HOLD$=LEFT$(HOLD$,LEN(HOLD$)-1):GOTO 4030
4080 IF ASC(I$)=13 THEN 4130
4081 XO=XO+1
4082 HOLD$=HOLD$+I$
4090 COLOR K
4100 LOCATE Y+YO,X+XO-1
4110 PRINT I$
4120 GOTO 4030
4130 HOLD$=RIGHT$(HOLD$,XO)
4140 RETURN 10 '              Database Management Utility
20 '                   V.1.01
30 '
40 'S.Behram & N.Grauzlis
50 'October 16, 1993
60 '
70 'WARNING:  This program will modify the VLL.JMP and VLL.DAT files.
80 '       This utility must be used in conjunction w/ update disk.
90 '
100 GOSUB 1000:'Screen display
110 'MODE allows for special keyboard entry if equal to one.
120 'This feature will be removed after program development and users
130 'can modify VLL files only via the update disk.
140 '
150 MODE=1
151 FOR I=1 TO 78
152 BLANK$=BLANK$+" "
153 NEXT I
154 BUG=0
160 IF MODE<>1 THEN GOSUB 3000   :REM Print instructions for disk insertion and pathname
170 OPEN "i",#1,"words.num"
```

```
180 INPUT #1,COUNT
190 CLOSE #1
200 OPEN "r",#1,"vll.imp",9
210 FIELD #1,3 AS SA$,3 AS L$,3 AS ID$
220 OPEN "r",#2,"vll.dat",1
230 FIELD #2,1 AS C$
240 REM
250 REM input
251 GOSUB 3500
260 GOSUB 6000:'Blank top two viewports
261 IF SEARCH$="exit" THEN CLS:run "menu"
270 LOCATE 5,40-LEN(SEARCH$)/2
280 COLOR 3
290 PRINT SEARCH$
295 COLOR 28
296 LOCATE 16,2
297 PRINT CHR$(219)
300 GOSUB 2000
305 COLOR 3
310 FOR I=1 TO 6
320 LOCATE 7+I,40-LEN(FIND$(I))/2
330 PRINT FIND$(I)
340 NEXT I
341 LOCATE 16,2
342 PRINT " "
343 COLOR 11
344 LOCATE 16,17
350 IF MATCH=1 THEN PRINT "Already exists.":FOR I=1 TO 5000:NEXT I:GOTO 240
351 IF MODE<>1 THEN 410
360 PRINT "Are you sure you wish to update (y/n):"
370 X=57:Y=16
375 K=3
380 GOSUB 4000:'Keyboard input
390 GOSUB 4500
400 IF HOLD$<>"y" AND HOLD$<>"yes" THEN 240
410 REM Update Utility -- User wishes to ADD to VLL database
420 COLOR 28
430 LOCATE 19,2
440 PRINT CHR$(219)
450 INSERT=CURR-1
455 CURR=INSERT
460 GOSUB 8000
470 IF ITEM$<SEARCH$ THEN INSERT=INSERT+1:GOTO 455
480 REM INSERT=INSERT-1
481 REM This is a FIX for the period fault.
482 IF SEARCH$="." THEN BEEP:INSERT=1
490 'Alphabetically, the new string should be placed at the location INSERT
495 WORDCNT=WORDCNT+1
500 SA=LOF(2)+1
510 L=LEN(SEARCH$)
520 ID=COUNT+WORDCNT:Z=TIMER
521 FOR I=COUNT+1 TO INSERT+1 STEP -1
522    GET #1,I-1
523    PUT #1,I
```

```
524    IF I/1000=INT(I/1000) AND MODE=1 THEN GOSUB 10000
525 NEXT I
526 IF MODE<>1 THEN GOSUB 15000
530 DECIMAL=SA:GOSUB 5000:LSET SA$=RESULT$
540 DECIMAL=L:GOSUB 5000:LSET L$=RESULT$
550 DECIMAL=ID:GOSUB 5000:LSET ID$=RESULT$
560 PUT #1,INSERT
570 FOR I=1 TO L
580    LSET C$=MID$(SEARCH$,I,1)
590    PUT #2,I+SA-1
600 NEXT I
610 LOCATE 19,2
630 OPEN "o",#3,"words.num"
640 PRINT #3,COUNT+WORDCNT
650 PRINT #3,DATE$
660 PRINT #3,TIME$
670 CLOSE #3
671 OPEN "r",#3,"vll.lnk",6
672 FIELD #3,3 AS SA2$,3 AS L2$
673 LSET SA2$=SA$:LSET L2$=L$
674 PUT #3,ID
675 CLOSE #3
676 PRINT ""
680 GOTO 240
1000 REM Display
1001 CLS: COLOR 14, 0: PRINT "                    Database Management Utility";
1002 COLOR 7, 0: PRINT "                    ";
1003 PRINT "                         ";
1004 PRINT "                         ";
1005 PRINT "+";: COLOR 9, 0: PRINT "Database Search Parameter";
1006 COLOR 7, 0: PRINT "--------------------------------------------------+";
1007 PRINT "░                         ";
1008 COLOR 8, 0: PRINT "░";: PRINT "+-----------------------------------------------------+";
1009 COLOR 7, 0: PRINT "+";: COLOR 9, 0: PRINT "Closest Match";
1010 COLOR 7, 0: PRINT "--------------------------------------------------+";
1011 PRINT "░                         ";
1012 COLOR 8, 0: PRINT "░";: COLOR 7, 0: PRINT "░";
1013 COLOR 9, 0: PRINT "                         ";
1014 COLOR 8, 0: PRINT "░";: COLOR 7, 0: PRINT "░                         ";
1015 COLOR 8, 0: PRINT "░";: COLOR 7, 0: PRINT "░                         ";
1016 COLOR 8, 0: PRINT "░";: COLOR 7, 0: PRINT "░                         ";
1017 COLOR 8, 0: PRINT "░";: COLOR 7, 0: PRINT "░                         ";
1018 COLOR 8, 0: PRINT "░";: PRINT "+-----------------------------------------------------+";
1019 PRINT "+-+";: COLOR 7, 0: PRINT "       +";
1020 COLOR 9, 0: PRINT "Instructions";: COLOR 7, 0: PRINT "-----------------------------------+";
1021 COLOR 8, 0: PRINT "░ ░";: COLOR 7, 0: PRINT " ";
1022 COLOR 8, 0: PRINT "Searching";: COLOR 7, 0: PRINT " ░";
```

```
1023 COLOR 8, 0: PRINT "        ";: COLOR 7, 0: PRINT "                                              ";
1024 COLOR 8, 0: PRINT "¤";: PRINT "+-+";: COLOR 7, 0: PRINT "            ¤";
1025 COLOR 8, 0: PRINT "        ";: COLOR 7, 0: PRINT "                                              ";
1026 COLOR 8, 0: PRINT "¤";: PRINT "+-+";: COLOR 7, 0: PRINT "        ¤";
1027 COLOR 8, 0: PRINT "¤";: PRINT "¤";: COLOR 7, 0: PRINT " ";
1028 COLOR 8, 0: PRINT "¤";: COLOR 7, 0: PRINT " ";
1029 COLOR 8, 0: PRINT "Updating";: COLOR 7, 0: PRINT "  ¤";
1030 COLOR 8, 0: PRINT "¤";: PRINT "+-+";: COLOR 7, 0: PRINT "        ";
1031 COLOR 8, 0: PRINT "+-------------------------------------------------------+";
1032 COLOR 7, 0: PRINT "+";: COLOR 9, 0: PRINT "Time Remaining";
1033 COLOR 7, 0: PRINT "----------------------+                  ";
1034 PRINT "¤            ";: COLOR 8, 0: PRINT " ";
1035 COLOR 7, 0: PRINT "                  ";
1036 COLOR 8, 0: PRINT "¤";: COLOR 7, 0: PRINT "                              ";
1037 COLOR 8, 0: PRINT "+------------------------------------+";
1038 COLOR 7, 0: PRINT "     ";: COLOR 8, 0: PRINT "                    ";
1039 COLOR 7, 0: PRINT "     ";: COLOR 8, 0: PRINT "    V.1.0";
1040 KEY OFF
1041 COLOR 7, 0
1050 RETURN
2000 REM Scan subroutine V.1.0
2010 REM Created by S. Behram on ▆▆▆▆▆▆▆▆
2020 REM
2030 REM Requires incoming search string in SEARCH$
2040 REM Requires the total number of words in entire dbase in COUNT
2050 REM Also needs VLL files to have already been opened and field
2060 REM statements declared:
2070 REM OPEN "R",#1,"vll.jmp",9    FIELD #1,3 as sa$,3 as I$,3 as id$
2080 REM OPEN "R",#2,"vll.dat",1    FIELD #2,1 as c$
2090 REM
2100 REM The STR2DEC subroutine must be install at line 7000
2110 REM Program returns MATCH=1 for positive match
2120 REM Program returns strings FIND(1-6)$ as closest matches
2130 REM Begin dbase search
2140 JMP=INT(COUNT/2+.5):CURR=JMP
2150 REM Retrieve item and current JMP location
2160 GOSUB 8000:'routine to retrieve string at CURR
2250 IF ITEM$=SEARCH$ THEN MATCH=1:GOTO 2330
2260 JMP=INT(JMP/2+.5)
2270 IF JMP<1 THEN JMP=1
2280 IF ITEM$>SEARCH$ THEN CURR=CURR-JMP:IF CURR<1 THEN CURR=1
2290 IF ITEM$<SEARCH$ THEN CURR=CURR+JMP:IF CURR>COUNT+WORDCNT THEN CURR=COUNT+WORDCNT
2300 IF ITEM$=LAST$ THEN MATCH=0:GOTO 2330
2310 LAST$=HOLD$:HOLD$=ITEM$
2320 GOTO 2160
2330 REM Search complete
2340 REM Will store the results of search in find$(1-6)
2350 REM Closest answer is in curr
2360 IF CURR<3 THEN CURR=CURR+1:GOTO 2360
2370 IF CURR>COUNT-3 THEN CURR=CURR-1:GOTO 2370
2380 CR=0:CRR=CURR
```

```
2390 FOR CURR=CURR-2 TO CURR+3
2400   CR=CR+1
2410   GOSUB 8000
2500   FIND$(CR)=ITEM$
2510 NEXT CURR:CURR=CRR
2520 HOLD$=FIND$(1)
2530 FIND$(1)=FIND$(3)
2540 FIND$(3)=HOLD$
2550 RETURN
3000 REM Instructions for disk update
3010 COLOR 11
3020 GOSUB 6500
3030 LOCATE 16,17
3040 PRINT "Please enter pathname for update file (ex: c:\test):"
3050 K=3:X=17:Y=X:GOSUB 4000:GOSUB 4500
3060 IF HOLD$="" OR HOLD$="q" OR HOLD$="quit" OR HOLD$="exit" THEN RUN
3070 IF RIGHT$(HOLD$,1)<>"\" THEN HOLD$=HOLD$+"\"
3080 OPEN "I",#5,HOLD$+"update.dat"
3090 RETURN
3500 REM Input from keyboard.
3505 COLOR 11
3510 GOSUB 6500:'clear the instructions screen
3520 LOCATE 16,17
3530 PRINT "Please enter the data string ('exit' to quit):"
3535 K=3
3536 IF MODE<>1 THEN INPUT #5,HOLD$:IF HOLD$="" THEN STOP ELSE GOTO 3550
3540 X=17:Y=17:GOSUB 4000:'Input string
3550 GOSUB 4500:'Converts to lowercase.
3560 SEARCH$=HOLD$
3570 GOSUB 6500:REM Clear instruction screen
3610 RETURN
4000 REM Advanced data entry read/write module
4001 REM Requires x,y and k for color
4002 REM Stores string in HOLD$
4020 XO=0:YO=0:HOLD$=""
4021 CURSOR$(1)=CHR$(221)
4022 CURSOR$(2)=CHR$(223)
4023 CURSOR$(3)=CHR$(222)
4024 CURSOR$(4)=CHR$(220)
4030 I$=INKEY$
4040 CUR=CUR+.1 :IF CUR>4 THEN CUR=1
4050 LOCATE Y+YO,X+XO
4051 PRINT CURSOR$(INT(CUR+.5))
4060 IF I$="" THEN 4030
4065 LOCATE Y+YO,X+XO
4066 PRINT " "
4070 IF ASC(I$)=8 AND XO>0 THEN XO=XO-1:HOLD$=LEFT$(HOLD$,LEN(HOLD$)-1):GOTO 4030
4080 IF ASC(I$)=13 THEN 4130
4081 XO=XO+1
4082 HOLD$=HOLD$+I$
4090 COLOR K
4100 LOCATE Y+YO,X+XO-1
4110 PRINT I$
```

```
4120 GOTO 4030
4130 HOLD$=RIGHT$(HOLD$,XO)
4140 RETURN
4500 REM Converts to lower case.
4510 REM Requires HOLD$, returns HOLD$
4520 FOR I=1 TO LEN(HOLD$)
4530    IF MID$(HOLD$,I,1)>="A" AND MID$(HOLD$,I,1)<="Z" THEN
MID$(HOLD$,I,1)=CHR$(ASC(MID$(HOLD$,I,1))+32)
4540 NEXT I
4550 RETURN
5000 REM This routine converts a decimal input into a string base 255
5010 REM Requires incoming decimal value in   DECIMAL
5020 REM Returns answer in RESULT$
5030 DIG1=0:DIG2=0:DIG3=0
5040 IF DECIMAL > 255^2 THEN DECIMAL=DECIMAL-256^2:DIG3=DIG3+1:GOTO 5040
5050 IF DECIMAL > 255^1 THEN DECIMAL=DECIMAL-256^1:DIG2=DIG2+1:GOTO 5050
5060 IF DECIMAL >= 255^0 THEN DECIMAL=DECIMAL-256^0:DIG1=DIG1+1:GOTO
5060
5070 RESULT$=CHR$(DIG3)+CHR$(DIG2)+CHR$(DIG1)
5080 RETURN
6000 REM Clean top two viewports
6010 LOCATE 5,2
6020 PRINT BLANK$
6030 FOR I=1 TO 6
6040 LOCATE 7+I,2
6050 PRINT BLANK$
6060 NEXT I
6070 RETURN
6500 REM Clears instruction screen
6510 FOR I=1 TO 4
6520 LOCATE 15+I,17
6530 PRINT "                              "
6540 NEXT I
6550 RETURN
7000 REM This routine converts a string base 255 integer into decimal
7010 REM Requires 255 base integer in RESULT$, returns answer in DECIMAL.
7020 DIG3=ASC(LEFT$(RESULT$,1))
7030 DIG2=ASC(MID$(RESULT$,2,1))
7040 DIG1=ASC(RIGHT$(RESULT$,1))
7050 DECIMAL=DIG3*256^2+DIG2*256^1+DIG1*256^0
7060 RETURN
8000 REM Retrieves string located at CURR.  Returns it in Item$
8010 REM Retrieve item and current JMP location
8020 GET #1,CURR
8030 RESULT$=SA$:GOSUB 7000:SA=DECIMAL
8040 RESULT$=L$:GOSUB 7000:L=DECIMAL
8050 RESULT$=ID$:GOSUB 7000:ID=DECIMAL
8060 ITEM$=""
8080 FOR I=1 TO L
8090    GET #2,I+SA-1
8100    ITEM$=ITEM$+C$
8110 NEXT I
8120 IF BUG=0 THEN 8999
8125 IF SA<10 THEN GOTO 8999:'Rem to close to the end
```

```
8130 REM This is to fix DOS bug
8140 IF (SA-1)/256<>INT((SA-1)/256) THEN 8999
8150 HOLD=CURR:H$=ITEM$
8155 BUG=0
8160 CURR=CURR-1:GOSUB 8000:LOW$=ITEM$
8170 CURR=CURR+2:GOSUB 8000:HIGH$=ITEM$
8171 CURR=HOLD:GOSUB 8000
8180 BUG=1
8190 REM ITEM$=H$:CURR=HOLD
8200 IF ITEM$>LOW$ AND ITEM$<HIGH$ THEN 8999
8210 REM Bug detected.
8220 BEEP
8230 P$=RIGHT$(ITEM$,1):ITEM$=P$+LEFT$(ITEM$,LEN(ITEM$)-1)
8999 RETURN
10000 REM Tracks time remaining
10010 IF MODE=0 THEN FORWARD:REM Disk Input -- Use average times * LOF
10020 ZZ=TIMER
10030 DIF=ZZ-Z
10040 SEC=DIF*(I-INSERT)/(COUNT-I)
10050 HOUR=INT(SEC/60/60):SEC=SEC-HOUR*60*60
10060 MIN=INT(SEC/60):SEC=SEC-MIN*60
10070 SEC=INT(SEC+.5)
10080 COLOR 3
10090 LOCATE 22,4
10100 PRINT HOUR;"Hr. ";MIN;"Min. ";SEC;"Sec.    "
10110 RETURN
15000 REM Tracks time for disk updates
15010 ZZ=TIMER
15020 DIFF=ZZ-Z
15030 UPDCNT=UPDCNT+1
15040 UPDTM=UPDTM+DIFF
15050 AVG=UPDTM/UPDCNT
15060 SEC=AVG*(LOF(5)-UPDCNT+1)
15070 GOSUB 10050
15080 RETURN
```

Inventory Utility

Filename: INVENT.BAS

```
0 REM 13,8
10 REM Inventory Utility for the portable medical info system
20 REM
30 REM 11/1/1993 Created by S. Behram / N. Grauzlis / S. Joseph
40 REM
50 REM
60 CLS:KEY OFF
70 COLOR 25
80 LOCATE 12,36
90 PRINT "Loading..."
100 COLOR 10
101 MAX=560: ' Maximum capacity of media
110 REM Dimension Variables
120 REM
```

```
130 DIM PMH$(50),PMHDATE$(50),PMHCNT$(50),PMHMD$(50)
140 DIM PSH$(50),PSHDATE$(50),PSHCNT$(50),PSHMD$(50)
150 DIM MED$(50),MEDDATE$(50),MEDDOSE$(50),MEDMD$(50)
160 DIM ALLERGY$(50)
170 DIM IMMUNE$(50),IMMDATE$(50)
180 DIM SCRN$(50),SCRNDATE$(50),SCRNCNT$(50)
190 DIM COMMENT$(250),SENT$(50)
200 DIM DUMP1$(50),DUMP2$(50),DUMP3$(50),DUMP4$(50)
201 DIM CARRY$(250)
210 CNT=0:REM Counts the number of digits used
211 VC=1 :'Scroll control rate
220 OPEN "i",#1,"text.dat"
230 INPUT #1,VERSION:CNT=CNT+1
240 INPUT #1,GENDER$:CNT=CNT+1
250 INPUT #1,RACE$
260 INPUT #1,DOB$:CNT=CNT+3
270 INPUT #1,AREA:CNT=CNT+2
280 INPUT #1,PHONE:CNT=CNT+4
290 INPUT #1,PMH:CNT=CNT+1
300 FOR I=1 TO PMH
310     INPUT #1,PMH$(I):CNT=CNT+4
320     INPUT #1,PMHDATE$(I):CNT=CNT+3
330     INPUT #1,PMHCNT$(I):CNT=CNT+4
340     INPUT #1,PMHMD$(I):CNT=CNT+4
350 NEXT I
360 INPUT #1,PSH:CNT=CNT+1
370 FOR I=1 TO PSH
380     INPUT #1,PSH$(I):CNT=CNT+4
390     INPUT #1,PSHDATE$(I):CNT=CNT+3
400     INPUT #1,PSHCNT$(I):CNT=CNT+4
410     INPUT #1,PSHMD$(I):CNT=CNT+4
420 NEXT I
430 INPUT #1,MEDS:CNT=CNT+1
440 FOR I=1 TO MEDS
450     INPUT #1,MED$(I):CNT=CNT+4
460     INPUT #1,MEDDATE$(I):CNT=CNT+3
470     INPUT #1,MEDDOSE$(I):CNT=CNT+4
480     INPUT #1,MEDMD$(I):CNT=CNT+4
490 NEXT I
500 INPUT #1,ALLERGY:CNT=CNT+1
510 FOR I=1 TO ALLERGY
520     INPUT #1,ALLERGY$(I):CNT=CNT+4
530 NEXT I
540 INPUT #1,IMMUNE:CNT=CNT+1
550 FOR I=1 TO IMMUNE
560     INPUT #1,IMMUNE$(I):CNT=CNT+4
570     INPUT #1,IMMDATE$(I):CNT=CNT+3
580 NEXT I
590 INPUT #1,SCRN:CNT=CNT+1
600 FOR I=1 TO SCRN
610     INPUT #1,SCRN$(I):CNT=CNT+4
620     INPUT #1,SCRNDATE$(I):CNT=CNT+3
630     INPUT #1,SCRNCNT$(I):CNT=CNT+4
640 NEXT I
```

```
650 INPUT #1,LIVING$:CNT=CNT+1
660 INPUT #1,ORGAN$
670 INPUT #1,COMMENT:CNT=CNT+1
680 FOR I=1 TO COMMENT
690    INPUT #1,COMMENT$(I):CNT=CNT+4
700 NEXT I
810 INPUT #1,DOCTOR$:CNT=CNT+4
820 INPUT #1,ISSUE$:CNT=CNT+3
821 INPUT #1,MAHL$:CNT=CNT+4
825 CLOSE #1
826 OPEN "i",#1,"words.num"
827 INPUT #1,COUNT:CLOSE #1
828 OPEN "r",#1,"vll.imp",9:FIELD #1,3 AS SA$,3 AS L$,3 AS ID$
829 OPEN "r",#2,"vll.dat",1:FIELD #2,1 AS C$
830 CLS
840 GOSUB 10000
850 X=6:Y=11:K=11
860 GOSUB 14000:GOSUB 13250
870 USER$=HOLD$
880 X=6:Y=14:K=11
890 GOSUB 13000
900 PWORD$=HOLD$
910 IF USER$="" THEN run "menu"
1000 CLS
1010 GOSUB 10420
1020 CAP=100-INT(CNT/560*100+.5)
1030 COLOR 9:IF CAP<10 THEN COLOR 28
1040 LOCATE 5,36
1050 PRINT CAP;"% "
1060 COLOR 3
1070 X=68:Y=20:K=11
1080 GOSUB 14000
1090 GOSUB 13250
1100 IF HOLD$="q" THEN GOTO 20000
1110 IF HOLD$<"a" OR HOLD$>"j" THEN BEEP:GOTO 1070
1111 IF LEN(HOLD$)<>1 THEN BEEP:GOTO 1000
1120 IF HOLD$="a" THEN SECTION$="Demographic Information"
1130 IF HOLD$="b" THEN SECTION$="Past Medical History"
1140 IF HOLD$="c" THEN SECTION$="Past Surgical History"
1150 IF HOLD$="d" THEN SECTION$="Medications"
1160 IF HOLD$="e" THEN SECTION$="Allergies"
1170 IF HOLD$="f" THEN SECTION$="Immunizations"
1180 IF HOLD$="g" THEN SECTION$="Screening Procedures"
1190 IF HOLD$="h" THEN SECTION$="Living Will Status"
1200 IF HOLD$="i" THEN SECTION$="Organ Donor Status"
1210 IF HOLD$="j" THEN SECTION$="Comments"
1211 IF SECTION$="Living Will Status" OR SECTION$="Organ Donor Status" THEN 4000
1220 IF SECTION$="Comments" THEN CM=1
1221 CLS:GOSUB 11100
1230 COLOR 3
1240 LOCATE 3,8
1250 PRINT SECTION$
1260 CAP=100-INT(CNT/MAX*100+.5)
1270 COLOR 9:IF CAP<10 THEN COLOR 28
```

```
1280 LOCATE 3,62
1290 PRINT CAP;"%"
1300 REM Dump appropriate information to screen
1305 IF SECTION$="Demographic Information" THEN GOTO 7000
1306 IF SECTION$="Living Will Status" OR SECTION$="Organ Donor Status" THEN 4000
1310 IF SECTION$<>"Past Medical History" AND SECTION$<>"Past Surgical History" AND
SECTION$<>"Medications" AND SECTION$<>"Allergies" AND
SECTION$<>"Immunizations" AND SECTION$<>"Screening Procedures" AND
SECTION$<>"Comments" THEN PRINT "ERROR - ":STOP
1320 IF SECTION$="Comments" THEN 3000
1330 IF SECTION$="Past Medical History" THEN DUMP=PMH:FOR I=1 TO
PMH:DUMP1$(I)=PMH$(I):DUMP2$(I)=PMHDATE$(I):DUMP3$(I)=PMHCNT$(I):DUMP4$(I)=P
MHMD$(I):NEXT I:UNIT=4
1340 IF SECTION$="Past Surgical History" THEN DUMP=PSH:FOR I=1 TO
PSH:DUMP1$(I)=PSH$(I):DUMP2$(I)=PSHDATE$(I):DUMP3$(I)=PSHCNT$(I):DUMP4$(I)=PSH
MD$(I):NEXT I:UNIT=4
1350 IF SECTION$="Medications" THEN DUMP=MEDS:FOR I=1 TO
MEDS:DUMP1$(I)=MED$(I):DUMP2$(I)=MEDDATE$(I):DUMP3$(I)=MEDDOSE$(I):DUMP4$(I)
=MEDMD$(I):NEXT I:UNIT=4
1360 IF SECTION$="Allergies" THEN DUMP=ALLERGY:FOR I=1 TO
ALLERGY:DUMP1$(I)=ALLERGY$(I):NEXT I:UNIT=1
1370 IF SECTION$="Immunizations" THEN DUMP=IMMUNE:FOR I=1 TO
IMMUNE:DUMP1$(I)=IMMUNE$(I):DUMP2$(I)=IMMDATE$(I):NEXT I:UNIT=2
1380 IF SECTION$="Screening Procedures" THEN DUMP=SCRN:FOR I=1 TO
SCRN:DUMP1$(I)=SCRN$(I):DUMP2$(I)=SCRNDATE$(I):DUMP3$(I)=SCRNCNT$(I):NEXT
I:UNIT=3
1390 COLOR 11
1400 FOR II=1 TO DUMP
1410    LOCATE II+5,6
1420    COLOR 11:PRINT CHR$(64+II)+". ";
1430    COLOR 3:PRINT DUMP1$(II)
1440 NEXT II
1450 COLOR 11
1460 LOCATE I+5,6
1470 PRINT "Z. ---> ADD a new item here <---"
1480 X=70:Y=22
1490 K=11
1500 GOSUB 14000:GOSUB 13250
1510 IF HOLD$="z" THEN ADD=1:ITEM=DUMP+1:GOTO 1550
1520 IF HOLD$="q" THEN GOTO 1000
1530 IF HOLD$<"a" OR HOLD$>CHR$(95+II) THEN BEEP:GOTO 1220
1535 IF LEN(HOLD$)<>1 THEN BEEP:GOTO 1220
1540 ITEM=ASC(HOLD$)-96
1550 CLS
1560 GOSUB 11840
1570 CAP=100-INT(CNT/MAX*100+.5)
1575 COLOR 9:IF CAP<10 THEN COLOR 28
1580 LOCATE 3,44:PRINT CAP;"% "
1590 COLOR 3
1600 LOCATE 3,8:PRINT SECTION$
1610 IF SECTION$="Past Medical History" THEN
LABEL1$="Illness":LABEL2$="Date":LABEL3$="Center":LABEL4$="Physician"
1620 IF SECTION$="Past Surgical History" THEN
LABEL1$="Procedure":LABEL2$="Date":LABEL3$="Center":LABEL4$="Physician"
```

```
1630 IF SECTION$="Medications" THEN
LABEL1$="Medication":LABEL2$="Date":LABEL3$="Dose":LABEL4$="Physician"
1640 IF SECTION$="Allergies" THEN LABEL1$="Allergy"
1650 IF SECTION$="Immunizations" THEN LABEL1$="Immunization":LABEL2$="Date"
1660 IF SECTION$="Screening Procedures" THEN
LABEL1$="Procedure":LABEL2$="Date":LABEL3$="Center"
1670 COLOR 3
1680 LOCATE 7,7
1685 IF ADD=1 THEN PRINT "None.":GOTO 1790
1690 COLOR 11:PRINT LABEL1$+": ";:COLOR 3 :PRINT DUMP1$(ITEM)
1700 IF UNIT=1 THEN 1790
1710 LOCATE 8,7
1720 COLOR 11:PRINT LABEL2$+": ";:COLOR 3:PRINT DUMP2$(ITEM)
1730 IF UNIT=2 THEN 1790
1740 LOCATE 9,7
1750 COLOR 11:PRINT LABEL3$+": ";:COLOR 3:PRINT DUMP3$(ITEM)
1760 IF UNIT=3 THEN 1790
1770 LOCATE 10,7
1780 COLOR 11: PRINT LABEL4$+": ";:COLOR 3:PRINT DUMP4$(ITEM)
1790 REM
1800 LOCATE 17,7
1810 COLOR 11: PRINT LABEL1$+": "
1815 X=23:Y=17
1820 GOSUB 14000:GOSUB 13250
1821 IF HOLD$="" THEN GOSUB 6000:IF HOLD$="y" THEN 6500 ELSE 1815
1830 SEARCH$=HOLD$:FETCH$=HOLD$
1831 GOSUB 9000
1833 IF MATCH=1 THEN DUMP1$(ITEM)=FETCH$ ELSE GOSUB 8000:LOCATE 17,7:PRINT
SPACE$(60):GOTO 1800
1835 IF UNIT=1 THEN 2020
1850 LOCATE 18,7
1860 PRINT LABEL2$+": "
1870 X=23:Y=18
1880 GOSUB 14000:GOSUB 13250
1890 DTE$=HOLD$:REM GOSUB DATE VERIFY
1891 GOSUB 5000:IF MATCH=0 THEN LOCATE 18,7:PRINT SPACE$(60):GOTO 1850
1892 IF MATCH=1 THEN DUMP2$(ITEM)=DTE$
1900 IF UNIT=2 THEN 2020
1910 LOCATE 19,7
1920 PRINT LABEL3$+": "
1930 X=23:Y=19
1940 GOSUB 14000:GOSUB 13250
1950 FETCH$=HOLD$:SEARCH$=HOLD$:GOSUB 9000
1952 IF MATCH=1 THEN DUMP3$(ITEM)=FETCH$ ELSE GOSUB 8000:LOCATE 19,7:PRINT
SPACE$(60):GOTO 1910
1960 IF UNIT=3 THEN 2020
1970 LOCATE 20,7
1980 PRINT LABEL4$+": "
1990 X=23:Y=20
2000 GOSUB 14000:GOSUB 13250
2010 FETCH$=HOLD$:SEARCH$=HOLD$
2014 GOSUB 9000
2015 IF MATCH=1 THEN DUMP4$(ITEM)=FETCH$ ELSE GOSUB 8000:LOCATE 20,7:PRINT
SPACE$(60):GOTO 1910
```

```
2020 REM Information gathered in dump(nnn)$
2030 IF ADD=1 AND SECTION$="Past Medical History" THEN CNT=CNT+4+3+4+4
2040 IF ADD=1 AND SECTION$="Past Surgical History" THEN CNT=CNT+4+3+4+4
2050 IF ADD=1 AND SECTION$="Medications" THEN CNT=CNT+4+3+4+4
2060 IF ADD=1 AND SECTION$="Allergies" THEN CNT=CNT+4
2070 IF ADD=1 AND SECTION$="Immunizations" THEN CNT=CNT+4+3
2080 IF ADD=1 AND SECTION$="Screening Procedures" THEN CNT=CNT+4+3+4
2090 IF ADD=1 THEN DUMP=DUMP+1:ADD=0:ITEM=DUMP
2100 IF SECTION$="Past Medical History" THEN PMH=DUMP:FOR I=1 TO
PMH:PMH$(I)=DUMP1$(I):PMHDATE$(I)=DUMP2$(I):PMHCNT$(I)=DUMP3$(I):PMHMD$(I)=
DUMP4$(I):NEXT I
2110 IF SECTION$="Past Surgical History" THEN PSH=DUMP:FOR I=1 TO
PSH:PSH$(I)=DUMP1$(I):PSHDATE$(I)=DUMP2$(I):PSHCNT$(I)=DUMP3$(I):PSHMD$(I)=DU
MP4$(I):NEXT I
2120 IF SECTION$="Medications" THEN MEDS=DUMP:FOR I=1 TO
MEDS:MEDS$(I)=DUMP1$(I):MEDDATE$(I)=DUMP2$(I):MEDDOSES$(I)=DUMP3$(I):MEDMD$(I)
=DUMP4$(I):NEXT I
2130 IF SECTION$="Allergies" THEN ALLERGY=DUMP:FOR I=1 TO
ALLERGY:ALLERGY$(I)=DUMP1$(I):NEXT I
2140 IF SECTION$="Immunizations" THEN IMMUNE=DUMP:FOR I=1 TO
IMMUNE:IMMUNE$(I)=DUMP1$(I):IMMDATE$(I)=DUMP2$(I):NEXT I
2150 IF SECTION$="Screening Procedures" THEN SCRN=DUMP:FOR I=1 TO
SCRN:SCRN$(I)=DUMP1$(I):SCRNDATE$(I)=DUMP2$(I):SCRNCNT$(I)=DUMP3$(I):NEXT I
2160 GOTO 1220
3000 REM Comment Lines
3001 ITEM=0
3010 REM Begin Display
3015 MAGX=6:MAGY=6
3020 FOR II=1 TO COMMENT
3021 IF LAB=0 THEN LAB=1:COLOR 11:LOCATE MAGY,MAGX:PRINT CHR$(65+ITEM)+".
":MAGX=MAGX+4:ITEM=ITEM+1
3030    WORD$=COMMENT$(II)
3040    IF WORD$="." THEN LOCATE MAGY,MAGX+1:PRINT
".":MAGX=6:MAGY=MAGY+1:LAB=0:GOTO 3110
3050    GOSUB 15000
3060    IF MAGX+LEN(WORD$)>75 THEN MAGX=10:MAGY=MAGY+1
3070    LOCATE MAGY,MAGX
3080    COLOR 3
3090    PRINT WORD$
3095    SENT$(ITEM)=SENT$(ITEM)+" "+WORD$
3100    MAGX=MAGX+LEN(WORD$)+1
3110 NEXT II
3120 LOCATE MAGY,6:COLOR 11
3130 PRINT "Z. --->ADD Comments Here<---"
3140 K=11:X=70:Y=22
3150 GOSUB 14000:GOSUB 13250
3160 IF HOLD$="q" THEN 1000
3165 IF HOLD$="z" THEN ADD=1:GOTO 3400
3170 IF HOLD$<"a" OR HOLD$>CHR$(96+ITEM) OR LEN(HOLD$)<>1 THEN BEEP:GOTO
3140
3180 REM
3190 CHOICE=ASC(HOLD$)-96
3200 CPD=0:LAST=1
3210 FOR I=1 TO COMMENT
```

```
3220    IF COMMENT$(I)="." THEN CPD=CPD+1
3230    IF CPD=CHOICE AND NOVEL=0 THEN BEGIN=LAST:TERM=I:NOVEL=1
3231    IF COMMENT$(I)="." THEN LAST=I+1
3240 NEXT I
3250 REM Must delete comments from BEGIN to TERM
3251 TERM=TERM+1
3260 FOR I=BEGIN TO COMMENT-1
3270    COMMENT$(I)=COMMENT$(TERM+I-BEGIN+1)
3280 NEXT I
3290 COMMENT=COMMENT-(TERM-BEGIN)
3300 CNT=CNT-4*(TERM-BEGIN)
3310 GOTO 1220
3400 REM Add Comments
3401 GOSUB 11840
3402 CAP=100-INT(CNT/MAX*100+.5)
3403 COLOR 9:IF CAP<10 THEN COLOR 28
3404 LOCATE 3,44:PRINT CAP;"% "
3405 COLOR 3:LOCATE 3,8
3406 PRINT SECTION$
3410 LOCATE 13,8:COLOR 11:PRINT SPACE$(60)
3420 LOCATE 13,8:PRINT "Please enter comments, followed by a period."
3430 X=6:Y=17:K=11
3440 GOSUB 14000:GOSUB 13250
3450 IF HOLD$="" OR HOLD$="q" OR HOLD$="quit" THEN 1000
3451 IF RIGHT$(HOLD$,1) ="." THEN HOLD$=LEFT$(HOLD$,LEN(HOLD$)-1)
3460 HOLD$=HOLD$     +CHR$(199)
3461 FOR LOOP=1 TO 50:CARRY$(LOOP)="":NEXT LOOP
3470 I=1:T=1:' Counters for parser
3480 Z$=MID$(HOLD$,I,1)
3484 IF Z$=CHR$(199) THEN 3545
3485 IF Z$=" " THEN 3520
3490 CARRY$(T)=CARRY$(T)+Z$
3500 I=I+1
3510 GOTO 3480
3520 T=T+1
3530         I=I+1
3540 GOTO 3480
3545 T=T+1:CARRY$(T)="." :LN=T
3600 OK=0
3601 REM
3602 FOR II=1 TO LN
3603 SEARCH$=CARRY$(II)
3604 GOSUB 9000
3605 IF MATCH=0 THEN E$=CARRY$(II):OK=OK+1
3606 NEXT II
3607 IF OK=0 THEN 3619 ELSE GOSUB 8000
3608 LOCATE 13,7:PRINT SPACE$(60):COLOR 11
3609 LOCATE 13,7:PRINT "Cannot find: ";E$;:IF OK>1 THEN PRINT " and others." ELSE PRINT
" "
3610 ZZ=TIMER
3611 ZZZ=TIMER:IF ZZZ<ZZ+2 THEN 3611
3612 CLS:GOTO 1220
3619 FOR I=1 TO LN
3620 COMMENT=COMMENT+1
```

```
3630 CNT=CNT+4
3640 COMMENT$(COMMENT)=CARRY$(I)
3641 PRINT COMMENT$(COMMENT)
3650 NEXT I
3660 GOTO 1220
4000 REM Living Will Status and Organ Donor Status    SECTIONS
4010 IF LIVING$="" OR ORGAN$="" THEN ADD=1
4020 CLS:GOSUB 11840
4025 LOCATE 3,8:COLOR 3:PRINT SECTION$
4030 CAP=100-INT(CNT/MAX*100+.5)
4050 COLOR 9:IF CAP<10 THEN COLOR 28
4060 LOCATE 3,44:PRINT CAP;"% "
4061 COLOR 8:LOCATE 22,2 :PRINT "F1- Increase Scroll Rate"
4062     LOCATE 22,29:PRINT "F2- Decrease Scroll Rate"
4063 LOCATE 22,56:PRINT "PAUSE- Freeze Scroll"
4064 KEY(1) ON:KEY(2) ON
4065 COLOR 11:LOCATE 13,8:PRINT SPACE$(60):LOCATE 13,8:PRINT "Please select the
letter from the scroll display."
4070 IF SECTION$="Living Will Status" THEN ITEM=1 ELSE ITEM=2
4075 COLOR 11:LOCATE 6,7:IF ITEM=2 THEN PRINT "Organ Donor Status: ";ORGAN$ ELSE
PRINT "Living Will Status: ":LOCATE 7,7:IF LEN(LIVING$)<60 THEN PRINT LIVING$ ELSE PRINT
LEFT$(LIVING$,57)+"..."
4076 COLOR 11:LOCATE 16,7:IF ITEM=1 THEN PRINT "Living Will Status: " ELSE PRINT
"Organ Donor Status: "
4080 COLOR 19:LOCATE 8,7:PRINT "Choices":LOCATE 9,7:PRINT "-------":COLOR 3
4085 COLOR 3
4100 IF ITEM=1 THEN DISP$="(A) Patient has signed a Living Will in the past. (B) Patient
desires a Living Will but does not have one at this time. (C) Patient does not wish a Living Will.
(D) Living Will status unknown.":SPREAD=4
4110 IF ITEM=2 THEN DISP$="(A) Organ Donor Status unknown. (B) Patient desires donation
of organs. (C) Patient desires limited organ donation.":SPREAD=3
4111 GOTO 4300
4200 LOCATE 10,7:COLOR 3
4220 PRINT MID$(DISP$,1,60)
4222 IF CV>=1 THEN CV=0:DISP$=RIGHT$(DISP$,LEN(DISP$)-1)+LEFT$(DISP$,1)
4223 CV=CV+VC
4224 ON KEY(1) GOSUB 4240
4225 ON KEY(2) GOSUB 4270
4230 RETURN
4240 VC=VC+.5:IF VC>1 THEN VC=1
4250 RETURN
4270 VC=VC-.25:IF VC<.01 THEN VC=.01
4280 RETURN
4300 X=27:Y=16:K=11:COLOR 3
4310 DISP=1:GOSUB 14000:GOSUB 13250:DISP=0
4315 IF HOLD$="q" THEN 1000
4320 IF ITEM=1 AND (HOLD$<"a" OR HOLD$>"d" OR LEN(HOLD$)<>1) THEN BEEP:GOTO
4300
4330 IF ITEM=2 AND (HOLD$<"a" OR HOLD$>"c" OR LEN(HOLD$)<>1) THEN BEEP:GOTO
4300
4350 IF ITEM=1 AND HOLD$="a" THEN LIVING$="Patient has signed a Living Will in the
past."
4360 IF ITEM=1 AND HOLD$="b" THEN LIVING$="Patient desires a Living Will but does not
have one at this time."
```

```
4370 IF ITEM=1 AND HOLD$="c" THEN LIVING$="Patient does not wish a Living Will."
4380 IF ITEM=1 AND HOLD$="d" THEN LIVING$="Living Will status unknown."
4390 IF ITEM=2 AND HOLD$="a" THEN ORGAN$="Organ Donor Status unknown."
4400 IF ITEM=2 AND HOLD$="b" THEN ORGAN$="Patient desires donation of organs."
4410 IF ITEM=2 AND HOLD$="c" THEN ORGAN$="Patient desires limited organ donation."
4420 IF ADD=1 THEN CNT=CNT+1:ADD=0
4430 GOTO 1000
5000 REM check to insure date is correct format
5010 REM Requires date in DTE$
5020 REM Output:  MATCH =1 if okay, =0 if not okay
5025 MATCH=1
5030 RESULT$=DTE$
5040 GOSUB 5500
5050 IF MONTH<1 OR MONTH>12 OR MONTH<>INT(MONTH) THEN MATCH=0
5060 IF DAYS<1 OR DAYS>31 OR DAYS<>INT(DAYS) THEN MATCH=0
5070 IF YEAR<1889 OR YEAR>3000 OR YEAR<> INT(YEAR) THEN MATCH=0
5080 IF MATCH=1 THEN RETURN
5081 IF SVE=1 THEN RETURN :  REM program is in SAVE mode.
5090 LOCATE 13,8:PRINT SPACE$(60)
5100 COLOR 12:LOCATE 13,8
5110 PRINT "Error: ";
5120 COLOR 4
5130 PRINT "Date incorrect."
5140 ZZZ=TIMER
5150 ZZZZ=TIMER:IF ZZZZ<ZZZ+2 THEN 5150
5160 LOCATE 13,8:PRINT SPACE$(60)
5170 COLOR 3:LOCATE 13,8
5180 PRINT "Please enter date in (month/day/year) format. Ex: 11/2/1968"
5190 RETURN
5500 REM Date to decimal conversion utility
5510 REM Requires date  stored in RESULT$
5520 REM Format:   month/days/year       Ex:   11 / 2 / 1968
5530 REM Output will be in decimal, representing the number of days begining
5540 REM January 1, 1889
5550 REM
5560 REM Parse RESULT$ --> Month  /  Days   / Year
5570 RESULT$=RESULT$+"/"
5580 MONTH$="":DAYS$="":YEAR$=""
5590 GOSUB 5620:MONTH =VAL(WORD$)
5600 GOSUB 5620:DAYS =VAL(WORD$)
5610 GOSUB 5620:YEAR =VAL(WORD$)
5615 RETURN
5620 REM Parse based on "/" character
5630 WORD$=""
5640 FOR I=1 TO LEN(RESULT$)
5650   HOLD$=MID$(RESULT$,I,1)
5660   IF HOLD$<>"/" THEN WORD$=WORD$+HOLD$:NEXT I
5670 RESULT$=RIGHT$(RESULT$,LEN(RESULT$)-I)
5680 RETURN
6000 REM This routine checks to see if user wishes to delete current entry.
6010 LOCATE 13, 8:PRINT SPACE$(60)
6020 COLOR 22:LOCATE 13,8
6030 PRINT "Do you want to ";
6040 COLOR 28:PRINT"DELETE";
```

```
6050 COLOR 22
6060 PRINT " this entry (y/n)?"
6100 X=60:Y=13:K=12
6110 GOSUB 14000
6120 GOSUB 13250
6121 LOCATE 13,8:PRINT SPACE$(60)
6130 RETURN
6500 REM *********************************************Delete routine here
6510 FOR I=ITEM TO DUMP-1
6520    DUMP1$(I)=DUMP1$(I+1)
6530    DUMP2$(I)=DUMP2$(I+1)
6540    DUMP3$(I)=DUMP3$(I+1)
6550    DUMP4$(I)=DUMP4$(I+1)
6560 NEXT I
6570 DUMP=DUMP-1
6600 IF      SECTION$="Past Medical History" THEN CNT=CNT-4-3-4-4
6610 IF      SECTION$="Past Surgical History" THEN CNT=CNT-4-3-4-4
6620 IF      SECTION$="Medications" THEN CNT=CNT-4-3-4-4
6630 IF      SECTION$="Allergies" THEN CNT=CNT-4
6640 IF      SECTION$="Immunizations" THEN CNT=CNT-4-3
6650 IF      SECTION$="Screening Procedures" THEN CNT=CNT-4-3-4
6670 GOTO 2100
7000 REM Gender & Race Screen
7005 IF GENDER$="" OR RACE$="" THEN ADD=1
7010 LOCATE 6,6
7020 COLOR 11:PRINT "A. Gender: ";
7030 COLOR 3:PRINT GENDER$
7040 COLOR 11
7050 LOCATE 7,6
7080 PRINT "B. Race: ";
7090 COLOR 3: PRINT RACE$
7091 COLOR 11:LOCATE 8,6
7092 PRINT "C. Date of Birth: ";
7093 COLOR 3: PRINT DOB$
7094 COLOR 11:LOCATE 9,6
7095 PRINT "D. Emergency Telephone Number: ";
7096 COLOR 3:PRINT "("+MID$(STR$(AREA),2,LEN(STR$(AREA))-
1)+")"+MID$(STR$(PHONE),2,3)+"-"+RIGHT$(STR$(PHONE),4)
7100 K=11:X=70:Y=22
7110 GOSUB 14000:GOSUB 13250
7111 IF HOLD$="q" THEN 1000
7120 IF (HOLD$<>"a" AND HOLD$<>"b" AND HOLD$<>"c" AND HOLD$<>"d") OR
LEN(HOLD$)<>1 THEN BEEP:GOTO 7010
7130 IF HOLD$="a" THEN ITEM=1 ELSE ITEM=2
7140 CLS
7150 GOSUB 11840
7160 CAP=100-INT(CNT/MAX*100+.5)
7170 COLOR 9:IF CAP<10 THEN COLOR 28
7180 LOCATE 3,44:PRINT CAP;"% "
7190 COLOR 3
7200 LOCATE 3,8:PRINT SECTION$
7201 IF HOLD$="d" THEN 7500
7202 IF HOLD$="c" THEN 7750
7210 LOCATE 6,7:COLOR 11
```

```
7220 IF ITEM=1 THEN PRINT "Gender: ";GENDER$:LOCATE 16,7:PRINT "Gender: "
7230 IF ITEM=2 THEN PRINT "Race: ";RACE$:LOCATE 16,7:PRINT "Race: "
7240 COLOR 19:LOCATE 7,7:PRINT"Choices":LOCATE 8,7:PRINT"-------":COLOR 3
7250 IF ITEM=2 THEN 7310
7260 LOCATE 9,7:PRINT "Male"
7270 LOCATE 10,7 :PRINT "Female"
7280 LOCATE 9,25:PRINT "Not Specified"
7290 LOCATE 10,25:PRINT "Sex of Rearing Differs From Genotype"
7300 GOTO 7370
7310 COLOR 3 :LOCATE 9,7:PRINT "White"
7320 LOCATE 10,7 :PRINT "African American"
7330 LOCATE 9,25:PRINT "Hispanic"
7340 LOCATE 10,25:PRINT "American Indian"
7350 LOCATE 9 ,44:PRINT "Asian"
7360 LOCATE 10,44:PRINT "Not Specified"
7370 REM Choices printed
7371 COLOR 11:LOCATE 13,8:PRINT SPACE$(60):LOCATE 13,8:PRINT "Please select from choices shown above."
7380 X=15:Y=16:K=11:COLOR 3
7390 GOSUB 14000:GOSUB 13250
7400 IF ITEM=1 AND HOLD$<>"male" AND HOLD$<>"female" AND HOLD$<>"not specified" AND HOLD$="sex of rearing differs from genotype" THEN BEEP:LOCATE 16,15:PRINT SPACE$(20):GOTO 7380
7410 IF ITEM=2 AND HOLD$<>"white" AND HOLD$<>"african american" AND HOLD$<>"hispanic" AND HOLD$<>"american indian" AND HOLD$<>"asian" AND HOLD$<>"not specified" THEN BEEP:LOCATE 16,15:PRINT SPACE$(20):GOTO 7380
7420 IF ITEM=1 THEN GENDER$=HOLD$
7430 IF ITEM=2 THEN RACE$=HOLD$
7435 IF ADD=1 THEN ADD=0:CNT=CNT+1:' This software will ADD race & gender to a blank card, but will never DELETE such information. Information can only be modified.
7440 GOTO 1220
7500 REM Telephone number input routine
7505 IF AREA=0 OR PHONE=0 THEN ADD=1
7510 COLOR 11:LOCATE 6,7
7520 PRINT "Emergency Telephone Number: ";:COLOR 3
7530 PRINT "("+MID$(STR$(AREA),2,LEN(STR$(AREA))-1)+")"+MID$(STR$(PHONE),2,3)+"-"+RIGHT$(STR$(PHONE),4)
7540 LOCATE 16,7:PRINT"Area Code: "
7550 X=23:Y=16:K=11:COLOR 3:GOSUB 14000:GOSUB 13250
7551 IF HOLD$="q" THEN 1000
7560 IF VAL(HOLD$)<1 OR VAL(HOLD$)>999 THEN BEEP:LOCATE 16,7:PRINT SPACE$(60):GOTO 7540
7565 AREA=VAL(HOLD$)
7570 LOCATE 17,7:PRINT"Phone Number: "
7580 X=23:Y=17:K=11:COLOR 3:GOSUB 14000:GOSUB 13250
7590 FOR I=1 TO LEN(HOLD$)
7600    IF MID$(HOLD$,I,1)="-" THEN HOLD$=LEFT$(HOLD$,I-1)+RIGHT$(HOLD$,LEN(HOLD$)-I)
7610 NEXT I
7620 PHONE=VAL(HOLD$)
7621 IF PHONE<1 OR PHONE>9999999! THEN BEEP:LOCATE 17,7:PRINT SPACE$(60):GOTO 7570
7640 IF ADD=1 THEN ADD=0:CNT=CNT+2+4
7650 GOTO 1220
```

```
7700 REM DOB$
7750 REM Date of Birth entry module
7760 IF DOB$="" THEN ADD=1
7770 COLOR 11:LOCATE 6,7
7780 PRINT "Date of Birth: ";:COLOR 3
7790 PRINT DOB$
7800 LOCATE 16,7
7810 PRINT "Date of Birth: "
7820 X=23:Y=16:K=11:GOSUB 14000
7830 DTE$=HOLD$
7840 GOSUB 5000
7850 IF MATCH=0 THEN LOCATE 16,23:PRINT SPACE$(30):GOTO 7820
7860 DOB$=DTE$
7870 IF ADD=1 THEN ADD=0:CNT=CNT+3
7880 GOTO 1220
8000 REM Error - Word not in VLL
8010 LOCATE 13,7:PRINT SPACE$(60)
8020 COLOR 12:LOCATE 13,7
8030 PRINT "Error: ";
8040        COLOR 4
8050 PRINT "Word not in database."
8060 BEEP
8061 ZZZ=TIMER
8062 ZZZZ=TIMER:IF ZZZZ<ZZZ+2 THEN 8062
8063 LOCATE 13,7:PRINT SPACE$(60)
8064 LOCATE 13,7
8065 COLOR 3
8066 PRINT "Please try again, or run INFORM after exit."
8070 SHELL "echo "+FETCH$+">>inform.dat"
8080 RETURN
9000 REM Scan subroutine V.1.0
9010 REM Created by S. Behram on 10/16/1993
9020 REM
9030 REM Requires incoming search string in SEARCH$
9040 REM Requires the total number of words in entire dbase in COUNT
9050 REM Also needs VLL files to have already been opened and field
9060 REM statements declared:
9070 REM OPEN "R",#1,"vll.jmp",9    FIELD #1,3 as sa$,3 as I$,3 as id$
9080 REM OPEN "R",#2,"vll.dat",1    FIELD #2,1 as c$
9090 REM
9100 REM The STR2DEC subroutine must be install at line 7000
9110 REM Program returns MATCH=1 for positive match
9120 REM Program returns strings FIND(1-6)$ as closest matches
9130 REM Begin dbase search
9135 IF SVE<>1 THEN COLOR 28:LOCATE 3,56:PRINT CHR$(219)
9140 JMP=INT(COUNT/2+.5):CURR=JMP
9150 REM Retrieve item and current JMP location
9160 GOSUB 9470:'routine to retrieve string at CURR
9170 IF ITEM$=SEARCH$ THEN MATCH=1:GOTO 9250
9180 JMP=INT(JMP/2+.5)
9190 IF JMP<1 THEN JMP=1
9200 IF ITEM$>SEARCH$ THEN CURR=CURR-JMP:IF CURR<1 THEN CURR=1
9210 IF ITEM$<SEARCH$ THEN CURR=CURR+JMP:IF CURR>COUNT+WORDCNT THEN CURR=COUNT+WORDCNT
```

```
9220 IF ITEM$=LAST$ THEN MATCH=0:GOTO 9250
9230 LAST$=HOLD$:HOLD$=ITEM$
9240 GOTO 9160
9250 REM Search complete
9260 REM Will store the results of search in find$(1-6)
9270 REM Closest answer is in curr
9280 IF CURR<3 THEN CURR=CURR+1:GOTO 9280
9290 IF CURR>COUNT-3 THEN CURR=CURR-1:GOTO 9290
9300 CR=0:CRR=CURR
9310 FOR CURR=CURR-2 TO CURR+3
9320   CR=CR+1
9330   GOSUB 9470
9340   FIND$(CR)=ITEM$
9350 NEXT CURR:CURR=CRR
9360 HOLD$=FIND$(1)
9370 FIND$(1)=FIND$(3)
9380 FIND$(3)=HOLD$
9385 LOCATE 3,56:PRINT " ":COLOR 11
9390 RETURN
9400 REM This routine converts a string base 256 integer into decimal
9410 REM Requires 256 base integer in RESULT$, returns answer in DECIMAL.
9420 DIG3=ASC(LEFT$(RESULT$,1))
9430 DIG2=ASC(MID$(RESULT$,2,1))
9440 DIG1=ASC(RIGHT$(RESULT$,1))
9450 DECIMAL=DIG3*256^2+DIG2*256^1+DIG1*256^0
9460 RETURN
9470 REM Retrieves string located at CURR.  Returns it in Item$
9480 REM Retrieve item and current JMP location
9490 GET #1,CURR
9500 RESULT$=SA$:GOSUB 9400:SA=DECIMAL
9510 RESULT$=L$:GOSUB 9400:L=DECIMAL
9520 RESULT$=ID$:GOSUB 9400:ID=DECIMAL
9530 ITEM$=""
9540 FOR I=1 TO L
9550   GET #2,I+SA-1
9560   ITEM$=ITEM$+C$
9570 NEXT I
9580 IF BUG=0 THEN 9730
9590 IF SA<10 THEN GOTO 9730:'Rem to close to the end
9600 REM This is to fix DOS bug
9610 IF (SA-1)/256<>INT((SA-1)/256) THEN 9730
9620 HOLD=CURR:H$=ITEM$
9630 BUG=0
9640 CURR=CURR-1:GOSUB 9470:LOW$=ITEM$
9650 CURR=CURR+2:GOSUB 9470:HIGH$=ITEM$
9660 CURR=HOLD:GOSUB 9470
9670 BUG=1
9680 REM ITEM$=H$:CURR=HOLD
9690 IF ITEM$>LOW$ AND ITEM$<HIGH$ THEN 9730
9700 REM Bug detected.
9710 BEEP
9720 P$=RIGHT$(ITEM$,1):ITEM$=P$+LEFT$(ITEM$,LEN(ITEM$)-1)
9730 RETURN
9999 STOP
```

```
10000 REM Password Screen
10010 CLS: COLOR 7, 0: PRINT "              ";
10020 COLOR 14, 0: PRINT " ";: COLOR 7, 0: PRINT "         ";
10030 COLOR 14, 0: PRINT "Patient Data Inventory ";
10040 COLOR 7, 0: PRINT "    ";: COLOR 14, 0: PRINT "           ";
10050 COLOR 8, 0: PRINT "                    ";
10060 COLOR 7, 0: PRINT "                       ";
10070 COLOR 8, 0: PRINT "          ";
10080 COLOR 7, 0: PRINT "                       ";
10090 COLOR 8, 0: PRINT "              ";
10100 COLOR 11, 0: PRINT "     ";: COLOR 7, 0: PRINT "                        ";
10110 COLOR 8, 0: PRINT "               ";
10120 COLOR 11, 0: PRINT "     ";: COLOR 8, 0: PRINT " ";
10130 COLOR 7, 0: PRINT "                ";
10140 COLOR 8, 0: PRINT "              ";
10150 COLOR 11, 0: PRINT "     ";: COLOR 8, 0: PRINT " ";
10160 COLOR 7, 0: PRINT "                ";
10170 COLOR 8, 0: PRINT "    ";: COLOR 7, 0: PRINT "+";
10180 COLOR 3, 0: PRINT "Instructions";: COLOR 7, 0: PRINT "----------------------------------+    ";
10190 COLOR 8, 0: PRINT "    ";: COLOR 7, 0: PRINT "¦";
10200 COLOR 11, 0: PRINT "     Please enter user identification and password.     ";
10210 COLOR 8, 0: PRINT "¦";: COLOR 7, 0: PRINT "   ";
10220 COLOR 8, 0: PRINT "    +----------------------------------------------------+";
10230 COLOR 7, 0: PRINT "   ";: COLOR 8, 0: PRINT "   ";
10240 COLOR 7, 0: PRINT "+";: COLOR 3, 0: PRINT "User Identification";
10250 COLOR 7, 0: PRINT "------------------------------------------+   ";
10260 COLOR 8, 0: PRINT "    ";: COLOR 7, 0: PRINT "¦";
10270 COLOR 11, 0: PRINT "                                        ";
10280 COLOR 8, 0: PRINT "¦";: COLOR 7, 0: PRINT "   ";
10290 COLOR 8, 0: PRINT "    +----------------------------------------------------+";
10300 COLOR 7, 0: PRINT "   ";: COLOR 8, 0: PRINT "   ";
10310 COLOR 7, 0: PRINT "+";: COLOR 3, 0: PRINT "User Password";
10320 COLOR 7, 0: PRINT "------------------------------------------------+   ";
10330 PRINT " ";: COLOR 8, 0: PRINT "   ";: COLOR 7, 0: PRINT "¦";
10340 COLOR 11, 0: PRINT "                                        ";
10350 COLOR 8, 0: PRINT "¦";: COLOR 7, 0: PRINT "   ";
10360 PRINT " ";: COLOR 8, 0: PRINT "   +----------------------------------------------+";
10370 COLOR 7, 0: PRINT "   ";: PRINT " ";: COLOR 8, 0: PRINT "            ";
10380 COLOR 3, 0: PRINT "           ";
10390 COLOR 7, 0: PRINT "              ";
10400 COLOR 7, 0
10410 RETURN
10420 REM Sections Screen
10430 CLS: COLOR 7, 0: PRINT "              ";
10440 COLOR 14, 0: PRINT " ";: COLOR 7, 0: PRINT "         ";
10450 COLOR 14, 0: PRINT "Patient Data Inventory ";
10460 COLOR 7, 0: PRINT "    ";: COLOR 14, 0: PRINT "           ";
10470 COLOR 8, 0: PRINT "                    ";
10480 COLOR 7, 0: PRINT "                       ";
10490 COLOR 8, 0: PRINT "              ";
```

```
10500 COLOR 7, 0: PRINT "                               ";
10510 COLOR 8, 0: PRINT "              ";
10520 COLOR 7, 0: PRINT "+";: COLOR 3, 0: PRINT "Capacity";
10530 COLOR 7, 0: PRINT "+              ";
10540 COLOR 8, 0: PRINT "              ";
10550 COLOR 7, 0: PRINT "¤     ";: COLOR 8, 0: PRINT "¤";
10560 COLOR 7, 0: PRINT "              ";
10570 COLOR 8, 0: PRINT "              +--------+";
10580 COLOR 7, 0: PRINT "              ";
10590 COLOR 8, 0: PRINT "              ";
10600 COLOR 15, 0: PRINT "+";: COLOR 3, 0: PRINT "Sections";
10610 COLOR 7, 0: PRINT "----------------------+              ";
10620 COLOR 8, 0: PRINT "              ";
10630 COLOR 7, 0: PRINT "¤ ";: COLOR 11, 0: PRINT "A.";
10640 COLOR 7, 0: PRINT " Demographic Information   ";
10650 COLOR 8, 0: PRINT "¤";: COLOR 7, 0: PRINT "              ";
10660 COLOR 8, 0: PRINT "              ";
10670 COLOR 7, 0: PRINT "¤ ";: COLOR 11, 0: PRINT "B.";
10680 COLOR 7, 0: PRINT " Past Medical History     ";
10690 COLOR 8, 0: PRINT "¤";: COLOR 7, 0: PRINT "              ";
10700 COLOR 8, 0: PRINT "              ";
10710 COLOR 7, 0: PRINT "¤ ";: COLOR 11, 0: PRINT "C.";
10720 COLOR 7, 0: PRINT " Past Surgical History    ";
10730 COLOR 8, 0: PRINT "¤";: COLOR 7, 0: PRINT "              ";
10740 COLOR 8, 0: PRINT "              ";
10750 COLOR 7, 0: PRINT "¤ ";: COLOR 11, 0: PRINT "D.";
10760 COLOR 7, 0: PRINT " Medications              ";
10770 COLOR 8, 0: PRINT "¤";: COLOR 7, 0: PRINT "              ";
10780 COLOR 8, 0: PRINT "              ";
10790 COLOR 7, 0: PRINT "¤ ";: COLOR 11, 0: PRINT "E.";
10800 COLOR 7, 0: PRINT " Allergies                ";
10810 COLOR 8, 0: PRINT "¤";: COLOR 7, 0: PRINT "              ";
10820 COLOR 8, 0: PRINT "              ";
10830 COLOR 7, 0: PRINT "¤ ";: COLOR 11, 0: PRINT "F.";
10840 COLOR 7, 0: PRINT " Immunizations            ";
10850 COLOR 8, 0: PRINT "¤";: COLOR 7, 0: PRINT "              ";
10860 PRINT " ";: COLOR 8, 0: PRINT "              ";
10870 COLOR 7, 0: PRINT "¤ ";: COLOR 11, 0: PRINT "G.";
10880 COLOR 7, 0: PRINT " Screening Procedures     ";
10890 COLOR 8, 0: PRINT "¤";: COLOR 7, 0: PRINT "              ";
10900 PRINT " ";: COLOR 8, 0: PRINT "              ";
10910 COLOR 7, 0: PRINT "¤ ";: COLOR 11, 0: PRINT "H.";
10920 COLOR 7, 0: PRINT " Living Will Status       ";
10930 COLOR 8, 0: PRINT "¤";: COLOR 7, 0: PRINT "              ";
10940 PRINT " ";: COLOR 8, 0: PRINT "              ";
10950 COLOR 7, 0: PRINT "¤ ";: COLOR 11, 0: PRINT "I.";
10960 COLOR 7, 0: PRINT " Organ Donor Status       ";
10970 COLOR 8, 0: PRINT "¤";: COLOR 7, 0: PRINT "              ";
10980 PRINT "          ¤ ";: COLOR 11, 0: PRINT "J.";
10990 COLOR 7, 0: PRINT " Special Comments         ";
11000 COLOR 8, 0: PRINT "¤";: COLOR 7, 0: PRINT "              ";
11010 PRINT "              ";: COLOR 8, 0: PRINT "+------------------------------+";
11020 COLOR 7, 0: PRINT "                  ";
11030 PRINT "   +";: COLOR 3, 0: PRINT "Instructions";
```

```
11040 COLOR 7, 0: PRINT "---------------------------------------------------------------+    ";
11050 PRINT "    ";: COLOR 11, 0: PRINT " Please enter the Section letter to be modified (Q to quit):     ";
11060 COLOR 8, 0: PRINT "";: COLOR 7, 0: PRINT "   ";
11070 PRINT "   ";: COLOR 8, 0: PRINT "+-------------------------------------------------------------------+";
11080 COLOR 7, 0
11090 RETURN
11100 REM Items screen
11110 CLS: COLOR 7, 0: PRINT "        ";
11120 COLOR 14, 0: PRINT "   ";: COLOR 7, 0: PRINT "    ";
11130 COLOR 14, 0: PRINT "Patient Data Inventory ";
11140 COLOR 7, 0: PRINT "    ";: COLOR 14, 0: PRINT "               ";
11150 COLOR 8, 0: PRINT "    ";: COLOR 15, 0: PRINT "+";
11160 COLOR 3, 0: PRINT "Section";: COLOR 7, 0: PRINT "-------------------------+ +";
11170 COLOR 3, 0: PRINT "Capacity";: COLOR 7, 0: PRINT "+     ";
11180 COLOR 8, 0: PRINT "    ";: COLOR 7, 0: PRINT "  ";
11190 COLOR 8, 0: PRINT " ";: COLOR 11, 0: PRINT "  ";
11200 COLOR 7, 0: PRINT " ";: COLOR 12, 0: PRINT " ";
11210 COLOR 7, 0: PRINT "              ";
11220 COLOR 8, 0: PRINT "   ";: COLOR 7, 0: PRINT "         ";
11230 COLOR 8, 0: PRINT "";: COLOR 7, 0: PRINT "      ";
11240 COLOR 8, 0: PRINT "   +-----------------------+    ";
11250 COLOR 7, 0: PRINT "           ";: COLOR 8, 0: PRINT "+--------+";
11260 COLOR 7, 0: PRINT "         ";: COLOR 8, 0: PRINT "  ";
11270 COLOR 7, 0: PRINT "+";: COLOR 3, 0: PRINT "Items";
11280 COLOR 7, 0: PRINT "---------------------------------------------------------+    ";
11290 COLOR 8, 0: PRINT "  ";: COLOR 7, 0: PRINT "";
11300 COLOR 8, 0: PRINT "  ";: COLOR 11, 0: PRINT "  ";
11310 COLOR 8, 0: PRINT "                                 ";
11320 COLOR 7, 0: PRINT "      ";: COLOR 8, 0: PRINT "  ";
11330 COLOR 7, 0: PRINT "";: COLOR 8, 0: PRINT "                        ";
11340 COLOR 7, 0: PRINT "          ";: COLOR 8, 0: PRINT "";
11350 COLOR 7, 0: PRINT "       ";: COLOR 8, 0: PRINT "  ";
11360 COLOR 7, 0: PRINT "";: COLOR 8, 0: PRINT "                       ";
11370 COLOR 7, 0: PRINT "";: COLOR 8, 0: PRINT " ";
11380 COLOR 7, 0: PRINT "       ";: COLOR 8, 0: PRINT "";
11390 COLOR 7, 0: PRINT "       ";: COLOR 8, 0: PRINT " ";
11400 COLOR 7, 0: PRINT "";: COLOR 8, 0: PRINT "                     ";
11410 COLOR 7, 0: PRINT "          ";: COLOR 8, 0: PRINT "";
11420 COLOR 7, 0: PRINT "       ";: COLOR 8, 0: PRINT " ";
11430 COLOR 7, 0: PRINT "";: COLOR 8, 0: PRINT "                      ";
11440 COLOR 7, 0: PRINT "         ";: COLOR 8, 0: PRINT "";
11450 COLOR 7, 0: PRINT "       ";: COLOR 8, 0: PRINT " ";
11460 COLOR 7, 0: PRINT "";: COLOR 8, 0: PRINT "                     ";
11470 COLOR 7, 0: PRINT "          ";: COLOR 8, 0: PRINT "";
11480 COLOR 7, 0: PRINT "       ";: COLOR 8, 0: PRINT " ";
11490 COLOR 7, 0: PRINT "";: COLOR 8, 0: PRINT "                    ";
11500 COLOR 7, 0: PRINT "         ";: COLOR 8, 0: PRINT "";
11510 COLOR 7, 0: PRINT "       ";: COLOR 8, 0: PRINT " ";
11520 COLOR 7, 0: PRINT "";: COLOR 8, 0: PRINT "                     ";
11530 COLOR 7, 0: PRINT "          ";: COLOR 8, 0: PRINT "";
11540 COLOR 7, 0: PRINT "       ";: PRINT " ";
```

```
11550 COLOR 8, 0: PRINT "    ";: COLOR 7, 0: PRINT "▫";
11560 COLOR 8, 0: PRINT "                              ";
11570 COLOR 7, 0: PRINT "            ";: COLOR 8, 0: PRINT "▫";
11580 COLOR 7, 0: PRINT "      ";: PRINT " ";
11590 COLOR 8, 0: PRINT "    ";: COLOR 7, 0: PRINT "▫";
11600 COLOR 8, 0: PRINT "                              ";
11610 COLOR 7, 0: PRINT "            ";: COLOR 8, 0: PRINT "▫";
11620 COLOR 7, 0: PRINT "      ";: PRINT " ";
11630 COLOR 8, 0: PRINT "    ";: COLOR 7, 0: PRINT "▫";
11640 COLOR 8, 0: PRINT "                              ";
11650 COLOR 7, 0: PRINT "            ";: COLOR 8, 0: PRINT "▫";
11660 COLOR 7, 0: PRINT "      ";: PRINT "  ▫           ";
11670 COLOR 8, 0: PRINT "                      ";
11680 COLOR 7, 0: PRINT "            ";: COLOR 8, 0: PRINT "▫";
11690 COLOR 7, 0: PRINT "      ";: PRINT "    ▫";
11700 COLOR 8, 0: PRINT "                                  ▫";
11710 COLOR 7, 0: PRINT "      ";: PRINT "    ▫";
11720 COLOR 8, 0: PRINT "                               ▫    ";
11730 COLOR 7, 0: PRINT "    ";: PRINT "    ";: COLOR 8, 0: PRINT "+--------------------------------------------------------+    ";
11740 COLOR 7, 0: PRINT "    ";: PRINT "   +";: COLOR 3, 0: PRINT "Instructions";
11750 COLOR 7, 0: PRINT "-----------------------------------------------------------+";
11760 COLOR 8, 0: PRINT " ";: COLOR 7, 0: PRINT "   ";
11770 COLOR 3, 0: PRINT " ";: COLOR 7, 0: PRINT "▫";
11780 IF CM=0 THEN COLOR 11, 0: PRINT "Please enter the Item letter to be modified (Q to quit this menu):   ";
11781 IF CM=1 THEN CM=0:COLOR 11, 0: PRINT "Please enter the Item letter to be";:COLOR 27:PRINT " DELETED";:COLOR 11:PRINT" (Q to quit this menu):    ";
11790 COLOR 8, 0: PRINT "▫";: COLOR 3, 0: PRINT " ";
11800 COLOR 7, 0: PRINT "   ";: COLOR 3, 0: PRINT " ";
11810 COLOR 8, 0: PRINT "+-----------------------------------------------------------------+";
11820 COLOR 7, 0
11830 RETURN
11840 REM Update screen
11850 CLS: COLOR 7, 0: PRINT "         ";
11860 COLOR 14, 0: PRINT " ";: COLOR 7, 0: PRINT "     ";
11870 COLOR 14, 0: PRINT "Patient Data Inventory ";
11880 COLOR 7, 0: PRINT "   ";: COLOR 14, 0: PRINT "             ";
11890 COLOR 8, 0: PRINT "   ";: COLOR 15, 0: PRINT "+";
11900 COLOR 3, 0: PRINT "Section";: COLOR 7, 0: PRINT "-----------------------+ +";
11910 COLOR 3, 0: PRINT "Capacity";: COLOR 7, 0: PRINT "+  ";
11920 COLOR 8, 0: PRINT "+-+";: COLOR 7, 0: PRINT "   ";
11930 COLOR 3, 0: PRINT "      ";: COLOR 7, 0: PRINT "       ";
11940 COLOR 8, 0: PRINT "    ";: COLOR 7, 0: PRINT "▫ ";
11950 COLOR 8, 0: PRINT " ";: COLOR 11, 0: PRINT " ";
11960 COLOR 7, 0: PRINT " ";: COLOR 12, 0: PRINT " ";
11970 COLOR 7, 0: PRINT "                  ";
11980 COLOR 8, 0: PRINT "▫ ";: COLOR 7, 0: PRINT "▫      ";
11990 COLOR 8, 0: PRINT "▫";: COLOR 7, 0: PRINT " ";
12000 COLOR 8, 0: PRINT " ▫▫ Searching...";: COLOR 7, 0: PRINT "     ";
12010 COLOR 8, 0: PRINT "    +-----------------------+ +--------+";
12020 COLOR 7, 0: PRINT " ";: COLOR 8, 0: PRINT "+-+";
12030 COLOR 7, 0: PRINT " ";: COLOR 3, 0: PRINT "       ";
```

```
12040 COLOR 7, 0: PRINT "        ";: COLOR 8, 0: PRINT "    ";
12050 COLOR 7, 0: PRINT "+";: COLOR 3, 0: PRINT "Current Information ";
12060 COLOR 7, 0: PRINT "---------------------------------------+     ";
12070 COLOR 8, 0: PRINT "   ";: COLOR 7, 0: PRINT "¤";
12080 COLOR 8, 0: PRINT " ";: COLOR 11, 0: PRINT "   ";
12090 COLOR 8, 0: PRINT "                                          ¤";
12100 COLOR 7, 0: PRINT "     ";: COLOR 8, 0: PRINT "    ";
12110 COLOR 7, 0: PRINT "¤";: COLOR 8, 0: PRINT "                                       ";
12120 COLOR 7, 0: PRINT "           ";: COLOR 8, 0: PRINT "¤";
12130 COLOR 7, 0: PRINT "      ";: COLOR 8, 0: PRINT "   ";
12140 COLOR 7, 0: PRINT "¤";: COLOR 8, 0: PRINT "                                       ";
12150 COLOR 7, 0: PRINT " ";: COLOR 8, 0: PRINT " ";
12160 COLOR 7, 0: PRINT "       ";: COLOR 8, 0: PRINT "¤";
12170 COLOR 7, 0: PRINT "     ";: COLOR 8, 0: PRINT "    ";
12180 COLOR 7, 0: PRINT "¤";: COLOR 8, 0: PRINT "                                       ";
12190 COLOR 7, 0: PRINT "         ";: COLOR 8, 0: PRINT "¤";
12200 COLOR 7, 0: PRINT "     ";: COLOR 8, 0: PRINT "   ";
12210 COLOR 7, 0: PRINT "¤";: COLOR 8, 0: PRINT "                                       ";
12220 COLOR 7, 0: PRINT "         ";: COLOR 8, 0: PRINT "¤";
12230 COLOR 7, 0: PRINT "     ";: COLOR 8, 0: PRINT "   +-----------------------------------------+";
12240 COLOR 7, 0: PRINT "       ";: COLOR 8, 0: PRINT "   ";
12250 COLOR 7, 0: PRINT "+";: COLOR 3, 0: PRINT "Instructions";
12260 COLOR 7, 0: PRINT "-----------------------------------------+    ";
12270 COLOR 8, 0: PRINT "   ";: COLOR 7, 0: PRINT "¤";
12280 COLOR 11, 0: PRINT "     Please enter the specific  information requested.     ";
12290 COLOR 8, 0: PRINT "¤";: COLOR 11, 0: PRINT "   ";
12300 COLOR 8, 0: PRINT " ";: COLOR 7, 0: PRINT "   ";
12310 PRINT " ";: COLOR 8, 0: PRINT "  +-------------------------------------------------+    ";
12320 COLOR 7, 0: PRINT "    ";: PRINT " ";: COLOR 8, 0: PRINT "   ";
12330 COLOR 7, 0: PRINT "+";: COLOR 3, 0: PRINT "Modified Information";
12340 COLOR 7, 0: PRINT "-------------------------------------+    ";
12350 PRINT " ";: COLOR 8, 0: PRINT "   ";: COLOR 7, 0: PRINT "¤";
12360 COLOR 8, 0: PRINT " ";: COLOR 11, 0: PRINT "   ";
12370 COLOR 8, 0: PRINT "                                          ¤";
12380 COLOR 7, 0: PRINT "      ";: PRINT "   ¤";
12390 COLOR 8, 0: PRINT "                                       ";
12400 COLOR 7, 0: PRINT "            ";: COLOR 8, 0: PRINT "¤";
12410 COLOR 7, 0: PRINT "      ";: PRINT "   ¤";
12420 COLOR 8, 0: PRINT "                                       ";
12430 COLOR 7, 0: PRINT " ";: COLOR 8, 0: PRINT "   ";
12440 COLOR 7, 0: PRINT "         ";: COLOR 8, 0: PRINT "¤";
12450 COLOR 7, 0: PRINT "     ";: PRINT "   ¤";
12460 COLOR 8, 0: PRINT "                                       ";
12470 COLOR 7, 0: PRINT "          ";: COLOR 8, 0: PRINT "¤   ";
12480 COLOR 7, 0: PRINT "  ";: PRINT "   ¤";
12490 COLOR 8, 0: PRINT "                                       ";
12500 COLOR 7, 0: PRINT "           ";: COLOR 8, 0: PRINT "¤    ";
12510 COLOR 7, 0: PRINT "   ";: PRINT "   ";: COLOR 8, 0: PRINT "+-------------------------------------------+";
12520 COLOR 7, 0
12530 RETURN
13000 REM Advanced data entry read/write module
```

```
13010 REM Requires x,y and k for color
13020 REM Stores string in HOLD$
13030 XO=0:YO=0:HOLD$=""
13040 CURSOR$(1)=CHR$(221)
13050 CURSOR$(2)=CHR$(223)
13060 CURSOR$(3)=CHR$(222)
13070 CURSOR$(4)=CHR$(220)
13080 I$=INKEY$
13090 CUR=CUR+.1 :IF CUR>4 THEN CUR=1
13100 LOCATE Y+YO,X+XO
13110 PRINT CURSOR$(INT(CUR+.5))
13120 IF I$="" THEN 13080
13130 LOCATE Y+YO,X+XO
13140 PRINT " "
13150 IF ASC(I$)=8 AND XO>0 THEN XO=XO-1:HOLD$=LEFT$(HOLD$,LEN(HOLD$)-1):GOTO 13080
13160 IF ASC(I$)=13 THEN 13230
13170 XO=XO+1
13180 HOLD$=HOLD$+I$
13190 COLOR K
13200 LOCATE Y+YO,X+XO-1
13210 PRINT CHR$(2)
13220 GOTO 13080
13230 HOLD$=RIGHT$(HOLD$,XO)
13240 RETURN
13250 REM Convert to lower case
13260 REM Requires HOLD$, returns HOLD$
13270 FOR I=1 TO LEN(HOLD$)
13280 IF MID$(HOLD$,I,1)>="A" AND MID$(HOLD$,I,1)<="Z" THEN MID$(HOLD$,I,1)=CHR$(ASC(MID$(HOLD$,I,1))+32)
13290 NEXT I
13300 RETURN
14000 REM Advanced data entry read/write module
14010 REM Requires x,y and k for color
14020 REM Stores string in HOLD$
14030 XO=0:YO=0:HOLD$=""
14040 CURSOR$(1)=CHR$(221)
14050 CURSOR$(2)=CHR$(223)
14060 CURSOR$(3)=CHR$(222)
14070 CURSOR$(4)=CHR$(220)
14080 I$=INKEY$
14090 CUR=CUR+.1 :IF CUR>4 THEN CUR=1
14091 IF DISP=1 THEN CUR=CUR+.9:IF CUR>4 THEN CUR=1
14100 LOCATE Y+YO,X+XO
14110 PRINT CURSOR$(INT(CUR+.5))
14111 IF DISP=1 THEN GOSUB 4200
14120 IF I$="" THEN 14080
14130 LOCATE Y+YO,X+XO
14140 PRINT " "
14150 IF ASC(I$)=8 AND XO>0 THEN XO=XO-1:HOLD$=LEFT$(HOLD$,LEN(HOLD$)-1):GOTO 14080
14160 IF ASC(I$)=13 THEN 14230
14170 XO=XO+1
14180 HOLD$=HOLD$+I$
```

```
14190 COLOR K
14200 LOCATE Y+YO,X+XO-1
14210 PRINT I$
14220 GOTO 14080
14230 HOLD$=RIGHT$(HOLD$,XO)
14240 RETURN
14250 REM Converts to lower case.
14260 REM Requires HOLD$, returns HOLD$
14270 FOR I=1 TO LEN(HOLD$)
14280   IF MID$(HOLD$,I,1)>="A" AND MID$(HOLD$,I,1)<="Z" THEN MID$(HOLD$,I,1)=CHR$(ASC(MID$(HOLD$,I,1))+32)
14290 NEXT I
14300 RETURN
15000 REM Caps routine
15010 IF LEFT$(WORD$,1)>="a" AND LEFT$(WORD$,1)<="z" THEN MID$(WORD$,1,1)=CHR$(ASC(LEFT$(WORD$,1))-32)
15020 RETURN
20000 REM Save Routine
20001 SVE=1:'rem Flags that the program is in Save mode.
20010 GOSUB 21000
20020 K=10:X=22:Y=11
20030 GOSUB 14000:GOSUB 13250
20040 IF HOLD$<>"yes" AND HOLD$<>"y" THEN run "menu"
20050 GOSUB 23000
20060 K=11:X=7:Y=16
20070 GOSUB 14000:GOSUB 13250:DOCTOR$=HOLD$
20080 SEARCH$=HOLD$:GOSUB 9000
20090 IF MATCH=0 THEN BEEP:LOCATE 16,7:PRINT SPACE$(60):GOTO 20060
20100 X=7:Y=19
20110 GOSUB 14000:DTE$=HOLD$:ISSUE$=HOLD$
20120 GOSUB 5000
20130 IF MATCH=0 THEN BEEP:LOCATE 19,7:PRINT SPACE$(60):GOTO 20100
20140 X=7:Y=22
20150 GOSUB 14000:GOSUB 13250
20160 MAHL$=HOLD$
20170 GOSUB 22000
20180 run "menu"
21000 REM Verify save screen
21010 CLS: COLOR 7, 0: PRINT "                                                                        ";
21020 PRINT "                                                                        ";
21030 PRINT " +----------------------------------------------------------------------+ ";
21040 PRINT " ⁿ";: COLOR 28, 0: PRINT "Warning! Warning! Warning! Warning! Warning! Warning! Warning! Warning!";
21050 COLOR 7, 0: PRINT " ⁿ   ";: PRINT "  ⁿ                                                                    ⁿ  ";
21060 PRINT "  ⁿ                                                                       ";
21070 COLOR 10, 0: PRINT "  ";: COLOR 7, 0: PRINT "                                              ⁿ    ";
21080 COLOR 10, 0: PRINT "  ";: COLOR 7, 0: PRINT "  ⁿ                                                                    ⁿ  ";
21090 COLOR 10, 0: PRINT "  ";: COLOR 7, 0: PRINT "ⁿ                                                                     ⁿ  ";
21100 PRINT "  ⁿ ";: COLOR 10, 0: PRINT "Saving the current modifications will overwrite information on the";
21110 COLOR 7, 0: PRINT "   ⁿ ";: PRINT "  ⁿ ";
```

```
21120 COLOR 10, 0: PRINT "the patient's portable medical record.  Do you wish to save your ";
21130 COLOR 7, 0: PRINT "    ▫    ";: PRINT "    ▫    ";
21140 COLOR 10, 0: PRINT "modifications?                               ";
21150 COLOR 7, 0: PRINT "           ▫    ";: PRINT "    ▫    ▫    ";
21160 PRINT "    ▫                                                    ▫    ";
21170 PRINT "    ▫                                                    ▫    ";
21180 PRINT "    ▫                                                    ▫    ";
21190 PRINT "    ▫";:  COLOR 28, 0: PRINT "Warning! Warning! Warning! Warning! Warning! Warning! Warning! Warning!";
21200 COLOR 7, 0: PRINT "▫    ";: PRINT " +------------------------------------------------------------------+   ";
21210 COLOR 7, 0
21220 RETURN
22000 REM Output routine
22001 CLOSE #1
22010 OPEN "o",#1,"text.dat"
22020 PRINT #1,VERSION:CNT=CNT+1
22030 PRINT #1,GENDER$:CNT=CNT+1
22040 PRINT #1,RACE$
22050 PRINT #1,DOB$:CNT=CNT+3
22060 PRINT #1,AREA:CNT=CNT+2
22070 PRINT #1,PHONE:CNT=CNT+4
22080 PRINT #1,PMH:CNT=CNT+1
22090 FOR I=1 TO PMH
22100    PRINT #1,PMH$(I):CNT=CNT+4
22110    PRINT #1,PMHDATE$(I):CNT=CNT+3
22120    PRINT #1,PMHCNT$(I):CNT=CNT+4
22130    PRINT #1,PMHMD$(I):CNT=CNT+4
22140 NEXT I
22150 PRINT #1,PSH:CNT=CNT+1
22160 FOR I=1 TO PSH
22170    PRINT #1,PSH$(I):CNT=CNT+4
22180    PRINT #1,PSHDATE$(I):CNT=CNT+3
22190    PRINT #1,PSHCNT$(I):CNT=CNT+4
22200    PRINT #1,PSHMD$(I):CNT=CNT+4
22210 NEXT I
22220 PRINT #1,MEDS:CNT=CNT+1
22230 FOR I=1 TO MEDS
22240    PRINT #1,MED$(I):CNT=CNT+4
22250    PRINT #1,MEDDATE$(I):CNT=CNT+3
22260    PRINT #1,MEDDOSE$(I):CNT=CNT+4
22270    PRINT #1,MEDMD$(I):CNT=CNT+4
22280 NEXT I
22290 PRINT #1,ALLERGY:CNT=CNT+1
22300 FOR I=1 TO ALLERGY
22310    PRINT #1,ALLERGY$(I):CNT=CNT+4
22320 NEXT I
22330 PRINT #1,IMMUNE:CNT=CNT+1
22340 FOR I=1 TO IMMUNE
22350    PRINT #1,IMMUNE$(I):CNT=CNT+4
22360    PRINT #1,IMMDATE$(I):CNT=CNT+3
22370 NEXT I
```

```
22380 PRINT #1,SCRN:CNT=CNT+1
22390 FOR I=1 TO SCRN
22400   PRINT #1,SCRN$(I):CNT=CNT+4
22410   PRINT #1,SCRNDATE$(I):CNT=CNT+3
22420   PRINT #1,SCRNCNT$(I):CNT=CNT+4
22430 NEXT I
22440 PRINT #1,LIVING$:CNT=CNT+1
22450 PRINT #1,ORGAN$
22460 PRINT #1,COMMENT:CNT=CNT+1
22470 FOR I=1 TO COMMENT
22480   PRINT #1,COMMENT$(I):CNT=CNT+4
22490 NEXT I
22500 PRINT #1,DOCTOR$:CNT=CNT+4
22510 PRINT #1,ISSUE$:CNT=CNT+3
22511 PRINT #1,MAHL$:CNT=CNT+4
22520 CLOSE #1
22530 RETURN
23000 REM Patient mother's maiden name, physician and date of issue.
23010 CLS: COLOR 7, 0: PRINT "           ";
23020 COLOR 14, 0: PRINT " ";: COLOR 7, 0: PRINT "      ";
23030 COLOR 14, 0: PRINT "Patient Data Inventory ";
23040 COLOR 7, 0: PRINT "   ";: COLOR 14, 0: PRINT "       ";
23050 COLOR 8, 0: PRINT "                ";
23060 COLOR 7, 0: PRINT "              ";
23070 COLOR 8, 0: PRINT "      ";: COLOR 7, 0: PRINT "+";
23080 COLOR 3, 0: PRINT "Instructions";: COLOR 7, 0: PRINT "---------------------------------+      ";
23090 COLOR 8, 0: PRINT "     ";: COLOR 7, 0: PRINT "ª";
23100 COLOR 8, 0: PRINT "      ";
23110 COLOR 11, 0: PRINT "    ";: COLOR 7, 0: PRINT "         ª     ";
23120 COLOR 8, 0: PRINT "      ";: COLOR 7, 0: PRINT "ª";
23130 COLOR 8, 0: PRINT " ";: COLOR 3, 0: PRINT "Please enter the name of the issuing physician,";
23140 COLOR 7, 0: PRINT " ª         ";: COLOR 8, 0: PRINT "     ";
23150 COLOR 7, 0: PRINT "ª";: COLOR 8, 0: PRINT " ";
23160 COLOR 3, 0: PRINT "today's date (mo/day/year), and the name of the";
23170 COLOR 7, 0: PRINT " ª        ";: COLOR 8, 0: PRINT "  ";
23180 COLOR 7, 0: PRINT "   ª ";: COLOR 3, 0: PRINT "patient's mother's maiden name. ";
23190 COLOR 7, 0: PRINT "     ª      ";
23200 COLOR 8, 0: PRINT "  ";: COLOR 7, 0: PRINT "    ª              ª";
23210 COLOR 8, 0: PRINT "  ";: COLOR 7, 0: PRINT "    ª ";
23220 COLOR 3, 0: PRINT "If the patient's mother's maiden name is not";
23230 COLOR 7, 0: PRINT "  ª      ";
23240 COLOR 8, 0: PRINT "  ";: COLOR 7, 0: PRINT "    ª ";
23250 COLOR 3, 0: PRINT "known, instruct the patient to select another ";
23260 COLOR 7, 0: PRINT " ª       ";: COLOR 8, 0: PRINT "  ";
23270 COLOR 7, 0: PRINT "    ª ";: COLOR 3, 0: PRINT "name for use in the authentication procedure.";
23280 COLOR 7, 0: PRINT " ª     ";
23290 COLOR 8, 0: PRINT "  ";: COLOR 7, 0: PRINT "    ª            ª";
23300 COLOR 8, 0: PRINT "  ";: COLOR 7, 0: PRINT "    ª            ª";
```

```
23310 PRINT " ";: COLOR 8, 0: PRINT " ";: COLOR 7, 0: PRINT "      +---------------------------
-------------------+          ";
23320 PRINT " ";: COLOR 8, 0: PRINT " ";: COLOR 7, 0: PRINT "+";
23330 COLOR 3, 0: PRINT "Physician";: COLOR 7, 0: PRINT "-------------------------------------
-----------------------+   ";
23340 PRINT " ";: COLOR 8, 0: PRINT " ";: COLOR 7, 0: PRINT "¤";
23350 COLOR 11, 0: PRINT "        ";: COLOR 7, 0: PRINT "                                        ";
23360 COLOR 11, 0: PRINT "        ";: COLOR 8, 0: PRINT "¤";
23370 COLOR 7, 0: PRINT "   ";: PRINT "   ";: COLOR 8, 0: PRINT "+----------------------------
---------------------------------+";
23380 COLOR 7, 0: PRINT "   ";: PRINT "   +";
23390 COLOR 3, 0: PRINT "Today's Date";: COLOR 7, 0: PRINT "-------------------------------
---------------------+   ";
23400 PRINT "   ¤";: COLOR 11, 0: PRINT "                                                      ";
23410 COLOR 8, 0: PRINT "¤";: COLOR 7, 0: PRINT "   ";
23420 PRINT "   ";: COLOR 8, 0: PRINT "+---------------------------------------------------------
------------+";
23430 COLOR 7, 0: PRINT "   ";: PRINT "   +";
23440 COLOR 3, 0: PRINT "Patient's Mother's Maiden Name";
23450 COLOR 7, 0: PRINT "---------------------------------------+    ";
23460 COLOR 3, 0: PRINT "   ";: COLOR 7, 0: PRINT "¤";
23470 COLOR 11, 0: PRINT "                                                                  ";
23480 COLOR 8, 0: PRINT "¤";: COLOR 7, 0: PRINT "   ";
23490 COLOR 3, 0: PRINT "   ";: COLOR 8, 0: PRINT "+-----------------------------------------
--------------------+";
23500 COLOR 7, 0
23510 RETURN
```

Report Utility

Filename: REPORT.BAS

```
10 REM Report Utility
20 REM This program reads the Text.Dat file and converts it into a Text.OUT file
30 REM Created by S.Behram
40 REM
50 REM
60 CLS
70 OPEN "I",#1,"text.dat"
80 OPEN "o",#2,"text.out"
90 PRINT #2, "           Vital Access (tm)
100 PRINT #2, "          Portable Medical Record
110 PRINT #2,
120 PRINT #2, "    Copyright University of Maryland at College Park"
130 PRINT #2,
140 PRINT #2,
150 PRINT #2, "1.  Demographic Information"
155 PRINT #2,
160 INPUT #1,VERSION
170 INPUT #1,GENDER$:WORD$=GENDER$:GOSUB 5000
180 PRINT #2, "Gender: ";WORD$
190 PRINT #2, "Race  : ";
200 INPUT #1,RACE$ :WORD$=RACE$ :GOSUB 5000
210 PRINT #2, WORD$
```

```
220 PRINT #2, "Date of Birth: ";
230 INPUT #1,DOB$
240 PRINT #2, DOB$
245 PRINT #2,
250 PRINT #2, "Emergency contact: ";
260 INPUT #1,AREA
270 PRINT #2, USING "(###)";AREA;
271 INPUT #1,PHONE
272 PRINT #2, USING "###-####";PHONE
280 PRINT #2,
290 PRINT #2, "II.  Past Medical History"
300 INPUT #1,PMH
310 FOR I=1 TO PMH
320     INPUT #1,PMH$:WORD$=PMH$:GOSUB 5000:PMH$=WORD$
330     INPUT #1,PMHDATE$
340     INPUT #1,PMHCNT$:WORD$=PMHCNT$:GOSUB 5000:PMHCNT$=WORD$
350     INPUT #1,PMHMD$:WORD$=PMHMD$:GOSUB 5000:PMHMD$="Dr."+WORD$
360     PRINT #2, ,CHR$(64+I);". "+PMH$
370     PRINT #2, ,"  Date:   ";PMHDATE$
380     PRINT #2, ,"  Center: ";PMHCNT$
390     PRINT #2, ,"  MD:     ";PMHMD$
400     PRINT #2,
410 NEXT I
420 PRINT #2,
430 PRINT #2, "III.  Past Surgical History"
440 INPUT #1,PSH
450 FOR I=1 TO PSH
460     INPUT #1,PSH$:WORD$=PSH$:GOSUB 5000:PSH$=WORD$
470     INPUT #1,PSHDATE$
480     INPUT #1,PSHCNT$:WORD$=PSHCNT$:GOSUB 5000:PSHCNT$=WORD$
490     INPUT #1,PSHMD$:WORD$=PSHMD$:GOSUB 5000:PSHMD$=WORD$
500     PRINT #2, ,CHR$(64+I);". "+PSH$
510     PRINT #2, ,"  Date:   ";PSHDATE$
520     PRINT #2, ,"  Center: ";PSHCNT$
530     PRINT #2, ,"  MD:     ";PSHMD$
540     PRINT #2,
550 NEXT I
590 PRINT #2,
600 PRINT #2, "IV. Medications"
610 INPUT #1,MED
620 FOR I=1 TO MED
630     INPUT #1,MED$:WORD$=MED$:GOSUB 5000:MED$=WORD$
640     INPUT #1,MEDDATE$
650     INPUT #1,MEDDOSE$:WORD$=MEDDOSE$:GOSUB 5000:PSHCNT$=MEDDOSE$
660     INPUT #1,MEDMD$:WORD$=MEDMD$:GOSUB 5000:MEDMD$=WORD$
670     PRINT #2, ,CHR$(64+I);". "+MED$
680     PRINT #2, ,"  Date:   ";MEDDATE$
690     PRINT #2, ,"  Dose:   ";PSHCNT$
700     PRINT #2, ,"  MD:     ";MEDMD$
710     PRINT #2,
720 NEXT I
730 PRINT #2,
740 PRINT #2, "V.  Allergies"
750 INPUT #1,ALLERGY
```

```
760 FOR I=1 TO ALLERGY
770     INPUT #1,ALLERGY$:WORD$=ALLERGY$:GOSUB 5000:ALLERGY$=WORD$
780     PRINT #2, ,CHR$(64+I);". "+ALLERGY$
790     PRINT #2,
800 NEXT I
810 PRINT #2,
815 PRINT #2, "VI.  Immunizations"
820 INPUT #1,IMMUNE
830 FOR I=1 TO IMMUNE
840     INPUT #1,IMM$:WORD$=IMM$:GOSUB 5000:IMM$=WORD$
850     INPUT #1,IMMDATE$
860     PRINT #2, ,CHR$(64+I);". ";IMM$
870     PRINT #2, ,"Date:     ";IMMDATE$
880     PRINT #2,
890 NEXT I
895 PRINT #2,
900 PRINT #2, "VII.  Screening Procedures"
910 INPUT #1,SCRN
920 FOR I=1 TO SCRN
930     INPUT #1,SCRN$:WORD$=SCRN$:GOSUB 5000:SCRN$=WORD$
940     INPUT #1,SCRNDATE$
950     INPUT #1,SCRNCNT$:WORD$=SCRNCNT$:GOSUB 5000:SCRNCNT$=WORD$
960     REM INPUT #1,PMHMD$:WORD$=PMHMD$:GOSUB 5000:PMHMD$="Dr."+WORD$
970     PRINT #2, ,CHR$(64+I);". "+SCRN$
980     PRINT #2, ,"  Date:   ";SCRNDATE$
990     PRINT #2, ,"  Center: ";SCRNCNT$
1000    REM print #2, ," MD:    ";PMHMD$
1010    PRINT #2,
1020 NEXT I
1030 PRINT #2,
1040 PRINT #2, "VIII.  Living Will Status: ";
1050 INPUT #1,LIVING$
1060 WORD$=LIVING$:GOSUB 5000:LIVING$=WORD$:PRINT #2, LIVING$
1070 PRINT #2,
1075 PRINT #2,
1080 PRINT #2, "IX.  Organ Donor Status: ";
1090 INPUT #1,ORGAN$
1100 WORD$=ORGAN$:GOSUB 5000:ORGAN$=WORD$:PRINT #2, ORGAN$
1110 PRINT #2,
1120 PRINT #2, "X.  Special Comments"
1121 PRINT #2,
1130 INPUT #1,COMMENT
1140 FOR I=1 TO COMMENT
1160 INPUT #1,COMMENT$
1161 IF V=0 THEN V=1:WORD$=COMMENT$:GOSUB 5000:COMMENT$=WORD$
1162 PRINT #2, COMMENT$;" ";
1170 IF COMMENT$="." THEN E=1 ELSE E=0
1171 IF E=1 THEN PRINT #2,:E=0:V=0
1173 NEXT I
1200 INPUT #1,DOCTOR$:WORD$=DOCTOR$:GOSUB 5000:DOCTOR$="Dr."+WORD$
1205 INPUT #1,D$
1206 PRINT #2,
1207 PRINT #2, "                     *** End of Summary   ***
1208 PRINT #2,:PRINT #2,
```

```
1210 PRINT #2,
1215 PRINT #2, "Issuing Physician: ";DOCTOR$
1220 PRINT #2, "Issuing Date:      ";D$
1240 INPUT #1,VER$
1241 PRINT #2,:PRINT #2,
1250 PRINT #2, "Note:  Always verify the authenticity code by asking the patient for mother's"
1260 PRINT #2, "      maiden name."
1270 PRINT #2,
1280 PRINT #2, "                          Authentication Code: ";:WORD$=VER$:GOSUB
5000:VER$=WORD$:PRINT #2, VER$
1290 PRINT #2,
1300 PRINT #2, "                *** Termination of Report ***"
1400 CLS:KEY OFF:COLOR 7
1402 COLOR 11:LOCATE 12,20
1403 PRINT "Report generated to output file: TEXT.OUT"
1404 COLOR 10
1405 ZZ=TIMER
1406 ZZZ=TIMER:IF ZZZ<ZZ+2 THEN 1406
1500 LOCATE 16,2
1510 COLOR 3
1520 PRINT "Do you want this file to be sent to the printer (y/n)";
1530 INPUT A$
1540 IF A$<>"y" AND A$<>"Y" THEN 2000
1550 LOCATE 17,2
1560 PRINT "Is the printer ONLINE";
1570 INPUT A$:IF A$<>"y" AND A$<>"Y" THEN CLS:GOTO 1500
1580 SHELL "print text.out"
1590 ZZ=TIMER
1600 ZZZ=TIMER:IF ZZZ<ZZ+3 THEN 1600:' 3 second delay for shell.
2000 RUN "menu"
5000 REM Caps routine
5010 IF LEFT$(WORD$,1)>="a" AND LEFT$(WORD$,1)<="z" THEN
MID$(WORD$,1,1)=CHR$(ASC(LEFT$(WORD$,1))-32)
5020 RETURN
```

Card Utility

Filename:  CARD.BAS

```
10 REM Card
20 REM This utility generates an ASCII file containing the card information
30 REM S.Behram
40 REM 10/24/93
50 REM
55 CLS:KEY OFF
60 OPEN "r",#1,"update.inf",1
70 FIELD #1,1 AS C$
71 OPEN "o",#2,"card.out"
80 COLUMN$=""
81 COLOR 27
82 LOCATE 12,35
83 PRINT "Working..."
90 FOR I=1 TO 14
100    COLUMN$="":H=0:V=0
```

```
110     FOR T=1 TO 40
120         CNT=CNT+1
130         GET #1,CNT
140         COLUMN$=COLUMN$+C$
150         H=H+ASC(C$)*T
160         V=V+ASC(C$)*(I+1)
170     NEXT T
180     IF H>99 THEN H=H-99:GOTO 180
190     IF V>99 THEN V=V-99:GOTO 190
200     PRINT #2,COLUMN$,:PRINT #2, USING "##";H;:PRINT " ";:PRINT #2,USING "##";V
210 NEXT I
220 LOCATE 15,15
230 COLOR 11
240 PRINT "Card information printed to ouput file:  CARD.OUT"
250 COLOR 3
260 PRINT:PRINT
270 PRINT "Do you wish to print this card to printer (y/n)";
280 INPUT A$
290 IF A$<>"y" AND A$<>"Y" THEN 350
300 PRINT "Please insure printer is setup and online, then hit RETURN";
310 INPUT A$
320 SHELL "print card.out"
330 ZZ=TIMER
340 ZZZ=TIMER:IF ZZZ<ZZ+5 THEN 340
350 RUN "menu"
```

Main Menu Manager

Filename: MENU.BAS

```
10 ' Initial Menu for the portable medical information system.
20 ' Allows access to select system programs.
30 '
40 ' Created by S. Behram & N. Grauzlis & S. Joseph
50 ' Copyright (c) UMCP
60 ' All rights reserved.
70 '
80 '
90 SCREEN 0:CLS:KEY OFF
100 GOSUB 270
110 I$=INKEY$
120 IF I$="" THEN 110
130 REM
140 IF I$<"1" OR I$>"9" THEN 110
141 ZZ=TIMER:LOCATE 18,35:COLOR 1:PRINT "Loading..."
142 ZZZ=TIMER:IF ZZZ<ZZ+2 THEN 142
143 Z$=INKEY$:IF Z$<>"" THEN 143
150 I=VAL(I$)
151 COLOR 25
152 LOCATE 18,35:PRINT "Loading..."
160 ON I GOTO 180,190,200,210,220,230,240,250,260
170 STOP
180 RUN "manual"
190 RUN "manual1"
```

```
200 RUN "decomp"
210 RUN "report"
220 RUN "card"
230 RUN "comp"
240 RUN "warning"
250 RUN "invent"
260 CLS:SYSTEM
270 REM Screen
280 REM
290 REM
300 CLS: COLOR 7, 0: PRINT "                        ";
310 COLOR 9, 0: PRINT "                        ";
320 COLOR 7, 0: PRINT " ";: COLOR 14, 0: PRINT "  ";
330 COLOR 7, 0: PRINT "                        ";
340 PRINT "            ";: COLOR 9, 0: PRINT "            ";
350 COLOR 7, 0: PRINT "                        ";
360 PRINT "            ";: COLOR 14, 0: PRINT " ";
370 COLOR 7, 0: PRINT " ";: COLOR 14, 0: PRINT " Portable Medical Record";
380 COLOR 7, 0: PRINT "                        ";
390 PRINT "    ";: COLOR 15, 0: PRINT "+";: COLOR 3, 0: PRINT "Options";
400 COLOR 7, 0: PRINT "---------------------------------------------------------------+   ";
410 PRINT "    ¤                                                         ";
420 COLOR 8, 0: PRINT "¤";: COLOR 7, 0: PRINT "   ";
430 PRINT "   ¤ ";: COLOR 9, 0: PRINT "1.  Manual Data Entry Module ";
440 COLOR 7, 0: PRINT "                        ";
450 COLOR 8, 0: PRINT "¤";: COLOR 7, 0: PRINT "   ";
460 PRINT "   ¤ ";: COLOR 9, 0: PRINT "2.  Disk Data Entry Module";
470 COLOR 7, 0: PRINT " ";: COLOR 9, 0: PRINT "   ";
480 COLOR 7, 0: PRINT "                        ";
490 COLOR 8, 0: PRINT "¤";: COLOR 7, 0: PRINT "   ";
500 PRINT "   ¤ ";: COLOR 9, 0: PRINT "3.  Decompression Utility";
510 COLOR 7, 0: PRINT "                        ";
520 COLOR 8, 0: PRINT "¤";: COLOR 7, 0: PRINT "   ";
530 PRINT "   ¤ ";: COLOR 9, 0: PRINT "4.  Report Utility";
540 COLOR 7, 0: PRINT "                        ";
550 COLOR 8, 0: PRINT "¤";: COLOR 7, 0: PRINT "   ";
560 PRINT "   ¤ ";: COLOR 9, 0: PRINT "5.  Card Utility         ";
570 COLOR 8, 0: PRINT "  ";: COLOR 9, 0: PRINT " ";
580 COLOR 7, 0: PRINT "  ";: COLOR 8, 0: PRINT "  ";
590 COLOR 7,0 : PRINT "  ";: COLOR 7, 0: PRINT "                        ";
600 COLOR 8, 0: PRINT "¤ ";: COLOR 7, 0: PRINT "  ";
610 COLOR 8, 0: PRINT "  ";: COLOR 7, 0: PRINT "     ¤ ";
620 COLOR 9, 0: PRINT "6.  Compression Utility";
630 COLOR 7, 0: PRINT "                        ";
640 COLOR 8, 0: PRINT "¤";: COLOR 7, 0: PRINT "   ";
650 PRINT "   ¤ ";: COLOR 9, 0: PRINT "7.  Update Module";
660 COLOR 7, 0: PRINT "                        ";
670 COLOR 8, 0: PRINT "¤";: COLOR 7, 0: PRINT "   ";
680 PRINT "   ¤ ";: COLOR 9, 0: PRINT "8.  Patient Data Inventory";
690 COLOR 7, 0: PRINT "                        ";
700 COLOR 8, 0: PRINT "¤";: COLOR 7, 0: PRINT "   ";
710 PRINT "   ¤ ";:COLOR 9, 0: PRINT "9.  Quit                                   ";
720 COLOR 8, 0: PRINT "¤";: COLOR 7, 0: PRINT "   ";
```

```
730 PRINT "    ";: COLOR 8, 0: PRINT "+-------------------------------------------------------------
----------+";
740 LOCATE 21,12:COLOR 10
750 PRINT "Copyright (c) University of Maryland at College Park."
760 LOCATE 22,31
770 PRINT "All rights reserved."
780 COLOR 7, 0
790 RETURN
```

Decompression Utility

Filename: DECOMP.BAS

```
10 REM Decompression Utility
20 REM
30 REM
40 REM V.1.0
50 REM
60 REM S. Behram / N. Grauzlis / S.W. Joseph
70 REM
75 NXT=10000
76 CONVERT=11000
77 FETCH=14000
80 GOSUB 13000:'Screen set-up
90 K=11
100 X=20:Y=11
110 GOSUB 4000:'Modified input -- will not display output to screen.
111 WORD$=HOLD$
120 GOSUB 4500:'Convert to lowercase
121 LOCATE 7,18:COLOR 9:PRINT"Please re-enter authorization code to verify."
122 K=11:X=20:Y=11:GOSUB 4000:GOSUB 4500
123 IF WORD$<>HOLD$ THEN BEEP:BEEP:RUN
124 COLOR 17:LOCATE 7,18:S=TIMER
125 PRINT "Please re-enter authorization code to verify."
126 IF TIMER<S+2 THEN 126
127 LOCATE 7,18
128 PRINT "                                             "
130 REM Using the Authorization Password stored in HOLD$
140 REM software will derive unique values for OFFSET and SHIFT
150 FOR I=1 TO LEN(HOLD$)
160 OFFSET=OFFSET+ASC(MID$(HOLD$,I,1))
165 NEXT I
170 IF OFFSET>255 THEN OFFSET=OFFSET-256:GOTO 170
180 LAST$=RIGHT$(HOLD$,1)
190 SHIFT=ASC(LAST$)
195 IF SHIFT>61 THEN SHIFT=SHIFT-62:GOTO 195
200 REM SHIFT and OFFSET variables have been calculated
210 REM Data can now be read from the decimal input file.
220 REM The interpretation of this data will be format dependent.
230 REM This means that if PMR is released for other purposes, ie,
240 REM PMR for OB/GYN, this module will have to be modified
250 REM in order to read the information correctly.
251 OPEN "r",#1,"vll.dat",1
```

```
252 OPEN "r",#2,"vll.lnk",6
253 FIELD #2,3 AS SA$,3 AS L$
254 FIELD #1,1 AS C$
260 REM
262 OPEN "r",#3,"decimal.dat",8
263 FIELD #3,8 AS DECIMAL$
264 POINTER=OFFSET
270 REM Read form beginning here.
280 GOSUB 10000:'Get 1st address -- Version Number
290 DEC1=JUMP:GOSUB 11000
300 VERSION=DECIMAL
310 GOSUB 10000:'gender & race
320 DEC1=JUMP:GOSUB 11000
321 GENDER$="not specified":RACE$="not specified"
330 IF DECIMAL=1 THEN RACE$="white":GENDER$="male"
340 IF DECIMAL=2 THEN GENDER$="female":RACE$="white"
350 IF DECIMAL=3 THEN GENDER$="male":RACE$="african american"
360 IF DECIMAL=4 THEN GENDER$="female":RACE$="african american"
370 IF DECIMAL=5 THEN GENDER$="male":RACE$="hispanic"
380 IF DECIMAL=6 THEN GENDER$="female":RACE$="hispanic"
390 IF DECIMAL=7 THEN GENDER$="male":RACE$="american indian"
400 IF DECIMAL=8 THEN GENDER$="female":RACE$="american indian"
410 IF DECIMAL=9 THEN GENDER$="male":RACE$="asian"
420 IF DECIMAL=10 THEN GENDER$="female":RACE$="asian"
430 IF DECIMAL=11 THEN GENDER$="male":RACE$="not specified"
440 IF DECIMAL=12 THEN GENDER$="female":RACE$="not specified"
450 IF DECIMAL=13 THEN GENDER$="not specified":RACE$="not specified"
460 IF DECIMAL=14 THEN GENDER$="sex of rearing differs from genotype":RACE$="not specified"
470 IF DECIMAL=15 THEN RACE$="white"
480 IF DECIMAL=16 THEN RACE$="non-white"
490 IF DECIMAL=17 THEN RACE$="african american"
500 IF DECIMAL=18 THEN RACE$="american indian"
510 IF DECIMAL=19 THEN RACE$="asian"
520 IF DECIMAL=20 THEN RACE$="hispanic"
530 GOSUB 10000:'get Date of Birth
540 DEC3=JUMP
550 GOSUB 10000
560 DEC2=JUMP
570 GOSUB 10000
580 DEC1=JUMP
590 GOSUB 12000
591 DOB$=STR$(MONTH)+"/"+STR$(DAYS)+"/"+STR$(YEAR)
600 GOSUB 10000:'get phone number
610 DEC2=JUMP
620 GOSUB 10000
630 DEC1=JUMP
640 GOSUB 11000
650 AREA=DECIMAL
660 GOSUB 10000
670 DEC4=JUMP
680 GOSUB 10000
690 DEC3=JUMP
700 GOSUB 10000
```

```
710 DEC2=JUMP
720 GOSUB 10000
730 DEC1=JUMP
740 GOSUB 11000
750 PHONE=DECIMAL
760 GOSUB 10000:'# PMHx entries
770 DEC1=JUMP:GOSUB 11000
780 PMH=DECIMAL
790 DIM PMH$(PMH),PMHDATE$(PMH),PMHCNT$(PMH),PMHMD$(PMH)
800 FOR II=1 TO PMH
810    GOSUB 10000
820    DEC4=JUMP
830    GOSUB 10000
840    DEC3=JUMP
850    GOSUB 10000
860    DEC2=JUMP
870    GOSUB 10000
880    DEC1=JUMP
890    GOSUB 11000
900    ADDRESS=DECIMAL
910    GOSUB 14000
920    PMH$(II)=WORD$
930    GOSUB 10000:'get date
940    DEC3=JUMP
950    GOSUB 10000
960    DEC2=JUMP
970    GOSUB 10000
980    DEC1=JUMP
990    GOSUB 12000:'rem calculate date
1000   PMHDATE$(II)=STR$(MONTH)+"/"+STR$(DAYS)+"/"+STR$(YEAR)
1010   GOSUB 10000:'get center name
1020   DEC4=JUMP
1030   GOSUB 10000
1040   DEC3=JUMP
1050   GOSUB 10000
1060   DEC2=JUMP
1070   GOSUB 10000
1080   DEC1=JUMP
1090   GOSUB 11000
1100   ADDRESS=DECIMAL
1110   GOSUB 14000
1120   PMHCNT$(II)=WORD$
1130   GOSUB 10000:'get MD
1140   DEC4=JUMP
1150   GOSUB 10000
1160   DEC3=JUMP
1170   GOSUB 10000
1180   DEC2=JUMP
1181 GOSUB 10000
1182 DEC1=JUMP
1190   GOSUB 11000
1200   ADDRESS=DECIMAL
1210   GOSUB 14000
1220   PMHMD$(II)=WORD$
```

```
1230 NEXT II
1500 GOSUB 10000:'# PSHx entries
1510 DEC1=JUMP:GOSUB 11000
1520 PSH=DECIMAL
1530 DIM PSH$(PSH),PSHDATE$(PSH),PSHCNT$(PSH),PSHMD$(PSH)
1540 FOR II=1 TO PSH
1550    GOSUB 10000
1560    DEC4=JUMP
1570    GOSUB 10000
1580    DEC3=JUMP
1590    GOSUB 10000
1600    DEC2=JUMP
1610    GOSUB 10000
1620    DEC1=JUMP
1630    GOSUB 11000
1640    ADDRESS=DECIMAL
1650    GOSUB 14000
1660    PSH$(II)=WORD$
1670    GOSUB 10000:'get date
1680    DEC3=JUMP
1690    GOSUB 10000
1700    DEC2=JUMP
1710    GOSUB 10000
1720    DEC1=JUMP
1730    GOSUB 12000:'rem calculate date
1740    PSHDATE$(II)=STR$(MONTH)+"/"+STR$(DAYS)+"/"+STR$(YEAR)
1750    GOSUB 10000:'get center name
1760    DEC4=JUMP
1770    GOSUB 10000
1780    DEC3=JUMP
1790    GOSUB 10000
1800    DEC2=JUMP
1810    GOSUB 10000
1820    DEC1=JUMP
1830    GOSUB 11000
1840    ADDRESS=DECIMAL
1850    GOSUB 14000
1860    PSHCNT$(II)=WORD$
1870    GOSUB 10000:'get MD
1880    DEC4=JUMP
1890    GOSUB 10000
1900    DEC3=JUMP
1910    GOSUB 10000
1920    DEC2=JUMP
1921 GOSUB 10000
1922 DEC1=JUMP
1930    GOSUB 11000
1940    ADDRESS=DECIMAL
1950    GOSUB 14000
1960    PSHMD$(II)=WORD$
1970 NEXT II
2000 GOSUB 10000:'# med entries
2010 DEC1=JUMP:GOSUB 11000
2020 MED=DECIMAL
```

```
2030 DIM MED$(MED),MEDDATE$(MED),MEDDOSE(MED),MEDMD(MED)
2040 FOR II=1 TO MED
2050     GOSUB 10000
2060     DEC4=JUMP
2070     GOSUB 10000
2080     DEC3=JUMP
2090     GOSUB 10000
2100     DEC2=JUMP
2110     GOSUB 10000
2120     DEC1=JUMP
2130     GOSUB 11000
2140     ADDRESS=DECIMAL
2150     GOSUB 14000
2160     MED$(II)=WORD$
2170     GOSUB 10000:'get date
2180     DEC3=JUMP
2190     GOSUB 10000
2200     DEC2=JUMP
2210     GOSUB 10000
2220     DEC1=JUMP
2230     GOSUB 12000:'rem calculate date
2240     MEDDATE$(II)=STR$(MONTH)+"/"+STR$(DAYS)+"/"+STR$(YEAR)
2250     GOSUB 10000:'get center name
2260     DEC4=JUMP
2270     GOSUB 10000
2280     DEC3=JUMP
2290     GOSUB 10000
2300     DEC2=JUMP
2310     GOSUB 10000
2320     DEC1=JUMP
2330     GOSUB 11000
2340     ADDRESS=DECIMAL
2350     GOSUB 14000
2360     MEDDOSE$(II)=WORD$
2370     GOSUB 10000:'get MD
2380     DEC4=JUMP
2390     GOSUB 10000
2400     DEC3=JUMP
2410     GOSUB 10000
2420     DEC2=JUMP
2421 GOSUB 10000
2422 DEC1=JUMP
2430     GOSUB 11000
2440     ADDRESS=DECIMAL
2450     GOSUB 14000
2460     MEDMD$(II)=WORD$
2470 NEXT II
2480 REM Allergies
2500 GOSUB 10000:'rem get number of allergies
2510 DEC1=JUMP
2520 GOSUB 11000
2530 ALLERGY=DECIMAL
2540 DIM ALLERGY$(ALLERGY)
2550 FOR II=1 TO ALLERGY
```

```
2560    GOSUB 10000:'get allergy
2570    DEC4=JUMP
2580    GOSUB 10000
2590    DEC3=JUMP
2600    GOSUB 10000
2610    DEC2=JUMP
2620    GOSUB 10000
2630    DEC1=JUMP
2640    GOSUB 11000
2650    ADDRESS=DECIMAL
2660    GOSUB 14000
2670    ALLERGY$(II)=WORD$
2680 NEXT II
2700 GOSUB 10000:'rem get number of immunizations
2710 DEC1=JUMP
2720 GOSUB 11000
2730 IMMUNE =DECIMAL
2740 DIM IMMUNE$(IMMUNE),IMMDATE$(IMMUNE)
2750 FOR II=1 TO IMMUNE
2760    GOSUB 10000:'get allergy
2770    DEC4=JUMP
2780    GOSUB 10000
2790    DEC3=JUMP
2800    GOSUB 10000
2810    DEC2=JUMP
2820    GOSUB 10000
2830    DEC1=JUMP
2840    GOSUB 11000
2850    ADDRESS=DECIMAL
2860    GOSUB 14000
2870    IMMUNE$(II)=WORD$
2871            'get date
2872    GOSUB 10000:DEC3=JUMP
2873    GOSUB 10000:DEC2=JUMP
2874    GOSUB 10000:DEC1=JUMP
2875    GOSUB 12000
2876    IMMDATE$(II)=STR$(MONTH)+"/"+ STR$(DAYS) + "/" + STR$(YEAR)
2880 NEXT II
3000 GOSUB 10000:'# Screening Procedures
3010 DEC1=JUMP:GOSUB 11000
3020 SCRN=DECIMAL
3030 DIM SCRN$(SCRN),SCRNDATE$(SCRN),SCRNCNT$(SCRN)
3040 FOR II=1 TO SCRN
3050    GOSUB 10000
3060    DEC4=JUMP
3070    GOSUB 10000
3080    DEC3=JUMP
3090    GOSUB 10000
3100    DEC2=JUMP
3110    GOSUB 10000
3120    DEC1=JUMP
3130    GOSUB 11000
3140    ADDRESS=DECIMAL
3150    GOSUB 14000
```

```
3160    SCRN$(II)=WORD$
3170    GOSUB 10000:'get date
3180    DEC3=JUMP
3190    GOSUB 10000
3200    DEC2=JUMP
3210    GOSUB 10000
3220    DEC1=JUMP
3230    GOSUB 12000:'rem calculate date
3240    SCRNDATE$(II)=STR$(MONTH)+"/"+STR$(DAYS)+"/"+STR$(YEAR)
3250    GOSUB 10000:'get center name
3260    DEC4=JUMP
3270    GOSUB 10000
3280    DEC3=JUMP
3290    GOSUB 10000
3300    DEC2=JUMP
3310    GOSUB 10000
3320    DEC1=JUMP
3330    GOSUB 11000
3340    ADDRESS=DECIMAL
3350    GOSUB 14000
3360    SCRNCNT$(II)=WORD$
3380 NEXT II
3390 GOSUB 10000:'get Living Will / Organ Donor status
3400 DEC1=JUMP
3410 IF DEC1<10 THEN LIVING$="Patient has signed a Living Will in the past."
3420 IF DEC1<20 AND DEC1>10 THEN LIVING$="Patient desires a Living Will but does not have one at this time."
3430 IF DEC1<30 AND DEC1>20 THEN LIVING$="Patient does not wish a Living Will."
3440 IF DEC1<40 AND DEC1>30 THEN LIVING$="Patient was NO CODE per physician authorizing & reviewing this card at time card was issued."
3441 IF DEC1<50 AND DEC1>40 THEN LIVING$="Living Will status unknown."
3450 ORGAN$="Organ Donor Status unknown."
3460 IF DEC1/5=INT(DEC1/5) THEN ORGAN$="Patient desires donation of organs."
3470 IF DEC1/3=INT(DEC1/3) THEN ORGAN$="Patient desires limited organ donation."
3480 GOSUB 10000:'get # comments
3481 COMMENT=JUMP
3490 DIM COMMENT$(COMMENT)
3495 FOR II=1 TO COMMENT
3500 GOSUB 10000:'get comment
3510 DEC4=JUMP
3520 GOSUB 10000:DEC3=JUMP
3530 GOSUB 10000:DEC2=JUMP
3540 GOSUB 10000:DEC1=JUMP
3550 GOSUB 11000
3560 ADDRESS=DECIMAL
3570 GOSUB 14000
3580 COMMENT$(II)=WORD$
3590 NEXT II
3600 GOSUB 10000:'get name of physician issuing report
3610 DEC4=JUMP
3620 GOSUB 10000:DEC3=JUMP
3630 GOSUB 10000:DEC2=JUMP
3640 GOSUB 10000:DEC1=JUMP
3650 GOSUB 11000
```

```
3670 ADDRESS=DECIMAL
3680 GOSUB 14000
3690 DOCTOR$=WORD$
3700 GOSUB 10000:'get date of report
3710 DEC3=JUMP
3720 GOSUB 10000:DEC2=JUMP
3730 GOSUB 10000:DEC1=JUMP
3740 REM
3750 GOSUB 12000
3760 ISSDATE$=STR$(MONTH)+"/"+STR$(DAYS)+"/"+STR$(YEAR)
3770 REM GET the verification code (1st four letters of patient's mom's maiden name
3780 GOSUB 10000:DEC4  =JUMP
3790 GOSUB 10000:DEC3  =JUMP
3800 GOSUB 10000:DEC2  =JUMP
3810 GOSUB 10000:DEC1  =JUMP
3811 GOSUB 11000:SIGDIG=4:GOSUB 9500
3820 VERIFY$=B62$
3830 REM End of read.  Print to output file.
3840 CLOSE #1:CLOSE #2:CLOSE #3
3841 COLOR 28:LOCATE 16,32:PRINT" ":LOCATE 22,32:PRINT CHR$(219)
3850 OPEN "o",#1,"text.dat"
3860 PRINT #1,VERSION
3870 PRINT #1,GENDER$
3880 PRINT #1,RACE$
3890 PRINT #1,DOB$
3900 PRINT #1,AREA
3901 PRINT #1,PHONE
3902 PRINT #1,PMH
3903 FOR I=1 TO PMH
3904    PRINT #1,PMH$(I)
3905    PRINT #1,PMHDATE$(I)
3906    PRINT #1,PMHCNT$(I)
3907    PRINT #1,PMHMD$(I)
3908 NEXT I
3909 PRINT #1,PSH
3910 FOR I=1 TO PSH
3911    PRINT #1,PSH$(I)
3912    PRINT #1,PSHDATE$(I)
3913    PRINT #1,PSHCNT$(I)
3914    PRINT #1,PSHMD$(I)
3915 NEXT I
3916 PRINT #1,MED
3917 FOR I=1 TO MED
3918    PRINT #1,MED$(I)
3919    PRINT #1,MEDDATE$(I)
3920    PRINT #1,MEDDOSE$(I)
3921    PRINT #1,MEDMD$(I)
3922 NEXT I
3923 PRINT #1,ALLERGY
3924 FOR I=1 TO ALLERGY
3925    PRINT #1,ALLERGY$(I)
3926 NEXT I
3927 PRINT #1,IMMUNE
3928 FOR I=1 TO IMMUNE
```

```
3929    PRINT #1,IMMUNE$(I)
3930    PRINT #1,IMMDATE$(I)
3931 NEXT I
3932 PRINT #1,SCRN
3933 FOR I=1 TO SCRN
3934    PRINT #1,SCRN$(I)
3935    PRINT #1,SCRNDATE$(I)
3936    PRINT #1,SCRNCNT$(I)
3937 NEXT I:PRINT #1,LIVING$:PRINT #1,ORGAN$
3938 PRINT #1,COMMENT
3939 FOR I=1 TO COMMENT
3940    PRINT #1,COMMENT$(I)
3941 NEXT I
3942 PRINT #1,DOCTOR$
3943 PRINT #1,ISSDATE$
3944 PRINT #1,VERIFY$
3945 CLOSE #1
3946 LOCATE 22,32:PRINT" "
3950 RUN "menu"
4000 REM Advanced data entry read/write module
4001 REM Requires x,y and k for color
4002 REM Stores string in HOLD$
4020 XO=0:YO=0:HOLD$=""
4021 CURSOR$(1)=CHR$(221)
4022 CURSOR$(2)=CHR$(223)
4023 CURSOR$(3)=CHR$(222)
4024 CURSOR$(4)=CHR$(220)
4030 I$=INKEY$
4040 CUR=CUR+.1 :IF CUR>4 THEN CUR=1
4050 LOCATE Y+YO,X+XO
4051 PRINT CURSOR$(INT(CUR+.5))
4060 IF I$="" THEN 4030
4065 LOCATE Y+YO,X+XO
4066 PRINT " "
4070 IF ASC(I$)=8 AND XO>0 THEN XO=XO-1:HOLD$=LEFT$(HOLD$,LEN(HOLD$)-1):GOTO 4030
4080 IF ASC(I$)=13 THEN 4130
4081 XO=XO+1
4082 HOLD$=HOLD$+I$
4090 COLOR K
4100 LOCATE Y+YO,X+XO-1
4110 PRINT CHR$(2)
4120 GOTO 4030
4130 HOLD$=RIGHT$(HOLD$,XO)
4140 RETURN
4500 REM Convert to lower case
4510 REM Requires HOLD$, returns HOLD$
4520 FOR I=1 TO LEN(HOLD$)
4530 IF MID$(HOLD$,I,1)>="A" AND MID$(HOLD$,I,1)<="Z" THEN MID$(HOLD$,I,1)=CHR$(ASC(MID$(HOLD$,I,1))+32)
4540 NEXT I
4550 RETURN
7000 REM This routine converts a string base 255 integer into decimal
7010 REM Requires 255 base integer in RESULT$, returns answer in DECIMAL.
```

```
7020 DIG3=ASC(LEFT$(RESULT$,1))
7030 DIG2=ASC(MID$(RESULT$,2,1))
7040 DIG1=ASC(RIGHT$(RESULT$,1))
7050 DECIMAL=DIG3*256^2+DIG2*256^1+DIG1*256^0
7060 RETURN
9500 REM This utility converts decimal --> base62
9510 REM Requires input in        DECIMAL# & SIGDIG (Digits required)
9520 REM Output is stored in      B62$
9521 DECIMAL#=DECIMAL
9522 CODE=0
9523 ZERO=0:IF CODE=1 THEN ZERO=SHIFT
9530 DIG1=ZERO :DIG2=ZERO :DIG3=ZERO :DIG4=ZERO
9540 IF DECIMAL#>=62^3 THEN DECIMAL#=DECIMAL#-62^3:DIG4=DIG4+1:GOTO 9540
9550 IF DECIMAL#>=62^2 THEN DECIMAL#=DECIMAL#-62^2:DIG3=DIG3+1:GOTO 9550
9560 IF DECIMAL#>=62^1 THEN DECIMAL#=DECIMAL#-62^1:DIG2=DIG2+1:GOTO 9560
9570 IF DECIMAL#>=62^0 THEN DECIMAL#=DECIMAL#-62^0:DIG1=DIG1+1:GOTO 9570
9580 B62$=""
9581 REM CODE = 1 if this routine is to encode using the SHIFT cipher
9582 IF CODE=0 THEN 9590
9583 IF DIG1>61 THEN DIG1=DIG1-62:GOTO 9583
9584 IF DIG2>61 THEN DIG2=DIG2-62:GOTO 9584
9585 IF DIG3>61 THEN DIG3=DIG3-62:GOTO 9585
9586 IF DIG4>61 THEN DIG4=DIG4-62:GOTO 9586
9590 N=DIG4:GOSUB 9650:B62$=B62$+N$
9600 N=DIG3:GOSUB 9650:B62$=B62$+N$
9610 N=DIG2:GOSUB 9650:B62$=B62$+N$
9620 N=DIG1:GOSUB 9650:B62$=B62$+N$
9630 B62$=RIGHT$(B62$,SIGDIG)
9640 RETURN
9650 REM This routine converts digits (base 62) to decimal
9660 REM requires incoming N
9670 REM output in n$
9680 IF N<26 THEN N$=CHR$(65+N)
9690 IF N>25 AND N<52 THEN N$=CHR$(ASC("a")+N-26)
9700 IF N>51 AND N<62 THEN N$=CHR$(ASC("0")+N-52)
9710 RETURN
10000 REM Get NEXT address subroutine
10010 REM Automatically increments pointer
10011 REM Returns decimal address in jump (1-61)
10020 POINTER=POINTER+1
10030 IF POINTER>560 THEN POINTER=1
10040 GET #3,POINTER
10050 JUMP=CVD(DECIMAL$)
10060 JUMP=JUMP-SHIFT
10070 IF JUMP<0 THEN JUMP=62+JUMP
10080 RETURN
11000 REM Utility to convert B62 digital information to single decimal digit
11010 REM required SIGDIG to tell it how many digits incoming in DEC()
11020 REM puts out answer in decimal
11040 DECIMAL=DEC4*62^3+DEC3*62^2+DEC2*62^1+DEC1*62^0
```

```
11050 DEC1=0:DEC2=0:DEC3=0:DEC4=0
11060 RETURN
12000 REM Date conversion utility
12001 FLAG1=1
12010 REM Requires incoming dec1, dec2, dec3.
12015 REM DEC4=0
12020    GOSUB 11000
12030 DAYS=DECIMAL
12040 YEAR=0
12050 MONTH=1
12051 I=1888
12060 I=I+1
12061 IF (I-1889+1)/4=INT((I-1889+1)/4) THEN LEAP=1 ELSE LEAP=0
12070  IF DAYS>365 AND LEAP=0 THEN DAYS=DAYS-365:GOTO 12060
12080  IF DAYS>366 AND LEAP=1 THEN DAYS=DAYS-366:GOTO 12060
12090 YEAR=I
12091  IF (YEAR-1889+1)/4= INT((YEAR-1889+1)/4) THEN LEAP=1 ELSE LEAP=0
12100 RESTORE 12190
12110 T=0
12120  T=T+1:READ D
12130  IF T=2 AND LEAP=0 AND DAYS>28 THEN DAYS=DAYS-28:MONTH=MONTH+1:GOTO 12120
12140  IF T=2 AND LEAP=1 AND DAYS>29 THEN DAYS=DAYS-29:MONTH=MONTH+1:GOTO 12120
12150  IF T<>2 AND DAYS>D THEN DAYS=DAYS-D:MONTH=MONTH+1:GOTO 12120
12160 REM
12170 REM Month, Days, and Year have been computed
12180 RETURN
12190 DATA 31,28,31,30,31,30,31,31,30,31,30,31
13000 REM Screen Setup
13010 CLS: COLOR 14, 0: PRINT "              ";
13020 COLOR 7, 0: PRINT "       ";: COLOR 14, 0: PRINT "Decompression Module";
13030 COLOR 7, 0: PRINT "              ";
13040 PRINT "                                        ";
13050 COLOR 14, 0: PRINT "    ";: COLOR 7, 0: PRINT "                                    ";
13060 PRINT "                                        ";
13070 PRINT "          ";: COLOR 9, 0: PRINT "                              ";
13080 COLOR 7, 0: PRINT "         ";
13090 PRINT "          ";: COLOR 9, 0: PRINT "                              ";
13100 COLOR 7, 0: PRINT "            ";: PRINT "         ";
13110 COLOR 9, 0: PRINT "                              ";
13120 COLOR 7, 0: PRINT "            ";: PRINT "      ";
13130 COLOR 9, 0: PRINT "                              ";
13140 COLOR 7, 0: PRINT "             ";: PRINT "                                        ";
13150 PRINT "             ";: COLOR 15, 0: PRINT "+";
13160 COLOR 3, 0: PRINT "Password Authorization";
13170 COLOR 7, 0: PRINT "-------------------+         ";
13180 PRINT "             ";: COLOR 9, 0: PRINT "         ";
13190 COLOR 7, 0: PRINT "                                        ";
13200 COLOR 8, 0: PRINT "";: COLOR 7, 0: PRINT "         ";
13210 PRINT "             ";: COLOR 8, 0: PRINT "+----------------------------------------+";
```

```
13220 COLOR 7, 0: PRINT "                  ";: PRINT "                                                                ";
13230 PRINT "                                                                               ";
13240 PRINT "                          ";: COLOR 8, 0: PRINT "+-+";
13250 COLOR 7, 0: PRINT "              ";: COLOR 8, 0: PRINT " ";
13260 COLOR 7, 0: PRINT "                              ";
13270 PRINT "                        ";: COLOR 8, 0: PRINT "¤";
13280 COLOR 7, 0: PRINT " ";: COLOR 8, 0: PRINT "¤";
13290 COLOR 7, 0: PRINT " ";: COLOR 8, 0: PRINT "Reading ";
13300 COLOR 7, 0: PRINT "     ";: COLOR 8, 0: PRINT " ";
13310 COLOR 7, 0: PRINT "                              ";
13320 PRINT "                          ";: COLOR 8, 0: PRINT "+-+";
13330 COLOR 7, 0: PRINT "              ";: COLOR 8, 0: PRINT " ";
13340 COLOR 7, 0: PRINT "                              ";
13350 PRINT "                         ";: COLOR 8, 0: PRINT "+-+";
13360 COLOR 7, 0: PRINT "              ";: COLOR 8, 0: PRINT " ";
13370 COLOR 7, 0: PRINT "                              ";
13380 PRINT "                         ";: COLOR 8, 0: PRINT "¤";
13390 COLOR 7, 0: PRINT " ";: COLOR 8, 0: PRINT "¤";
13400 COLOR 7, 0: PRINT " ";: COLOR 8, 0: PRINT "Decompressing ";
13410 COLOR 7, 0: PRINT "                              ";
13420 PRINT "                         ";: COLOR 8, 0: PRINT "+-+";
13430 COLOR 7, 0: PRINT "              ";: COLOR 8, 0: PRINT " ";
13440 COLOR 7, 0: PRINT "                              ";
13450 PRINT "                         ";: COLOR 8, 0: PRINT "+-+";
13460 COLOR 7, 0: PRINT "              ";: COLOR 8, 0: PRINT " ";
13470 COLOR 7, 0: PRINT "                              ";
13480 PRINT "                         ";: COLOR 8, 0: PRINT "¤ ¤";
13490 COLOR 7, 0: PRINT " ";: COLOR 8, 0: PRINT "Writing";
13500 COLOR 7, 0: PRINT "      ";: COLOR 8, 0: PRINT " ";
13510 COLOR 7, 0: PRINT "                              ";
13520 PRINT "                         ";: COLOR 8, 0: PRINT "+-+";
13530 COLOR 7, 0
13540 KEY OFF
13550 RETURN
14000 REM Fetch Subroutine
14010 REM Requires incoming ADDRESS
14020 REM Requires access to VLL.LNK (#2) and VLL.DAT (#1)
14030 REM Returns WORD$
14040 COLOR 28:LOCATE 19,32:PRINT CHR$(219):LOCATE 16,32:PRINT" "
14050 GET #2,ADDRESS
14060 RESULT$=SA$:GOSUB 7000:SA=DECIMAL
14070 RESULT$=L$:GOSUB 7000:L=DECIMAL
14075 WORD$=""
14080 FOR I=1 TO L
14090   GET #1,I+SA-1
14100   WORD$=WORD$+C$
14110 NEXT I
14111 COLOR 28:LOCATE 19,32:PRINT" ":LOCATE 16,32:PRINT CHR$(219):COLOR 7
14120 RETURN
```

Compression Utility

Filename: COMP.BAS

```
10 REM Compression Utility
20 REM
30 REM Created by S. Behram, N.T. Grauzlis, S.W. Joseph
40 REM
50 RANDOMIZE (TIMER)
100 GOSUB 10000:REM screen display
105 CODE=1:REM This flags decoding modules in DECtoB62 module.
110 K=11
120 X=20:Y=11
130 GOSUB 11000
131 WORD$=HOLD$
140 LOCATE 7,18:COLOR 9
150 PRINT "Please re-enter authorization code to verify."
160 K=11
170 X=20:Y=11
180 GOSUB 11000
190 IF WORD$<>HOLD$ THEN BEEP:RUN
191 COLOR   17:LOCATE 7,18:S=TIMER
192 PRINT "Please re-enter authorization code to verify."
195 IF TIMER < S+2 THEN 195
196 LOCATE 7,18
197 PRINT "                              "
200 GOSUB 11250
210 FOR I=1 TO LEN(HOLD$)
220 OFFSET=OFFSET+ASC(MID$(HOLD$,I,1))
230 NEXT I
240 IF OFFSET>255 THEN OFFSET=OFFSET-256:GOTO 240
250 LAST$=RIGHT$(HOLD$,1)
260 SHIFT=ASC(LAST$)
270 IF SHIFT>61 THEN SHIFT=SHIFT-62:GOTO 270
280 REM File I/O
290 OPEN "R",#1,"vll.imp",9
300 FIELD #1,3 AS SA$,3 AS L$,3 AS ID$
310 OPEN "r",#2,"vll.dat",1
320 FIELD #2,1 AS C$
330 OPEN "i",#3,"words.num"
340 INPUT #3,COUNT
350 CLOSE #3
360 OPEN "i",#3,"text.dat"
370 OPEN "o",#4,"junk.dat"
380 REM Begin processing
390 INPUT #3,VERSION
400 IF VERSION<>1 THEN PRINT "Error - Unknown Version":STOP
410 DECIMAL=VERSION:SIGDIG=1
420 GOSUB 9500
430 PRINT #4,B62$
435 INPUT #3,RACE$:INPUT #3,GENDER$
440 IF RACE$="white" AND GENDER$="male" THEN DECIMAL=1
450 IF GENDER$="female" AND RACE$="WHITE" THEN DECIMAL=2
460 IF GENDER$="male" AND RACE$="african american" THEN DECIMAL=3
470 IF GENDER$="female" AND RACE$="african american" THEN DECIMAL=4
480 IF GENDER$="male" AND RACE$="hispanic" THEN DECIMAL=5
```

```
490 IF GENDER$="female" AND RACE$="hispanic" THEN DECIMAL=6
500 IF GENDER$="male" AND RACE$="american indian" THEN DECIMAL=7
510 IF GENDER$="female" AND RACE$="american indian" THEN DECIMAL=8
520 IF GENDER$="male" AND RACE$="asian" THEN DECIMAL=9
530 IF GENDER$="female" AND RACE$="asian" THEN DECIMAL=10
540 IF GENDER$="male" AND RACE$="not specified" THEN DECIMAL=11
550 IF GENDER$="female" AND RACE$="not specified" THEN DECIMAL=12
560 IF GENDER$="not specified" AND RACE$="not specified" THEN DECIMAL=13
570 IF GENDER$="sex of rearing differs from genotype" AND RACE$="not specified" THEN DECIMAL=14
580 IF RACE$="white" AND GENDER$="not specified" THEN DECIMAL=15
590 IF RACE$="non-white" AND GENDER$="not specified" THEN DECIMAL=16
600 IF RACE$="african american" AND GENDER$="not specified" THEN DECIMAL=17
610 IF RACE$="american indian" AND GENDER$="not specified" THEN DECIMAL=18
620 IF RACE$="asian" AND GENDER$="not specified" THEN DECIMAL=19
630 IF RACE$="hispanic" AND GENDER$="not specified" THEN DECIMAL=20
631 SIGDIG=1:GOSUB 9500:PRINT #4,B62$
640 REM Date of Birth
650 INPUT #3,WORD$
655 RESULT$=WORD$
660 GOSUB 12000
670 SIGDIG=3:GOSUB 9500
680 PRINT #4, B62$
690 REM Telephone number
700 INPUT #3,AREA
710 SIGDIG=2:DECIMAL=AREA:GOSUB 9500
720 PRINT #4,B62$
730 INPUT #3,PHONE
740 SIGDIG=4:DECIMAL=PHONE:GOSUB 9500
750 PRINT #4,B62$
751 INPUT #3,PMH
760 SIGDIG=1:DECIMAL=PMH:GOSUB 9500
761 PRINT #4,B62$
770 FOR II=1 TO PMH
780    INPUT #3,PMH$:SEARCH$=PMH$
790    GOSUB 15000:'   Locate, fetch and update
800    INPUT #3,PMHDATE$
810    RESULT$=PMHDATE$:GOSUB 12000
820    SIGDIG=3:GOSUB 9500
830    PRINT #4,B62$
840    INPUT #3,PMHCNT$:SEARCH$=PMHCNT$
850    GOSUB 15000
860    INPUT #3,PMHMD$:SEARCH$=PMHMD$
870    GOSUB 15000
880 NEXT II
890 INPUT #3,PSH
900 SIGDIG=1:DECIMAL=PSH:GOSUB 9500
905 PRINT #4,B62$
910 FOR II=1 TO PSH
920    INPUT #3,PSH$:SEARCH$=PSH$
930    GOSUB 15000
940    INPUT #3,PSHDATE$
950    RESULT$=PSHDATE$:GOSUB 12000
960    SIGDIG=3:GOSUB 9500
```

```
970     PRINT #4,B62$
980     INPUT #3,PSHCNT$:SEARCH$=PSHCNT$
990     GOSUB 15000
1000    INPUT #3,PSHMD$:SEARCH$=PSHMD$
1010    GOSUB 15000
1020 NEXT II
1030 REM Medicines
1040 INPUT #3,MED
1050 SIGDIG=1:DECIMAL=MED:GOSUB 9500
1060 PRINT #4,B62$
1070 FOR II=1 TO MED
1080    INPUT #3,MED$:SEARCH$=MED$
1090    GOSUB 15000
1100    INPUT #3,MEDDATE$
1110    RESULT$=MEDDATE$:GOSUB 12000
1120    SIGDIG=3:GOSUB 9500
1130    PRINT #4,B62$
1140    INPUT #3,MEDDOSE$:SEARCH$=MEDDOSE$
1150    GOSUB 15000
1160    INPUT #3,MEDMD$:SEARCH$=MEDMD$
1170    GOSUB 15000
1180 NEXT II
1190 INPUT #3,ALLERGY
1200 SIGDIG=1:DECIMAL=ALLERGY:GOSUB 9500
1210 PRINT #4,B62$
1220 FOR II=1 TO ALLERGY
1230    INPUT #3,ALLERGY$
1240    SEARCH$=ALLERGY$
1250    GOSUB 15000
1260 NEXT II
1270 INPUT #3,IMMUNE
1280 SIGDIG=1:DECIMAL=IMMUNE:GOSUB 9500
1290 PRINT #4,B62$
1300 FOR II=1 TO IMMUNE
1310    INPUT #3,IMMUNE$:SEARCH$=IMMUNE$
1320    GOSUB 15000
1330    INPUT #3,IMMDATE$:RESULT$=IMMDATE$
1340    GOSUB 12000
1350    SIGDIG=3:GOSUB 9500
1360    PRINT #4,B62$
1370 NEXT II
1380 INPUT #3,SCRN
1390 SIGDIG=1:DECIMAL=SCRN:GOSUB 9500
1395 PRINT #4,B62$
1400 FOR II=1 TO SCRN
1410    INPUT #3,SCRN$:SEARCH$=SCRN$
1420    GOSUB 15000
1430    INPUT #3,SCRNDATE$:RESULT$=SCRNDATE$
1440    GOSUB 12000
1450    SIGDIG=3:GOSUB 9500
1460    PRINT #4,B62$
1470      INPUT #3,SCRNCNT$:SEARCH$=SCRNCNT$
1480      GOSUB 15000
1490 NEXT II
```

```
1491 INPUT #3,LIVING$:INPUT #3,ORGAN$
1492 IF LIVING$="Patient has signed a Living Will in the past." THEN ORGAN=5
1493 IF LIVING$="Patient desires a Living Will but does not have one at this time." THEN
ORGAN =15
1494 IF LIVING$="Patient does not wish a Living Will." THEN ORGAN=25
1495 IF LIVING$="Living Will status unknown." THEN ORGAN=45
1496 ORGAN=ORGAN+2
1497 IF ORGAN$="Patient desires donation of organs." THEN ORGAN=ORGAN-2
1498 IF ORGAN$="Patient desires limited organ donation." THEN ORGAN=ORGAN+1
1499 SIGDIG=1:DECIMAL=ORGAN:GOSUB 9500:PRINT #4,B62$
1500 INPUT #3,COMMENT
1510 SIGDIG=1:DECIMAL=COMMENT:GOSUB 9500
1520 PRINT #4,B62$
1530 FOR II=1 TO COMMENT
1540   INPUT #3,COMMENT$:SEARCH$=COMMENT$
1550   GOSUB 15000
1560 NEXT II
1570 INPUT #3,DOCTOR$
1580 SEARCH$=DOCTOR$
1590 GOSUB 15000
1600 INPUT #3,ISSDATE$
1610 RESULT$=ISSDATE$
1620 GOSUB 12000
1630 SIGDIG=3:GOSUB 9500
1640 PRINT #4,B62$
1650 INPUT #3,VERIFY$
1660 B62$=VERIFY$:GOSUB 9000
1670 SIGDIG=4:GOSUB 9500
1680 PRINT #4,B62$
1685 CLOSE #3:CLOSE #4
1690 REM This concludes the dump.
1700 REM Process begins to read this file and convert it into usable/coded matrix
1701 LOCATE 16,32:PRINT" ":COLOR 28:LOCATE 22,32:PRINT CHR$(219)
1710 OPEN "i",#5,"junk.dat"
1720 OPEN "r",#6,"update.inf",1
1730 FIELD #6,1 AS INF$
1731 REM Mask blank spaces on the card with random data
1732 FOR I=1 TO 560
1733   N=INT(RND(1)*61)+1:DECIMAL=N:SIGDIG=1:GOSUB 9500
1734   LSET INF$=B62$
1735   PUT #6,I
1736 NEXT I
1740 INFPNT=OFFSET
1750 INPUT #5,B$
1760 FOR II=1 TO LEN(B$)
1770   B62$=(MID$(B$,II,1)):GOSUB 9000:N=DECIMAL
1780   N=N+SHIFT:IF N>61 THEN N=N-62
1790   DECIMAL=N:SIGDIG=1:GOSUB 9500
1795   LSET INF$=B62$
1800   INFPNT=INFPNT+1
1810   IF INFPNT>560 THEN INFPNT=1
1815   PUT #6,INFPNT
1820 NEXT II
1830 IF EOF(5)=0 THEN 1750
```

```
1840 CLOSE #6:CLOSE #5:CLOSE #2:CLOSE #1
1850 LOCATE 22,32:PRINT" "
1860 RUN "menu"
7000 REM This routine converts a string base 255 integer into decimal
7010 REM Requires 256 base integer in RESULT$, returns answer in DECIMAL.
7020 DIG3=ASC(LEFT$(RESULT$,1))
7030 DIG2=ASC(MID$(RESULT$,2,1))
7040 DIG1=ASC(RIGHT$(RESULT$,1))
7050 DECIMAL=DIG3*256^2+DIG2*256^1+DIG1*256^0
7060 RETURN
8000 REM Retrieves string located at CURR.  Returns it in Item$
8010 REM Retrieve item and current JMP location
8020 GET #1,CURR
8030 RESULT$=SA$:GOSUB 7000:SA=DECIMAL
8040 RESULT$=L$:GOSUB 7000:L=DECIMAL
8050 RESULT$=ID$:GOSUB 7000:ID=DECIMAL
8060 ITEM$=""
8080 FOR I=1 TO L
8090    GET #2,I+SA-1
8100    ITEM$=ITEM$+C$
8110 NEXT I
8120 IF BUG=0 THEN 8999
8125 IF SA<10 THEN GOTO 8999:'Rem too close to the end
8130 REM This is to fix DOS bug
8140 IF (SA-1)/256<>INT((SA-1)/256) THEN 8999
8150 HOLD=CURR:H$=ITEM$
8155 BUG=0
8160 CURR=CURR-1:GOSUB 8000:LOW$=ITEM$
8170 CURR=CURR+2:GOSUB 8000:HIGH$=ITEM$
8171 CURR=HOLD:GOSUB 8000
8180 BUG=1
8190 REM ITEM$=H$:CURR=HOLD
8200 IF ITEM$>LOW$ AND ITEM$<HIGH$ THEN 8999
8210 REM Bug detected.
8220 BEEP
8230 P$=RIGHT$(ITEM$,1):ITEM$=P$+LEFT$(ITEM$,LEN(ITEM$)-1)
8999 RETURN
9000 REM This utility converts base62 --> decimal
9010 REM Requires string stored in B62$
9020 REM Ouput stored in        DECIMAL#
9030 DECIMAL#=0
9040 D=LEN(B62$)
9050 FOR I=D TO 1 STEP -1
9060    C$=MID$(B62$,I,1)
9070    IF C$>="A" AND C$<="Z" THEN C=ASC(C$)-65
9080    IF C$>="a" AND C$<="z" THEN C=26+ASC(C$)-97
9090    IF C$>="0" AND C$<="9" THEN C=52+ASC(C$)-ASC("0")
9100    DECIMAL#=DECIMAL#+C*(62^(D-I))
9110 NEXT I
9111 DECIMAL=DECIMAL#
9120 RETURN
9500 REM This utility converts decimal --> base62
9510 REM Requires input in        DECIMAL# & SIGDIG (Digits required)
9520 REM Output is stored in      B62$
```

```
9521 REM CODE = 1 if this routine is to encode using the SHIFT cipher
9522 CODE=0
9523 ZERO=0:IF CODE=1 THEN ZERO=SHIFT
9524 REM The decipher code should probably be located in the routine that converts JUNK$
into the final code.
9525 DECIMAL#=DECIMAL
9530 DIG1 =ZERO :DIG2 =ZERO :DIG3 =ZERO :DIG4 =ZERO
9540 IF DECIMAL#>=62^3 THEN DECIMAL#=DECIMAL#-62^3:DIG4=DIG4+1:GOTO
9540
9550 IF DECIMAL#>=62^2 THEN DECIMAL#=DECIMAL#-62^2:DIG3=DIG3+1:GOTO
9550
9560 IF DECIMAL#>=62^1 THEN DECIMAL#=DECIMAL#-62^1:DIG2=DIG2+1:GOTO
9560
9570 IF DECIMAL#>=62^0 THEN DECIMAL#=DECIMAL#-62^0:DIG1=DIG1+1:GOTO
9570
9580 B62$=""
9581 REM CODE = 1 if this routine is to encode using the SHIFT cipher
9582 IF CODE=0 THEN 9590
9583 IF DIG1>61 THEN DIG1=DIG1-62:GOTO 9583
9584 IF DIG2>61 THEN DIG2=DIG2-62:GOTO 9584
9585 IF DIG3>61 THEN DIG3=DIG3-62:GOTO 9585
9586 IF DIG4>61 THEN DIG4=DIG4-62:GOTO 9586
9590 N=DIG4:GOSUB 9650:B62$=B62$+N$
9600 N=DIG3:GOSUB 9650:B62$=B62$+N$
9610 N=DIG2:GOSUB 9650:B62$=B62$+N$
9620 N=DIG1:GOSUB 9650:B62$=B62$+N$
9630 B62$=RIGHT$(B62$,SIGDIG)
9640 RETURN
9650 REM This routine converts digits (base 62) to decimal
9660 REM requires incoming N
9670 REM output in n$
9680 IF N<26 THEN N$=CHR$(65+N)
9690 IF N>25 AND N<52 THEN N$=CHR$(ASC("a")+N-26)
9700 IF N>51 AND N<62 THEN N$=CHR$(ASC("0")+N-52)
9710 RETURN
10000 CLS: COLOR 14, 0: PRINT "              ";
10010 COLOR 7, 0: PRINT "       ";: COLOR 14, 0: PRINT "Compression Module  ";
10020 COLOR 7, 0: PRINT "            ";
10030 PRINT "                                    ";
10040 COLOR 14, 0: PRINT "    ";: COLOR 7, 0: PRINT "                              ";
10050 PRINT "                                    ";
10060 PRINT "            ";: COLOR 9, 0: PRINT "                   ";
10070 COLOR 7, 0: PRINT "            ";
10080 PRINT "            ";: COLOR 9, 0: PRINT "         ";: PRINT "         ";
10090 COLOR 7, 0: PRINT "            ";: PRINT "        ";
10100 COLOR 9, 0: PRINT "                              ";
10110 COLOR 7, 0: PRINT "            ";: PRINT "         ";
10120 COLOR 9, 0: PRINT "                      ";
10130 COLOR 7, 0: PRINT "            ";: PRINT "       ";
10140 PRINT "                ";: COLOR 15, 0: PRINT "+";
10150 COLOR 3, 0: PRINT "Password Authorization";
10160 COLOR 7, 0: PRINT "--------------------+           ";
```

```
10170 PRINT "           □";: COLOR 9, 0: PRINT "     ";
10180 COLOR 7, 0: PRINT " ";: COLOR 14, 0: PRINT "    ";
10190 COLOR 7, 0: PRINT "           ";
10200 COLOR 8, 0: PRINT "□";: COLOR 7, 0: PRINT "          ";
10210 PRINT "              ";: COLOR 8, 0: PRINT "+----------------------------------------+";
10220 COLOR 7, 0: PRINT "             ";: PRINT "   ";
10230 PRINT "                                               ";
10240 PRINT "                      ";: COLOR 8, 0: PRINT "+-+";
10250 COLOR 7, 0: PRINT "           ";: COLOR 8, 0: PRINT " ";
10260 COLOR 7, 0: PRINT "                        ";
10270 PRINT "                   ";: COLOR 8, 0: PRINT "□";
10280 COLOR 7, 0: PRINT " ";: COLOR 8, 0: PRINT "□";
10290 COLOR 7, 0: PRINT " ";: COLOR 8, 0: PRINT "Reading ";
10300 COLOR 7, 0: PRINT "     ";: COLOR 8, 0: PRINT " ";
10310 COLOR 7, 0: PRINT "                         ";
10320 PRINT "                      ";: COLOR 8, 0: PRINT "+-+";
10330 COLOR 7, 0: PRINT "          ";: COLOR 8, 0: PRINT " ";
10340 COLOR 7, 0: PRINT "                        ";
10350 PRINT "                      ";: COLOR 8, 0: PRINT "+-+";
10360 COLOR 7, 0: PRINT "          ";: COLOR 8, 0: PRINT " ";
10370 COLOR 7, 0: PRINT "                        ";
10380 PRINT "                   ";: COLOR 8, 0: PRINT "□";
10390 COLOR 7, 0: PRINT " ";: COLOR 8, 0: PRINT "□";
10400 COLOR 7, 0: PRINT " ";: COLOR 8, 0: PRINT "Compressing ";
10410 COLOR 7, 0: PRINT "          ";
10420 PRINT "                      ";: COLOR 8, 0: PRINT "+-+";
10430 COLOR 7, 0: PRINT "          ";: COLOR 8, 0: PRINT " ";
10440 COLOR 7, 0: PRINT "                        ";
10450 PRINT "                      ";: COLOR 8, 0: PRINT "+-+";
10460 COLOR 7, 0: PRINT "          ";: COLOR 8, 0: PRINT " ";
10470 COLOR 7, 0: PRINT "                        ";
10480 PRINT "                   ";: COLOR 8, 0: PRINT "□ □";
10490 COLOR 7, 0: PRINT " ";: COLOR 8, 0: PRINT "Writing";
10500 COLOR 7, 0: PRINT "    ";: COLOR 8, 0: PRINT " ";
10510 COLOR 7, 0: PRINT "                        ";
10520 PRINT "                      ";: COLOR 8, 0: PRINT "+-+";
10530 COLOR 7,0
10540 KEY OFF
10550 RETURN
11000 REM Advanced data entry read/write module
11010 REM Requires x,y and k for color
11020 REM Stores string in HOLD$
11030 XO=0:YO=0:HOLD$=""
11040 CURSOR$(1)=CHR$(221)
11050 CURSOR$(2)=CHR$(223)
11060 CURSOR$(3)=CHR$(222)
11070 CURSOR$(4)=CHR$(220)
11080 I$=INKEY$
11090 CUR=CUR+.1 :IF CUR>4 THEN CUR=1
11100 LOCATE Y+YO,X+XO
11110 PRINT CURSOR$(INT(CUR+.5))
11120 IF I$="" THEN 11080
11130 LOCATE Y+YO,X+XO
```

```
11140 PRINT " "
11150 IF ASC(I$)=8 AND XO>0 THEN XO=XO-1:HOLD$=LEFT$(HOLD$,LEN(HOLD$)-1):GOTO 11080
11160 IF ASC(I$)=13 THEN 11230
11170 XO=XO+1
11180 HOLD$=HOLD$+I$
11190 COLOR K
11200 LOCATE Y+YO,X+XO-1
11210 PRINT CHR$(2)
11220 GOTO 11080
11230 HOLD$=RIGHT$(HOLD$,XO)
11240 RETURN
11250 REM Convert to lower case
11260 REM Requires HOLD$, returns HOLD$
11270 FOR I=1 TO LEN(HOLD$)
11280 IF MID$(HOLD$,I,1)>="A" AND MID$(HOLD$,I,1)<="Z" THEN MID$(HOLD$,I,1)=CHR$(ASC(MID$(HOLD$,I,1))+32)
11290 NEXT I
11300 RETURN
12000 REM Date to decimal conversion utility
12010 REM Requires date stored in RESULT$
12020 REM Format:  month/days/year    Ex:  11 / 2 / 1968
12030 REM Output will be in decimal, representing the number of days begining
12040 REM January 1, 1889
12050 REM
12060 REM Parse RESULT$ --> Month / Days / Year
12061 RESULT$=RESULT$+"/"
12070 MONTH$="":DAYS$="":YEAR$=""
12080 GOSUB 12500:MONTH =VAL(WORD$)
12090 GOSUB 12500:DAYS =VAL(WORD$)
12100 GOSUB 12500:YEAR =VAL(WORD$)
12110 FOR I=1889 TO YEAR-1
12120   IF (I-1889+1)/4=INT((I-1889+1)/4) THEN LEAP=1 ELSE LEAP=0
12130   IF LEAP=1 THEN DAYS=DAYS+366
12140   IF LEAP=0 THEN DAYS=DAYS+365
12150 NEXT I
12160 RESTORE 12160
12161 IF(YEAR-1889+1)/4=INT((YEAR-1889+1)/4) THEN LEAP=1 ELSE LEAP=0
12170 FOR I=1 TO MONTH-1
12180   READ D
12190   IF I=2 AND LEAP=0 THEN DAYS=DAYS+28
12200   IF I=2 AND LEAP=1 THEN DAYS=DAYS+29
12210   IF I<>2 THEN DAYS=DAYS+D
12220 NEXT I
12230 REM The number of days is now contained in Days
12240 DECIMAL=DAYS
12250 RETURN
12260 DATA 31,28,31,30,31,30,31,31,30,31,30,31
12500 REM Parse based on "/" character
12505 WORD$=""
12510 FOR I=1 TO LEN(RESULT$)
12520   HOLD$=MID$(RESULT$,I,1)
12530   IF HOLD$<>"/" THEN WORD$=WORD$+HOLD$:NEXT I
12540 RESULT$=RIGHT$(RESULT$,LEN(RESULT$)-I)
```

```
12570 RETURN
15000 REM This utility locates, fetches and update the ID information
15010 REM to the JUNK file already open
15020 REM To be used only when entries are stored in either SEARCH$
15030 REM No output per se from this routine other than disk output.
15035 LOCATE 19,32:COLOR 28:PRINT CHR$(219):LOCATE 16,32:PRINT" "
15040 GOSUB 16000: REM Search Algorithm
15045 IF MATCH=0 THEN PRINT "Error - Word not found in VLL":STOP
15050 RESULT$=STORE$:GOSUB 7000
15060 SIGDIG=4:GOSUB 9500
15070 PRINT #4,B62$
15075 LOCATE 19,32:COLOR 28:PRINT" ":LOCATE 16,32:PRINT CHR$(219):COLOR 8
15080 RETURN
16000 REM Scan subroutine V.1.0
16010 REM Created by S. Behram on 10/16/1993
16020 REM N.T. Grauzlis, S.W. Joseph
16030 REM Requires incoming search string in SEARCH$
16040 REM Requires the total number of words in entire dbase in COUNT
16050 REM Also needs VLL files to have already been opened and field
16060 REM statements declared:
16070 REM OPEN "R",#1,"vll.jmp",9    FIELD #1,3 as sa$,3 as I$,3 as id$
16080 REM OPEN "R",#2,"vll.dat",1    FIELD #2,1 as c$
16090 REM
16100 REM The STR2DEC subroutine must be install at line 7000
16110 REM Program returns MATCH=1 for positive match
16120 REM Program returns strings FIND(1-6)$ as closest matches
16130 REM Begin dbase search
16140 JMP=INT(COUNT/2+.5):CURR=JMP
16150 REM Retrieve item and current JMP location
16160 GOSUB 8000:'routine to retrieve string at CURR
16170 IF ITEM$=SEARCH$ THEN MATCH=1:STORE$=ID$:GOTO 16250
16180 JMP=INT(JMP/2+.5)
16190 IF JMP<1 THEN JMP=1
16200 IF ITEM$>SEARCH$ THEN CURR=CURR-JMP:IF CURR<1 THEN CURR=1
16210 IF ITEM$<SEARCH$ THEN CURR=CURR+JMP
16220 IF ITEM$=LAST$ THEN MATCH=0:GOTO 16250
16230 LAST$=HOLD$:HOLD$=ITEM$
16240 GOTO 16160
16250 REM Search complete
16251 GOTO 16390
16260 REM Will store the results of search in find$(1-6)
16270 REM Closest answer is in curr
16280 IF CURR<3 THEN CURR=CURR+1:GOTO 16280
16290 IF CURR>COUNT-3 THEN CURR=CURR-1:GOTO 16290
16300 CR=0:CRR=CURR
16310 FOR CURR=CURR-2 TO CURR+3
16320    CR=CR+1
16330    GOSUB 8000
16340    FIND$(CR)=ITEM$
16350 NEXT CURR:CURR=CRR
16360 HOLD$=FIND$(1)
16370 FIND$(1)=FIND$(3)
16380 FIND$(3)=HOLD$
16390 RETURN
```

We claim:

1. A data compression/decompression method using very large lists which define a modifiable static dictionary means comprising a primary and secondary dictionary for data compression with a means for input of informational (INFO) data to a means for computing, the computing means transforms the INFO data into confidentially protected output encoded data, the output encoded data is transmitted over a data transmission means for ultimate data storage by a data storage means, the method comprising the steps of:

assigning a sequential primary unique identification (ID) number to each word that is a part of the input INFO data that is within the very large list of data, the ID number is equal to a pointer position for each of these words in the secondary dictionary, the secondary dictionary has a structure for these words with the following features: i) each word can be a single phrase that is at least one word associated therewith, ii) the length of each word and iii) the primary unique ID number;

manipulating sequentially each of the primary unique ID numbers by a mathematical number base conversion technique that transforms the primary unique ID numbers into secondary numbers;

using at least a first designated key code by a user of the method for encryption of the secondary numbers;

transmitting each of the secondary encrypted numbers over the data transmission means sequentially for ultimate storage in the storage means;

whereby the secondary encrypted numbers can be retrieved at a later time even when the modifiable primary static dictionary changes.

2. The method of claim 1 further includes the technique of decompression of the output encoded data at the data storage means by further including steps of:

inputting the at least first user key code into the computing means;

inputting the encrypted secondary numbers from the data storage means;

transforming sequentially each of the secondary unique ID numbers by the mathematical number base conversion technique using the user designated key code;

sequentially translating the primary numbers into words stored in a third dictionary that enables vertical integration of the primary dictionary, and outputting the words from the computing means into a text readable form.

3. The method of claim 2 wherein the very large lists of data comprises a medical patient's data file and the output storage means is a wallet sized card, the at least first designated key code for encryption of the secondary numbers is an mathematically manipulated offset technique that locates a starting point within the data string, a specialized data compression/decompression converts dates and telephone numbers into a different number base, and each line of output data on the card has two checksum values whereby error-free data entry is ensured for accuracy of the patient's file.

4. The method of claim 3 wherein the key code is an alphanumeric code confidentially known by the user to maintain privacy of the INFO data.

5. The method of claim 3 wherein the the key code is encoded on the card to allow access by the possessor of the card.

6. The method of claim 1 wherein the output encoded data is alphanumeric characters encoded on the storage means such as a visual printed card, a magnetic strip on a card, an optical card, a smart card and bar coded strip card.

7. A medical data card for storing confidential medical data of a patient in encoded form that maintains privacy of the patient comprising:

a portable wallet sized card with a data storage medium;

the encoded form of the medical data is in a form determined by a method using:

very large lists stored in a computing means that define a modifiable static dictionary means comprising a primary and secondary dictionary with a means for input of the patient's medical data into the computing means which transforms the medical information into confidentially protected alphanumeric output encoded data, the output encoded data is stored on the card by:

assigning a sequential primary unique identification (ID) number to each word that is a part of the input medical data that is within the very large list of data, the ID number is equal to a pointer position of each of these words in the secondary dictionary;

manipulating sequentially each of the primary unique ID numbers by a mathematical number base conversion technique that transforms the primary unique ID numbers into secondary numbers;

using at least a first designated key code preselected by the patient for encryption of the medical data; and storing each of the secondary numbers sequentially on the card storage medium which contains the encoded information.

8. The medical data card of claim 7 wherein the at least first designated key code preselected by the patient is a number confidentially known by the patient whereby privacy of the medical data is maintained.

9. The medical data card of claim 7 wherein the the at least first designated key code preselected by the patient is encoded on the card to allow access by a possessor of the card.

10. The medical data card of claim 7 wherein the output encoded data is alphanumeric characters printed on the card for optical scanning of the card, each line of output encoded data on the card has two checksum values to ensure accuracy of medical data entry.

11. The medical data card of claim 7 wherein the output encoded data is in a magnetic data form for magnetic data reading means.

12. The medical data card of claim 7 wherein the output encoded data is in a bar coded data form that is used in conjunction with optical scanning means.

13. The medical data card of claim 7 wherein the output encoded data is in digital form for storage media such as a smart card, optical card and chip cards.

14. The medical data card of claim 7 wherein the output encoded data is in a mixed modality format of alphanumerics and magnetic strip.

15. The medical data card of claim 7 wherein the card is a storage medium of the patients medical data such as specialized obstetrics/gynecology information and specialized pediatrics information concerning infants.

* * * * *